US010561655B2

(12) United States Patent
Xie et al.

(10) Patent No.: US 10,561,655 B2
(45) Date of Patent: Feb. 18, 2020

(54) SHP2 INHIBITORS AND USES THEREOF

(71) Applicant: SYNBLia Therapeutics, Inc., Dover, DE (US)

(72) Inventors: Yinong Xie, Dover, DE (US); Lee E. Babiss, Dover, DE (US)

(73) Assignee: SYNBLia Therapeutics, Inc., Dover, DE (US)

(*) Notice: Subject to any disclaimer, the term of this patent is extended or adjusted under 35 U.S.C. 154(b) by 0 days.

(21) Appl. No.: 16/356,360

(22) Filed: Mar. 18, 2019

(65) Prior Publication Data
US 2019/0290649 A1 Sep. 26, 2019

Related U.S. Application Data

(60) Provisional application No. 62/646,107, filed on Mar. 21, 2018.

(51) Int. Cl.
C07D 213/02 (2006.01)
C07D 213/24 (2006.01)
C07D 213/63 (2006.01)
A61K 31/513 (2006.01)
A61P 35/00 (2006.01)
A61P 37/00 (2006.01)
A61K 31/519 (2006.01)
C07D 487/04 (2006.01)
C07D 213/64 (2006.01)
A61K 31/4402 (2006.01)
C07D 401/04 (2006.01)

(52) U.S. Cl.
CPC ........ A61K 31/513 (2013.01); A61K 31/4402 (2013.01); A61K 31/519 (2013.01); A61P 35/00 (2018.01); A61P 37/00 (2018.01); C07D 213/64 (2013.01); C07D 401/04 (2013.01); C07D 487/04 (2013.01)

(58) Field of Classification Search
CPC ... C07D 213/02; C07D 213/24; C07D 213/63
See application file for complete search history.

(56) References Cited

U.S. PATENT DOCUMENTS 8,350,043 B2 * 1/2013 Letourneau .......... C07D 213/82
546/261

FOREIGN PATENT DOCUMENTS

| CN | 102080087 A | 6/2011 |
| CN | 107286150 A | 10/2017 |
| CN | 108113984 A | 6/2018 |
| CN | 108341791 A | 7/2018 |
| CN | 108578395 A | 9/2018 |
| CN | 109646441 A | 4/2019 |
| WO | 2009049098 A2 | 4/2009 |
| WO | 2014176488 A1 | 10/2014 |
| WO | 2015003094 A2 | 1/2015 |
| WO | 2015107494 A1 | 7/2015 |
| WO | 2015107495 A1 | 7/2015 |
| WO | WO 2015/200843 | * 12/2015 |
| WO | 2015107493 A1 | 7/2016 |
| WO | 2016196569 A1 | 12/2016 |
| WO | 2016196591 A1 | 12/2016 |
| WO | 2016203404 A1 | 12/2016 |
| WO | 2016203405 A1 | 12/2016 |
| WO | 2016203406 A1 | 12/2016 |
| WO | 2017100279 A1 | 6/2017 |
| WO | 2017156397 A1 | 9/2017 |
| WO | 2017211303 A1 | 12/2017 |
| WO | 2017216706 A1 | 12/2017 |
| WO | 2018013597 A1 | 1/2018 |
| WO | WO 2018/013597 | * 1/2018 |
| WO | 2018057884 A1 | 3/2018 |
| WO | 2018081091 A1 | 5/2018 |
| WO | 2018130928 A1 | 7/2018 |
| WO | 2018136264 A1 | 7/2018 |
| WO | 2018136265 A1 | 7/2018 |
| WO | 2018160731 A1 | 9/2018 |
| WO | 2018172984 A1 | 9/2018 |
| WO | 2018218133 A1 | 11/2018 |
| WO | 2019051084 A1 | 3/2019 |
| WO | 2019067843 A1 | 4/2019 |
| WO | 2019075265 A1 | 4/2019 |

* cited by examiner

Primary Examiner — Bruck Kifle
(74) Attorney, Agent, or Firm — Maschoff Brennan; Brent A. Johnson; Yuefen Zhou

(57) ABSTRACT

Compounds of Formula 1 as inhibitors of protein tyrosine phosphatase SHP2 are disclosed. The pharmaceutical compositions comprising compounds of Formula 1, methods of synthesis of these compounds, methods of treatment for diseases associated with the aberrant activity of SHP2 such as cancer using these compounds or compositions containing these compounds are also disclosed.

16 Claims, No Drawings

SHP2 INHIBITORS AND USES THEREOF

CROSS-REFERENCE TO RELATED APPLICATION

This application claims the benefit of U.S. Provisional Application No. 62/646,107, filed Mar. 21, 2018; which is incorporated by reference by its entirety.

FIELD

The present disclosure relates to inhibitors of protein tyrosine phosphatase SHP2 (Src Homolgy-2 phosphatase) and their use in treating SHP2 mediated disorders. More specifically, this disclosure is directed to compounds that inhibit SHP2 and compositions comprising these compounds, methods of treating diseases associated with the aberrant activity of SHP2, and methods of synthesizing these compounds.

BACKGROUND

Tyrosyl phosphorylation regulates human cellular processes from cell differentiation to growth and apoptosis etc. Tyrosyl phosphorylation is regulated by protein-tyrosine kinases (PTK) and protein-tyrosine phosphatases (PTP). The imbalance of regulation governed by PTK and PTP activity leads to various diseases.

SHP2 is a non-receptor protein tyrosine phosphatase (PTP) encoded by the Protein-tyrosine phosphatase non-receptor type 11 (PTPN11) gene. It contains two N-terminal Src homology 2 domains (N—SH2 and C—SH2), a catalytic domain, and a C-terminal tail. The protein exists in an inactive, auto-inhibited basal conformation that blocks the active site. This self-inhibition state is stabilized by a binding network involving residues from both the N—SH2 and catalytic domains. Stimulation by, for example, cytokines or growth factors results in enzymatic activation of SHP2 and makes the active site available for dephosphorylation of PTPN11 substrates.

SHP2 is widely expressed in most tissues and contributes to various cellular functions including proliferation, differentiation, cell cycle maintenance and migration. It is involved in signaling through the Ras-mitogen-activated protein kinase, the JAK-STAT, EGFR, or the phosphoinositol 3-kinase-AKT pathways.

Mutations in the PTPN11 gene and subsequently in SHP2 lead to hyperactivation of SHP2 catalytic activity, and have been identified in several human diseases, such as Noonan Syndrome, Leopard Syndrome, juvenile myelomonocytic leukemias, neuroblastoma, melanoma, acute myeloid leukemia and cancers of the breast, lung, melanoma, neuroblastoma, hepatocellular carcinoma, and colon. These mutations disrupt the auto-inhibition between the N—SH2 domains and the catalytic site allowing constitutive access of substrates to the catalytic site of the enzyme.

Additionally, there is growing evidence that PTPN11/SHP2 may be implicated in immune evasion during tumorigenesis, and hence a SHP2 inhibitor could stimulate the immune response in cancer patients.

Furthermore, SHP2 plays an important role in JAK/STAT3 pathway, with clear correlation between its phosphatase activity and systemic autoimmunity, thus a SHP2 inhibitor could be used to treat autoimmune diseases such as Lupus and Rheumatoid Arthritis.

Therefore, SHP2 represents a highly attractive target for the development of novel therapies for the treatment of various diseases associated with the aberrant activity of SHP2. The compounds of the present disclosure that are capable of inhibiting the activity of SHP2, possess great potential as novel small molecule therapies for the treatment of various diseases mentioned above.

SUMMARY

This disclosure relates to compounds represented by Formula 1:

(Formula 1)

or a pharmaceutically acceptable salt thereof; wherein X is S, O, $NR^A$, $CHR^A$, SO, $SO_2$, CO, or a bond; Ring A is an optionally substituted aryl, heteroaryl, or bicyclic ring system; Ring B is an optionally substituted heterocyclic ring system, including non-aromatic ring system and heteroaryl, comprising a mono-cyclic ring, a bicyclic ring system, a tricyclic ring system, or a tetracyclic ring system, wherein the heterocyclic ring system contains at least 2 ring nitrogen atoms; and $R^A$ is H or $C_{1-6}$ hydrocarbyl.

Some embodiments include a method of treating diseases, disorders, or conditions associated with the aberrant activity of SHP2, such as but not limited to, cancer, and autoimmune disorders, comprising administering a therapeutically effective amount of a compound described herein, or any optionally substituted compound represented in Table I below, or a pharmaceutically acceptable salt thereof (referred to collectively herein as a "subject compound"), to a patient in need thereof.

Some embodiments include use of a compound described herein, such as a compound of Formula 1, a subject compound described herein in the manufacture of a medicament for the treatment of cancer, autoimmune diseases, inflammatory diseases, autoinflammatory conditions, and other SHP2 mediated disorders in a mammal.

Some embodiments include a pharmaceutical composition comprising a therapeutically effective amount of a subject compound described herein, or a pharmaceutically acceptable salt thereof, in combination with at least one pharmaceutically acceptable vehicle, diluent, or carrier.

Some embodiments include a process for making a pharmaceutical composition comprising combining a subject compound described herein and at least one pharmaceutically acceptable carrier.

Some embodiments include a medicament comprising a composition comprising a therapeutically effective amount of a subject compound.

Some embodiments include a kit comprising a medicament of above and a label indicating that the medicament is for treating a disease, disorders, or condition associated with the aberrant activity of SHP2.

DESCRIPTION

Unless otherwise indicated, any reference to a compound herein by structure, name, or any other means, includes pharmaceutically acceptable salts, such as sodium, potassium, and ammonium salts, or HCl, $H_2SO_4$, $HCO_2H$, and $CF_3CO_2H$ salts; prodrugs, such as ester prodrugs; alternate solid forms, such as polymorphs, solvates, hydrates, etc.; tautomers; or any other chemical species that may rapidly convert to a compound described herein under conditions in which the compounds are used as described herein.

If stereochemistry is not indicated, a name or structural depiction includes any stereoisomer or any mixture of stereoisomers.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" is broad, and includes a moiety that occupies a position normally occupied by one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent may be an ordinary organic moiety known in the art, which may have a molecular weight of 15 g/mol to 200 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, P, Si, F, Cl, Br, or I; provided that the substituent includes one C, N, O, S, P, Si, F, Cl, Br, or I atom. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, al kylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, phosphonic acid, etc.

For convenience, the term "molecular weight" is used with respect to a moiety or part of a molecule to indicate the sum of the atomic masses of the atoms in the moiety or part of a molecule, even though it may not be a complete molecule.

The term "treating" or "treatment" includes the diagnosis, cure, mitigation, treatment, or prevention of disease in man or other animals, or any activity that otherwise affects the structure or any function of the body of man or other animals.

A hydrogen atom in any position of a compound of Formula 1 may be replaced by a deuterium. In some embodiments, a compound of Formula 1 contains a deuterium atom or multiple deuterium atoms.

With respect to Formula 1, in some embodiments Ring A is: optionally substituted phenyl, optionally substituted naphthalen-1-yl, optionally substituted pyridin-3-yl, optionally substituted pyridin-4-yl, optionally substituted 2-oxo-1,2-dihydropyridin-4-yl, optionally substituted 1H-indol-4-yl, optionally substituted 2-oxoindolin-4-yl, optionally substituted indolin-4-yl, optionally substituted 3-(2-oxo-2,5-dihydro-1H-pyrrole-3-carboxannido)phenyl, optionally substituted 3-(4-oxo-4H-pyrido[1,2-a]pyrimidine-3-carboxannido)phenyl, optionally substituted 3-(4-oxo-4H-pyrazino[1,2-a]pyrimidine-3-carboxannido)phenyl, optionally substituted 3-(5-oxo-5H-thiazolo[3,2-a]pyrimidine-6-carboxamido)phenyl, optionally substituted 3-(5-oxo-1,5-dihydroinnidazo[1,2-a]pyrimidine-6-carboxannido)phenyl, or optionally substituted 3-(4-oxo-6,7,8,9-tetrahydro-4H-pyrido[1,2-a]pyrimidine-3-carboxannido)phenyl. For example, Ring A may be 2,3-dichlorophenyl, 2,3-dichloropyridin-4-yl, or 2-amino-3-chloropyridin-4-yl.

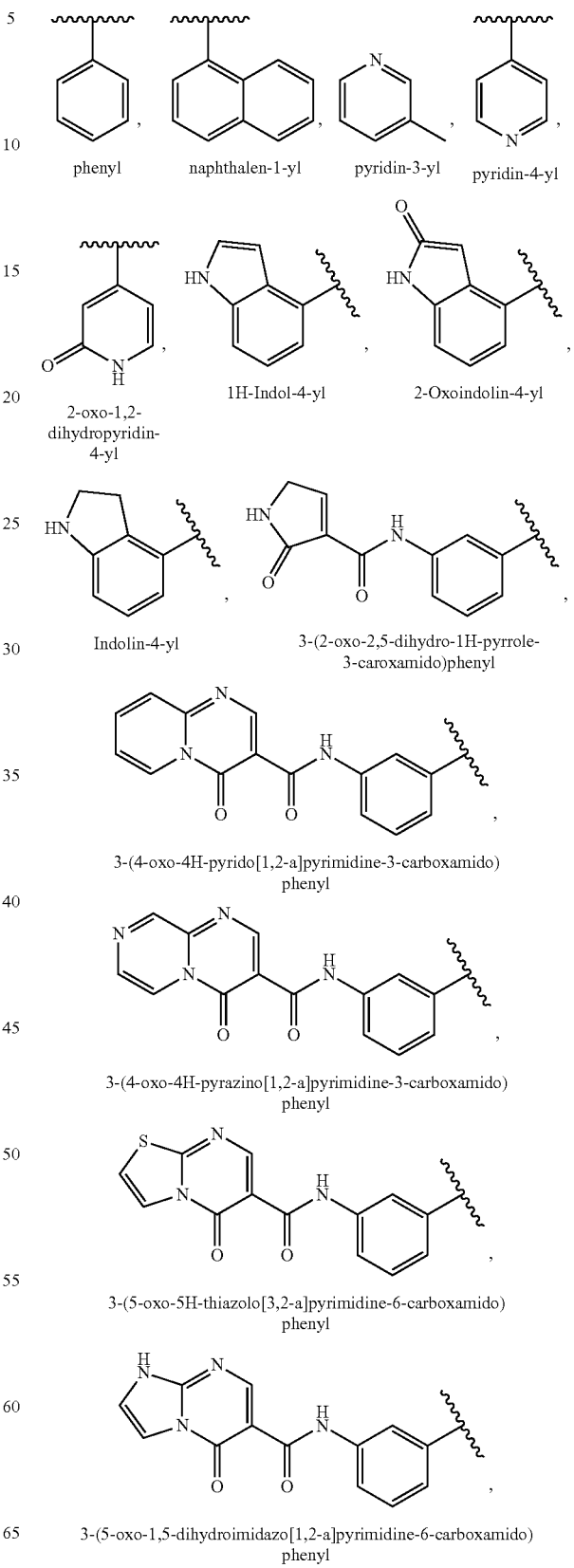

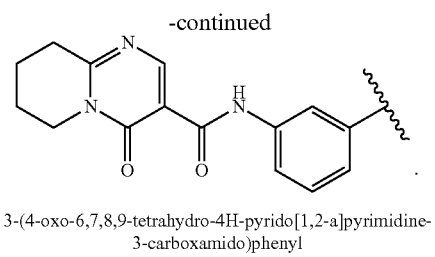

3-(4-oxo-6,7,8,9-tetrahydro-4H-pyrido[1,2-a]pyrimidine-3-carboxamido)phenyl

In some embodiments, Ring A is unsubstituted.
In some embodiments, Ring A has a Cl substituent.
In some embodiments, Ring A has two Cl substituents.
In some embodiments, Ring A has two Cl substituents at 2- and 3-positions; for example, Ring A is 2,3-dichlorophenyl.
In some embodiments, Ring A has a $CF_3$ substituent.
In some embodiments, Ring A has a $CF_3$ substituent at 2-position.
In some embodiments, Ring A has an $NH_2$ substituent.
In some embodiments, Ring A has an $NH_2$ substituent and a Cl substituent.
In some embodiments, Ring A has an $NH_2$ substituent and a Cl substituent with Cl at 2-position and $NH_2$ at 5-position.
In some embodiments, Ring A has an $NH_2$ substituent and a Cl substituent with Cl at 2-position and $NH_2$ at 3-position.
In some embodiments, Ring A has an $NH_2$ substituent and a Cl substituent with Cl at 3-position and $NH_2$ at 2-position.
In some embodiments, Ring A has an —$OCH_3$ substituent.
In some embodiments, Ring A has an —$OCH_3$ substituent and a Cl substituent.
In some embodiments, Ring A has an —$OCH_3$ substituent and a Cl substituent with Cl at 2-position and —$OCH_3$ at 3-position.
In some embodiments, Ring A has an F substituent.
In some embodiments, Ring A has two F substituents.
In some embodiments, Ring A has two F substituents at same position.
In some embodiments, Ring A has two F substituents at 2- and 3-positions.
In some embodiments, Ring A has an F substituent and a Cl substituent.
In some embodiments, Ring A has an F substituent and a Cl substituent with Cl at 2-position and F at 3-position.
In some embodiments, Ring A has an acetyl substituent.
In some embodiments, Ring A has a $CH_3$ substituent.
In some embodiments, Ring A has two $CH_3$ substituents that are at same position.
In some embodiments, Ring A has a $CH_3$ substituent and a Cl substituent.
In some embodiments, Ring A has a $CH_3$ substituent and a Cl substituent with Cl at 2-position and $CH_3$ at 4-position.
In some embodiments, Ring A has a $CH_3$ substituent and a Cl substituent with Cl at 2-position and $CH_3$ at 3-position.
In some embodiments, Ring A has a $CH_3$ substituent and two F substituents.
In some embodiments, Ring A has a $CH_3$ substituent and two F substituents with two F at same position.
In some embodiments, Ring A has an OH substituent.
In some embodiments, Ring A has an OH substituent and a Cl substituent.
In some embodiments, Ring A has multiple substituents with any combination of the above substituents.

With respect to Formula 1, in some embodiments Ring B is: optionally substituted 6-oxo-5-(piperidin-1-yl)-1,6-dihydropyrazin-2-yl, optionally substituted 6-oxo-5-(pyrrolidin-1-yl)-1,6-dihydropyrazin-2-yl, optionally substituted 5-(hexahydropyrrolo[3,4-c]pyrrol-2(1H)-yl)-6-oxo-1,6-dihydropyrazin-2-yl, optionally substituted 5-(3,6-diazabicyclo[3.2.0]heptan-6-yl)-6-oxo-1,6-dihydropyrazin-2-yl, optionally substituted 6-oxo-5-(2-oxa-8-azaspiro[4.5]decan-8-yl)-1,6-dihydropyrazin-2-yl, optionally substituted 6-oxo-5-(piperidin-4-ylamino)-1,6-dihydropyrazin-2-yl, 6-oxo-5-(spiro[bicyclo[3.1.0]hexane-3,4'-piperidin]-1'-yl)-1,6-dihydropyrazin-2-yl, optionally substituted 6-oxo-5-(8-azaspiro[4.5]decan-8-yl)-1,6-dihydropyrazin-2-yl, optionally substituted 4-oxo-6-(piperidin-1-yl)-4,5-dihydro-1H-pyrazolo[3,4-d]pyrimidin-3-yl, 4-oxo-6-(pyrrolidin-1-yl)-4,5-dihydro-1H-pyrazolo[3,4-d]pyrimidin-3-yl, optionally substituted 4-oxo-2-(piperidin-1-yl)-3,4-dihydroquinazolin-5-yl, optionally substituted 4-oxo-2-(piperidin-1-yl)-3,4-dihydropyrido[3,4-d]pyrimidin-5-yl, optionally substituted 7-oxo-2-(piperidin-1-yl)-7,8-dihydropyrido[2,3-d]pyrimidin-5-yl, optionally substituted 5-(piperidin-1-yl)-1H-pyrazolo[4,3-d]thiazol-3-yl, optionally substituted 7-oxo-6-(piperidin-4-yl)-6,7-dihydro-1H-pyrazolo[4,3-d]pyrimidin-3-yl, optionally substituted 6-oxo-8-(piperidin-1-yl)-6,7-dihydro-1H-purin-2-yl, optionally substituted 8-(piperidin-1-yl)-7H-purin-2-yl, optionally substituted 6-oxo-2-(pyrrolidin-1-yl)-1,6-dihydropyrimidin-5-yl, optionally substituted 6-oxo-2-(piperidin-1-yl)-1,6-dihydropyrimidin-5-yl, optionally substituted 6-oxo-2-(2-oxa-8-azaspiro[4.5]decan-8-yl)-1,6-dihydropyrimidin-5-yl, optionally substituted 2-(3,6-diazabicyclo[3.2.0]heptan-6-yl)-6-oxo-1,6-dihydropyrimidin-5-yl, optionally substituted 2-(hexahydropyrrolo[3,4-c]pyrrol-2(1H)-yl)-6-oxo-1,6-dihydropyrimidin-5-yl, optionally substituted 2-(3-azabicyclo[3.2.0]heptan-3-yl)-6-oxo-1,6-dihydropyrimidin-5-yl, optionally substituted 6-oxo-2-(2-azaspiro[3.4]octan-2-yl)-1,6-dihydropyrimidin-5-yl, optionally substituted 2-(3-azabicyclo[3.1.0]hexan-3-yl)-6-oxo-1,6-dihydropyrimidin-5-yl, optionally substituted 6-oxo-2-(2-azaspiro[3.4]octan-2-yl)-1,6-dihydropyrimidin-5-yl, optionally substituted 5-oxo-6-(2-oxa-8-azaspiro[4.5]decan-8-yl)-4,5-dihydro-1H-pyrazolo[3,4-b]pyrazin-3-yl, optionally substituted 5-oxo-6-(piperidin-1-yl)-4,5-dihydro-1H-pyrazolo[3,4-b]pyrazin-3-yl, optionally substituted 6-(piperidin-1-yl)-1H-pyrazolo[3,4-d]pyrimidin-3-yl, optionally substituted 6-oxo-5-(2-azaspiro[3.4]octan-2-yl)-1,6-dihydropyrazin-2-yl, optionally substituted 1-cyclohexyl-2-oxo-1,2-dihydropyridin-4-yl, optionally substituted 5-(3-azabicyclo[3.1.0]hexan-3-yl)-6-oxo-1,6-dihydropyrazin-2-yl, optionally substituted 6-oxo-5-(3H-spiro[benzofuran-2,4'-piperidin]-1'-yl)-1,6-dihydropyrazin-2-yl, optionally substituted 4-oxo-2-(2-oxa-8-azaspiro[4.5]decan-8-yl)-4,7-dihydro-3H-pyrrolo[2,3-d]pyrimidin-5-yl, optionally substituted 5-(5,7-dihydrospiro[cyclopenta[b]pyridine-6,4'-piperidin]-1'-yl)-6-oxo-1,6-dihydropyrazin-2-yl, optionally substituted 5-(1,3-dihydrospiro[indene-2,4'-piperidin]-1'-yl)-6-oxo-1,6-dihydropyrazin-2-yl, optionally substituted 5-(4,6-dihydrospiro[cyclopenta[d]thiazole-5,4'-piperidin]-1'-yl)-6-oxo-1,6-dihydropyrazin-2-yl, or optionally substituted 6-oxo-5-(spiro[indoline-2,4'-piperidin]-1'-yl)-1,6-dihydropyrazin-2-yl. The core structures for some suitable Ring B groups are listed in Table 1A below.

TABLE 1A

| Structure | Name |
|---|---|
| 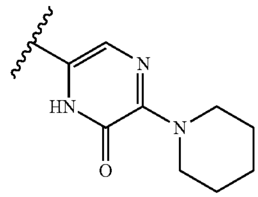 [SMILES: *c1cnc(N2CCCCC2)c(=O)[nH]1] | 6-oxo-5-(piperidin-1-yl)-1,6-dihydropyrazin-2-yl |
| 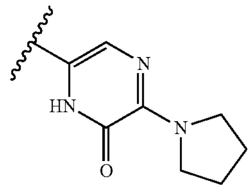 [SMILES: *c1cnc(N2CCCC2)c(=O)[nH]1] | 6-oxo-5-(pyrrolidin-1-yl)-1,6-dihydropyrazin-2-yl |
| 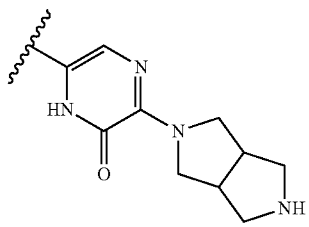 [SMILES: *c1cnc(N2CC3CNCC3C2)c(=O)[nH]1] | 5-(hexahydropyrrolo[3,4-c]pyrrol-2(1H)-yl)-6-oxo-1,6-dihydropyrazin-2-yl |
| 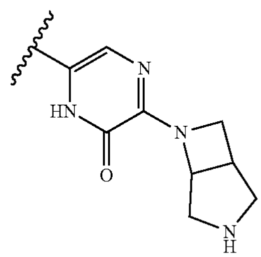 [SMILES: *c1cnc(N2CC3CNCC32)c(=O)[nH]1] | 5-(3,6-diazabicyclo[3.2.0]heptan-6-yl)-6-oxo-1,6-dihydropyrazin-2-yl |
| 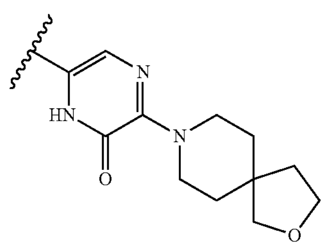 [SMILES: *c1cnc(N2CCC3(CCOC3)CC2)c(=O)[nH]1] | 6-oxo-5-(2-oxa-8-azaspiro[4.5]decan-8-yl)-1,6-dihydropyrazin-2-yl |
| 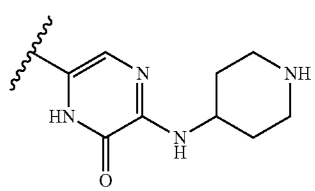 [SMILES: *c1cnc(NC2CCNCC2)c(=O)[nH]1] | 6-oxo-5-(piperidin-4-ylamino)-1,6-dihydropyrazin-2-yl |
| 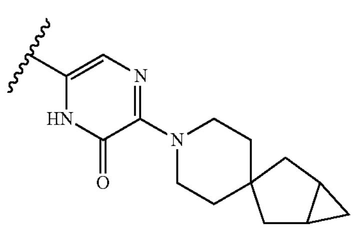 [SMILES: *c1cnc(N2CCC3(CC2)CC2CC2C3)c(=O)[nH]1] | 6-oxo-5-(spiro[bicyclo[3.1.0]hexane-3,4'-piperidin]-1'-yl)-1,6-dihydropyrazin-2-yl |

TABLE 1A-continued

| Structure | Name |
|---|---|
| 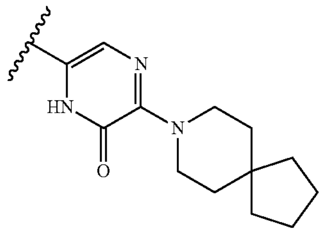 [SMILES: *c1cnc(N2CCC3(CCCC3)CC2)c(=O)[nH]1] | 6-oxo-5-(8-azaspiro[4.5]decan-8-yl)-1,6-dihydropyrazin-2-yl |
| 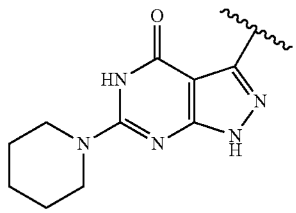 [SMILES: *c1n[nH]c2nc(N3CCCCC3)[nH]c(=O)c12] | 4-oxo-6-(piperidin-1-yl)-4,5-dihydro-1H-pyrazolo[3,4-d]pyrimidin-3-yl |
| 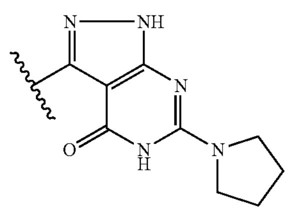 [SMILES: *c1n[nH]c2nc(N3CCCC3)[nH]c(=O)c12] | 4-oxo-6-(pyrrolidin-1-yl)-4,5-dihydro-1H-pyrazolo[3,4-d]pyrimidin-3-yl |
| 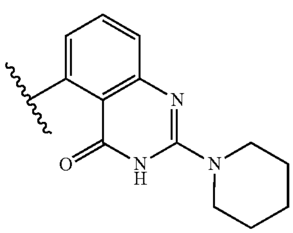 [SMILES: *c1cccc2nc(N3CCCCC3)[nH]c(=O)c12] | 4-oxo-2-(piperidin-1-yl)-3,4-dihydroquinazolin-5-yl |
| 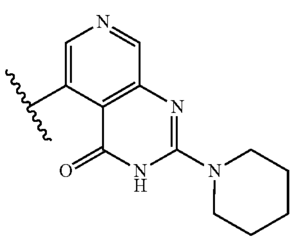 [SMILES: *c1cncc2nc(N3CCCCC3)[nH]c(=O)c12] | 4-oxo-2-(piperidin-1-yl)-3,4-dihydropyrido[3,4-d]pyrimidin-5-yl |
| 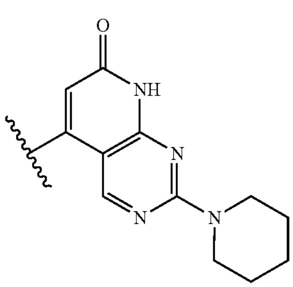 [SMILES: *c1cc(=O)[nH]c2nc(N3CCCCC3)ncc12] | 7-oxo-2-(piperidin-1-yl)-7,8-dihydropyrido[2,3-d]pyrimidin-5-yl |
| 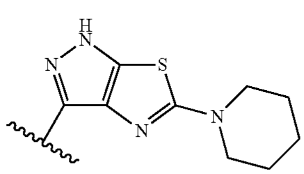 [SMILES: *c1n[nH]c2sc(N3CCCCC3)nc12] | 5-(piperidin-1-yl)-1H-pyrazolo[4,3-d]thiazol-3-yl |

TABLE 1A-continued

| Structure | Name |
|---|---|
| 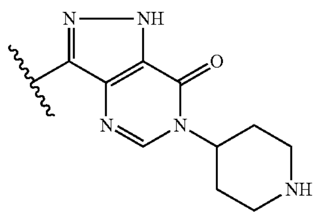 [SMILES: *c1n[nH]c2c(=O)n(C3CCNCC3)cnc12] | 7-oxo-6-(piperidin-4-yl)-6,7-dihydro-1H-pyrazolo[4,3-d]pyrimidin-3-yl |
| 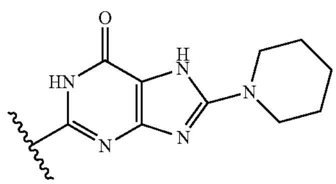 [SMILES: *c1nc2nc(N3CCCCC3)[nH]c2c(=O)[nH]1] | 6-oxo-8-(piperidin-1-yl)-6,7-dihydro-1H-purin-2-yl |
| 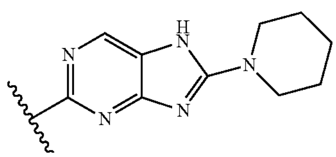 [SMILES: *c1ncc2[nH]c(N3CCCCC3)nc2n1] | 8-(piperidin-1-yl)-7H-purin-2-yl |
| 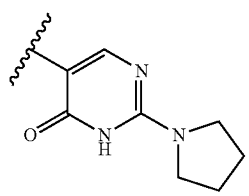 [SMILES: *c1cnc(N2CCCC2)[nH]c1=O] | 6-oxo-2-(pyrrolidin-1-yl)-1,6-dihydropyrimidin-5-yl |
| 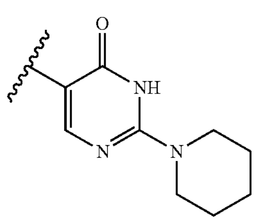 [SMILES: *c1cnc(N2CCCCC2)[nH]c1=O] | 6-oxo-2-(piperidin-1-yl)-1,6-dihydropyrimidin-5-yl |
| 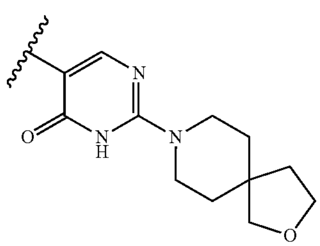 [SMILES: *c1cnc(N2CCC3(CCOC3)CC2)[nH]c1=O] | 6-oxo-2-(2-oxa-8-azaspiro[4.5]decan-8-yl)-1,6-dihydropyrimidin-5-yl |
| 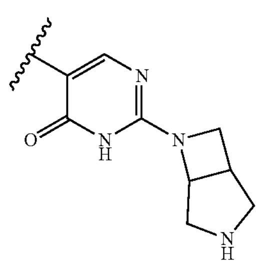 [SMILES: *c1cnc(N2CC3CNCC32)[nH]c1=O] | 2-(3,6-diazabicyclo[3.2.0]heptan-6-yl)-6-oxo-1,6-dihydropyrimidin-5-yl |

TABLE 1A-continued

| Structure | Name |
| --- | --- |
| 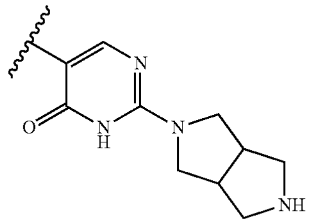 [SMILES: *c1cnc(N2CC3CNCC3C2)[nH]c1=O] | 2-(hexahydropyrrolo[3,4-c]pyrrol-2(1H)-yl)-6-oxo-1,6-dihydropyrimidin-5-yl |
| 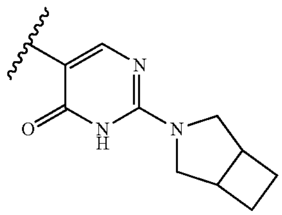 [SMILES: *c1cnc(N2CC3CCC3C2)[nH]c1=O] | 2-(3-azabicyclo[3.2.0]heptan-3-yl)-6-oxo-1,6-dihydropyrimidin-5-yl |
| | 6-oxo-2-(2-azaspiro[3.4]octan-2-yl)-1,6-dihydropyrimidin-5-yl |
| 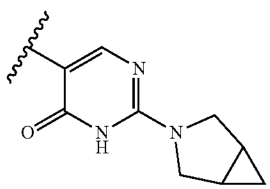 [SMILES: *c1cnc(N2CC3CC3C2)[nH]c1=O] | 2-(3-azabicyclo[3.1.0]hexan-3-yl)-6-oxo-1,6-dihydropyrimidin-5-yl |
| | 6-oxo-2-(2-azaspiro[3.4]octan-2-yl)-1,6-dihydropyrimidin-5-yl |
| 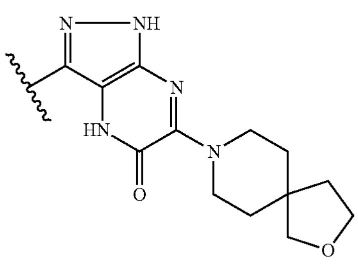 [SMILES: *c1n[nH]c2nc(N3CCC4(CCOC4)CC3)c(=O)[nH]c12] | 5-oxo-6-(2-oxa-8-azaspiro[4.5]decan-8-yl)-4,5-dihydro-1H-pyrazolo[3,4-b]pyrazin-3-yl |
| 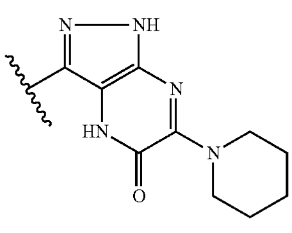 [SMILES: *c1n[nH]c2nc(N3CCCCC3)c(=O)[nH]c12] | 5-oxo-6-(piperidin-1-yl)-4,5-dihydro-1H-pyrazolo[3,4-b]pyrazin-3-yl |

TABLE 1A-continued

| Structure | Name |
|---|---|
| 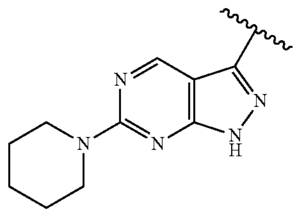 [SMILES: *c1n[nH]c2nc(N3CCCCC3)ncc12] | 6-(piperidin-1-yl)-1H-pyrazolo[3,4-d]pyrimidin-3-yl |
| 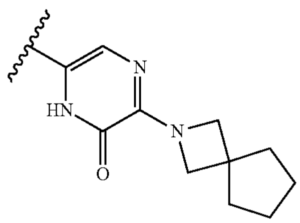 [SMILES: *c1cnc(N2CC3(CCCC3)C2)c(=O)[nH]1] | 6-oxo-5-(2-azaspiro[3.4]octan-2-yl)-1,6-dihydropyrazin-2-yl |
| 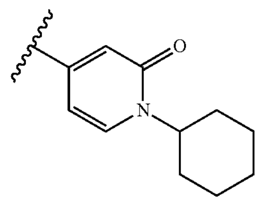 [SMILES: *c1ccn(C2CCCCC2)c(=O)c1] | 1-cyclohexyl-2-oxo-1,2-dihydropyridin-4-yl |
| 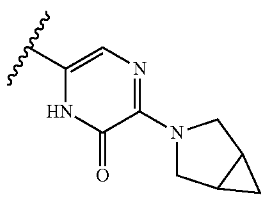 [SMILES: *c1cnc(N2CC3CC3C2)c(=O)[nH]1] | 5-(3-azabicyclo[3.1.0]hexan-3-yl)-6-oxo-1,6-dihydropyrazin-2-yl |
| 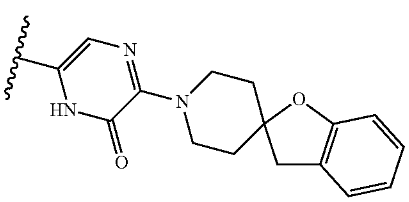 [SMILES: *c1cnc(N2CCC3(CC2)Cc2ccccc2O3)c(=O)[nH]1] | 6-oxo-5-(3H-spiro[benzofuran-2,4'-piperidin]-1'-yl)-1,6-dihydropyrazin-2-yl |
| 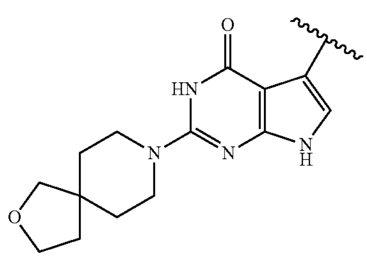 [SMILES: *c1c[nH]c2nc(N3CCC4(CCOC4)CC3)[nH]c(=O)c12] | 4-oxo-2-(2-oxa-8-azaspiro[4.5]decan-8-yl)-4,7-dihydro-3H-pyrrolo[2,3-d]pyrimidin-5-yl |
| 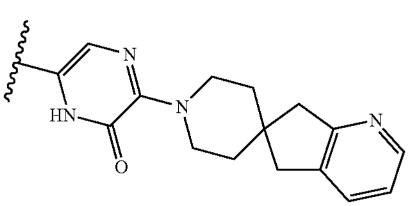 [SMILES: *c1cnc(N2CCC3(CC2)Cc2cccnc2C3)c(=O)[nH]1] | 5-(5,7-dihydrospiro[cyclopenta[b]pyridine-6,4'-piperidin]-1'-yl)-6-oxo-1,6-dihydropyrazin-2-yl |

TABLE 1A-continued

| Structure | Name |
|---|---|
| 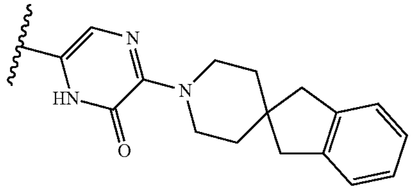 [SMILES: *c1cnc(N2CCC3(CC2)Cc2ccccc2C3)c(=O)[nH]1] | 5-(1,3-dihydrospiro[indene-2,4'-piperidin]-1'-yl)-6-oxo-1,6-dihydropyrazin-2-yl |
| 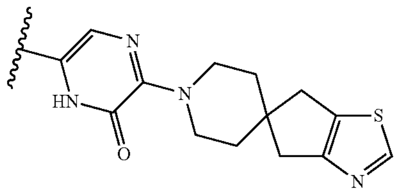 [SMILES: *c1cnc(N2CCC3(CC2)Cc2ncsc2C3)c(=O)[nH]1] | 5-(4,6-dihydrospiro[cyclopenta[d]thiazole-5,4'-piperidin]-1'-yl)-6-oxo-1,6-dihydropyrazin-2-yl |
| 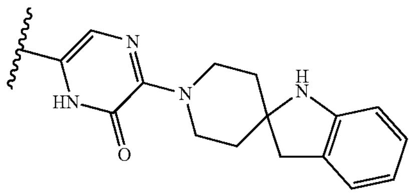 [SMILES: *c1cnc(N2CCC3(CC2)Cc2ccccc2N3)c(=O)[nH]1] | 6-oxo-5-(spiro[indoline-2,4'-piperidin]-1'-yl)-1,6-dihydropyrazin-2-yl |

In some embodiments, Ring B is unsubstituted.
In some embodiments, Ring B has a —CH$_3$ substituent.
In some embodiments, Ring B has a —CH$_2$NH$_2$ substituent.
In some embodiments, Ring B has a —NH$_2$ substituent.
In some embodiments, Ring B has a —CH$_2$CH$_2$NH$_2$ substituent.
In some embodiments, Ring B has a 1-aminopropan-2-yl substituent.
In some embodiments, Ring B has a —CN substituent.
In some embodiments, Ring B has an —F substituent.
In some embodiments, Ring B has a —Cl substituent.
In some embodiments, Ring B has a CH$_2$F substituent.
In some embodiments, Ring B has an —OH substituent.
In some embodiments, Ring B has an OCH$_3$ substituent.
In some embodiments, Ring B has multiple substituents with any combination of the above substituents.

With respect to Formula 1, in some embodiments, X is S, O, NR$^A$, CHR$^A$, SO, SO$_2$, CO, or a bond. In some embodiments, X is S. In some embodiments, X is a bond. In some embodiments, X is O. In some embodiments, X is NH. In some embodiments, X is CH(CH$_3$). In some embodiments, X is CH$_2$.

With respect to Formula 1, in some embodiments, R$^A$ is H or C$_{1-6}$ hydrocarbyl. In some embodiments, R$^A$ is H. In some embodiments, R$^A$ is CH$_3$.

In Appendix A below, various possibilities for Ring A are depicted. Ring A could be any core structure in any of these depicted possibilities, wherein these core structures are optionally substituted.

Appendix A

Phenyl,
2,3-dichlorophenyl,
naphthalen-1-yl,
2-(trifluoromethyl)phenyl,
2-(trifluoromethyl)pyridin-3-yl,
5-amino-2-chlorophenyl,
5-amino-2-chloropyridin-3-yl,
3-amino-2-chlorophenyl,
2-amino-3-chloropyridin-4-yl,
2-chloro-3-methoxyphenyl,
3-chloro-2-methoxypyridin-4-yl,
3-fluoro-1H-indol-4-yl,
3,3-difluoro-2-oxoindolin-4-yl,
1-acetyl-3,3-difluoroindolin-4-yl,
2-chloro-3-(4-hydroxy-1,5,5-trimethyl-2-oxo-2,5-dihydro-1H-pyrrole-3-carboxannido)phenyl,
2-chloro-3-(2-hydroxy-4-oxo-4H-pyrido[1,2-a]pyrimidine-3-carboxannido)phenyl,
2-chloro-3-(2-hydroxy-4-oxo-4H-pyrazino[1,2-a]pyrimidine-3-carboxannido)phenyl,
2-chloro-3-(7-hydroxy-5-oxo-5H-thiazolo[3,2-a]pyrimidine-6-carboxannido)phenyl,
2-chloro-3-(7-hydroxy-5-oxo-1,5-dihydroinnidazo[1,2-a]pyrimidine-6-carboxannido)phenyl,
2-chloro-3-(2-hydroxy-4-oxo-6,7,8,9-tetrahydro-4H-pyrido[1,2-a]pyrimidine-3-carboxannido)phenyl,
2,3-dichloropyridin-4-yl,
2,3-difluorophenyl,
3-chloro-2-fluoropyridin-4-yl,
2,3-difluoropyridin-4-yl,
2-chloro-3-methylphenyl,
3-chloro-2-methylpyridin-4-yl,
3,3-difluoro-1-methyl-2-oxoindolin-4-yl,
3-chloro-1-methyl-2-oxo-1,2-dihydropyridin-4-yl, or
2-chloro-3-fluorophenyl.

In Appendix B below, various possibilities for Ring B are depicted. Ring B could be any core structure in any of these depicted possibilities, wherein these core structures are optionally substituted.

Appendix B 5-(4-(aminomethyl)-4-methylpiperidin-1-yl)-6-oxo-1,6-dihydropyrazin-2-yl,
5-(3-(aminomethyl)-3-methylpyrrolidin-1-yl)-6-oxo-1,6-dihydropyrazin-2-yl, 5-(hexahydropyrrolo[3,4-c]pyrrol-2(1H)-yl)-6-oxo-1,6-dihydropyrazin-2-yl,
5-(3,6-diazabicyclo[3.2.0]heptan-6-yl)-6-oxo-1,6-dihydropyrazin-2-yl,
(S)-5-(4-amino-2-oxa-8-azaspiro[4.5]decan-8-yl)-6-oxo-1,6-dihydropyrazin-2-yl,
6-oxo-5-(piperidin-4-ylamino)-1,6-dihydropyrazin-2-yl,
5-(2-aminospiro[bicyclo[3.1.0]hexane-3,4'-piperidin]-1'-yl)-6-oxo-1,6-dihydropyrazin-2-yl,
5-((1R,3R)-1-amino-3-methyl-8-azaspiro[4.5]decan-8-yl)-6-oxo-1,6-dihydropyrazin-2-yl,
(6-(4-(aminomethyl)-4-methylpiperidin-1-yl)-4-oxo-4,5-dihydro-1H-pyrazolo[3,4-d]pyrimidin-3-yl)amino,
6-(3-(aminomethyl)-3-methylpyrrolidin-1-yl)-4-oxo-4,5-dihydro-1H-pyrazolo[3,4-d]pyrimidin-3-yl,
7-amino-2-(4-(aminomethyl)-4-methylpiperidin-1-yl)-4-oxo-3,4-dihydroquinazolin-5-yl,
2-(4-(aminomethyl)-4-methylpiperidin-1-yl)-4-oxo-3,4-dihydropyrido[3,4-d]pyrimidin-5-yl,
2-(4-(aminomethyl)-4-methylpiperidin-1-yl)-7-oxo-7,8-dihydropyrido[2,3-d]pyrimidin-5-yl,
5-(4-(aminomethyl)-4-methylpiperidin-1-yl)-1H-pyrazolo[4,3-d]thiazol-3-yl,
6-(1-(1-aminopropan-2-yl)piperidin-4-yl)-7-oxo-6,7-dihydro-1H-pyrazolo[4,3-d]pyrimidin-3-yl,
8-(4-(aminomethyl)-4-methylpiperidin-1-yl)-6-oxo-6,7-dihydro-1H-purin-2-yl,
6-amino-8-(4-(aminomethyl)-4-methylpiperidin-1-yl)-7H-purin-2-yl,
4-amino-2-(3-(aminomethyl)-3-methylpyrrolidin-1-yl)-6-oxo-1,6-dihydropyrimidin-5-yl,
2-(4-(aminomethyl)-4-methylpiperidin-1-yl)-4-cyano-1-methyl-6-oxo-1,6-dihydropyrimidin-5-yl,
4-amino-2-(4-amino-2-oxa-8-azaspiro[4.5]decan-8-yl)-6-oxo-1,6-dihydropyrimidin-5-yl,
4-amino-2-(3,6-diazabicyclo[3.2.0]heptan-6-yl)-6-oxo-1,6-dihydropyrimidin-5-yl,
4-amino-2-(hexahydropyrrolo[3,4-c]pyrrol-2(1H)-yl)-6-oxo-1,6-dihydropyrimidin-5-yl,
4-amino-2-(4-(aminomethyl)-4-methylpiperidin-1-yl)-6-oxo-1,6-dihydropyrimidin-5-yl,
4-amino-2-(6-amino-3-azabicyclo[3.2.0]heptan-3-yl)-6-oxo-1,6-dihydropyrimidin-5-yl,
4-amino-2-(6-amino-2-azaspiro[3.4]octan-2-yl)-1-methyl-6-oxo-1,6-dihydropyrimidin-5-yl,
4-amino-2-(6-amino-3-azabicyclo[3.1.0]hexan-3-yl)-6-oxo-1,6-dihydropyrimidin-5-yl,
4-amino-2-(6-amino-2-azaspiro[3.4]octan-2-yl)-6-oxo-1,6-dihydropyrimidin-5-yl,
5-(4-(aminomethyl)-4-methylpiperidin-1-yl)-1-methyl-6-oxo-1,6-dihydropyrazin-2-yl,
5-(4-amino-2-oxa-8-azaspiro[4.5]decan-8-yl)-6-oxo-1,6-dihydropyrazin-2-yl,
(S)-5-(4-amino-2-oxa-8-azaspiro[4.5]decan-8-yl)-1-methyl-6-oxo-1,6-dihydropyrazin-2-yl,
5-(2-aminospiro[bicyclo[3.1.0]hexane-3,4'-piperidin]-1'-yl)-1-methyl-6-oxo-1,6-dihydropyrazin-2-yl,
5-((3S,4S)-4-amino-3-methyl-2-oxa-8-azaspiro[4.5]decan-8-yl)-6-oxo-1,6-dihydropyrazin-2-yl,
5-((3S,4S)-4-amino-3-methyl-2-oxa-8-azaspiro[4.5]decan-8-yl)-1-methyl-6-oxo-1,6-dihydropyrazin-2-yl,
5-((1R,3R)-1-amino-3-methyl-8-azaspiro[4.5]decan-8-yl)-1-methyl-6-oxo-1,6-dihydropyrazin-2-yl,
5-(4-(aminomethyl)-4-methylpiperidin-1-yl)-6-oxo-1,6-dihydropyrazin-2-yl,
6-(4-(aminomethyl)-4-methylpiperidin-1-yl)-4-oxo-4,5-dihydro-1H-pyrazolo[3,4-d]pyrimidin-3-yl,
6-(4-(aminomethyl)-4-methylpiperidin-1-yl)-4-methyl-5-oxo-4,5-dihydro-1H-pyrazolo[3,4-b]pyrazin-3-yl,
6-(4-(aminomethyl)-4-methylpiperidin-1-yl)-5-oxo-4,5-dihydro-1H-pyrazolo[3,4-b]pyrazin-3-yl,
6-(3-(aminomethyl)-3-methylpyrrolidin-1-yl)-5-methyl-4-oxo-4,5-dihydro-1H-pyrazolo[3,4-d]pyrimidin-3-yl,
6-(4-(aminomethyl)-4-methylpiperidin-1-yl)-5-methyl-4-oxo-4,5-dihydro-1H-pyrazolo[3,4-d]pyrimidin-3-yl,
6-(4-(aminomethyl)-4-methylpiperidin-1-yl)-1H-pyrazolo[3,4-d]pyrimidin-3-yl,
4-amino-2-(hexahydropyrrolo[3,4-c]pyrrol-2(1H)-yl)-1-methyl-6-oxo-1,6-dihydropyrimidin-5-yl,
4-amino-2-((3S,4S)-4-amino-3-methyl-2-oxa-8-azaspiro[4.5]decan-8-yl)-6-oxo-1,6-dihydropyrimidin-5-yl,
4-amino-2-((3S,4S)-4-amino-3-methyl-2-oxa-8-azaspiro[4.5]decan-8-yl)-1-methyl-6-oxo-1,6-dihydropyrimidin-5-yl,
4-amino-2-(6-amino-3-azabicyclo[3.1.0]hexan-3-yl)-1-methyl-6-oxo-1,6-dihydropyrimidin-5-yl,
4-amino-2-(6-amino-3-azabicyclo[3.2.0]heptan-3-yl)-1-methyl-6-oxo-1,6-dihydropyrimidin-5-yl,
5-(4-(aminomethyl)-4-fluoropiperidin-1-yl)-6-oxo-1,6-dihydropyrazin-2-yl,
5-(4-(aminomethyl)-4-hydroxypiperidin-1-yl)-6-oxo-1,6-dihydropyrazin-2-yl,
(R)-5-(6-amino-2-azaspiro[3.4]octan-2-yl)-6-oxo-1,6-dihydropyrazin-2-yl,
(S)-5-(6-amino-2-azaspiro[3.4]octan-2-yl)-6-oxo-1,6-dihydropyrazin-2-yl,
1-(3-aminocyclohexyl)-2-oxo-1,2-dihydropyridin-4-yl,
(R)-5-(4-amino-2-oxa-8-azaspiro[4.5]decan-8-yl)-6-oxo-1,6-dihydropyrazin-2-yl,
5-(4-amino-4-(fluoromethyl)piperidin-1-yl)-6-oxo-1,6-dihydropyrazin-2-yl,
5-((3S,4S)-4-amino-3-methyl-2-oxa-8-azaspiro[4.5]decan-8-yl)-6-oxo-1,6-dihydropyrazin-2-yl,
(R)-5-(1-amino-8-azaspiro[4.5]decan-8-yl)-6-oxo-1,6-dihydropyrazin-2-yl,
5-(6-amino-3-azabicyclo[3.1.0]hexan-3-yl)-6-oxo-1,6-dihydropyrazin-2-yl,
(R)-5-(3-amino-3H-spiro[benzofuran-2,4'-piperidin]-1'-yl)-6-oxo-1,6-dihydropyrazin-2-yl,
2-((3S,4S)-4-amino-3-methyl-2-oxa-8-azaspiro[4.5]decan-8-yl)-3-methyl-4-oxo-4,7-dihydro-3H-pyrrolo[2,3-d]pyrimidin-5-yl,
2-((3S,4S)-4-amino-3-methyl-2-oxa-8-azaspiro[4.5]decan-8-yl)-4-oxo-4,7-dihydro-3H-pyrrolo[2,3-d]pyrimidin-5-yl,
(R)-5-(1-amino-3,3-difluoro-8-azaspiro[4.5]decan-8-yl)-6-oxo-1,6-dihydropyrazin-2-yl,
5-((1R)-1-amino-3-fluoro-8-azaspiro[4.5]decan-8-yl)-6-oxo-1,6-dihydropyrazin-2-yl,
(S)-5-(5-amino-5,7-dihydrospiro[cyclopenta[b]pyridine-6,4'-piperidin]-1'-yl)-6-oxo-1,6-dihydropyrazin-2-yl,
(S)-5-(1-amino-1,3-dihydrospiro[indene-2,4'-piperidin]-1'-yl)-6-oxo-1,6-dihydropyrazin-2-yl,
(S)-5-(4-amino-2-chloro-4,6-dihydrospiro[cyclopenta[d]thiazole-5,4'-piperidin]-1'-yl)-6-oxo-1,6-dihydropyrazin-2-yl,
(R)-5-(3-aminospiro[indoline-2,4'-piperidin]-1'-yl)-6-oxo-1,6-dihydropyrazin-2-yl, or
(S)-5-(1-amino-4-methoxy-1,3-dihydrospiro[indene-2,4'-piperidin]-1'-yl)-6-oxo-1,6-dihydropyrazin-2-yl.

Some embodiments include one of the compounds in Table 1, wherein any of the compounds in Table 1 below may be optionally substituted.

TABLE 1

| Compound ID | Structure | Compound name |
|---|---|---|
| 1 | 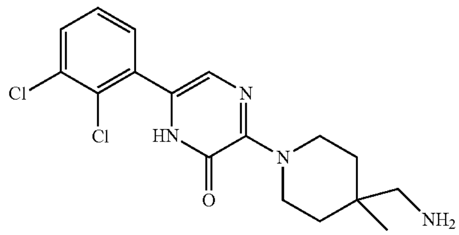 [SMILES: CC1(CN)CCN(c2ncc(-c3cccc(Cl)c3Cl)[nH]c2=O)CC1] | 3-(4-(aminomethyl)-4-methylpiperidin-1-yl)-6-(2,3-dichlorophenyl)pyrazin-2(1H)-one |
| 2 | 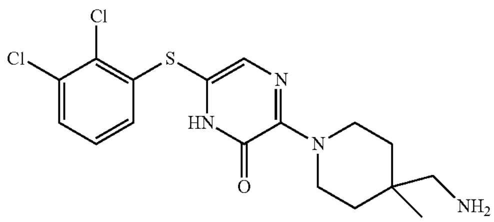 [SMILES: CC1(CN)CCN(c2ncc(Sc3cccc(Cl)c3Cl)[nH]c2=O)CC1] | 3-(4-(aminomethyl)-4-methylpiperidin-1-yl)-6-((2,3-dichlorophenyl)thio)pyrazin-2(1H)-one |
| 3 | 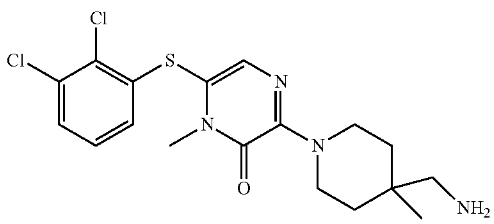 [SMILES: Cn1c(Sc2cccc(Cl)c2Cl)cnc(N2CCC(C)(CN)CC2)c1=O] | 3-(4-(aminomethyl)-4-methylpiperidin-1-yl)-6-((2,3-dichlorophenyl)thio)-1-methylpyrazin-2(1H)-one |
| 4 | 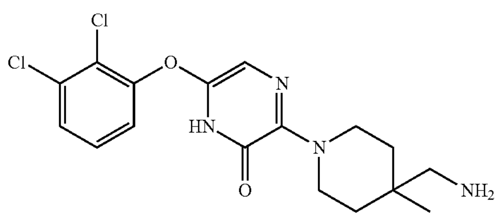 [SMILES: CC1(CN)CCN(c2ncc(Oc3cccc(Cl)c3Cl)[nH]c2=O)CC1] | 3-(4-(aminomethyl)-4-methylpiperidin-1-yl)-6-(2,3-dichlorophenoxy)pyrazin-2(1H)-one |
| 5 | 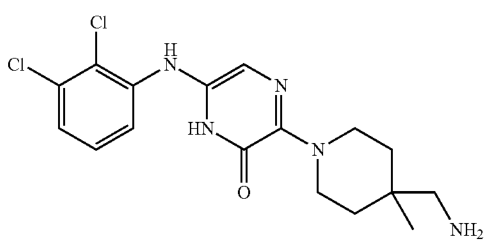 [SMILES: CC1(CN)CCN(c2ncc(Nc3cccc(Cl)c3Cl)[nH]c2=O)CC1] | 3-(4-(aminomethyl)-4-methylpiperidin-1-yl)-6-((2,3-dichlorophenyl)amino)pyrazin-2(1H)-one |
| 6 | 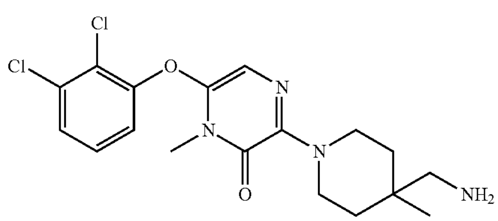 [SMILES: Cn1c(Oc2cccc(Cl)c2Cl)cnc(N2CCC(C)(CN)CC2)c1=O] | 3-(4-(aminomethyl)-4-methylpiperidin-1-yl)-6-(2,3-dichlorophenoxy)-1-methylpyrazin-2(1H)-one |
| 7 | 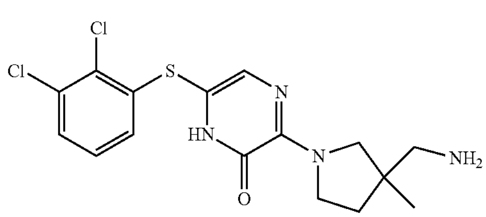 [SMILES: CC1(CN)CCN(c2ncc(Sc3cccc(Cl)c3Cl)[nH]c2=O)C1] | 3-(3-(aminomethyl)-3-methylpyrrolidin-1-yl)-6-((2,3-dichlorophenyl)thio)pyrazin-2(1H)-one |

TABLE 1-continued

| Compound ID | Structure | Compound name |
|---|---|---|
| 8 | 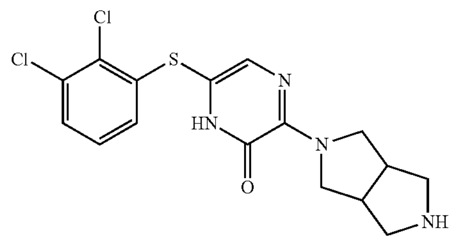 [SMILES: O=c1[nH]c(Sc2cccc(Cl)c2Cl)cnc1N1CC2CNCC2C1] | 6-((2,3-dichlorophenyl)thio)-3-(hexahydropyrrolo[3,4-c]pyrrol-2(1H)-yl)pyrazin-2(1H)-one |
| 9 | 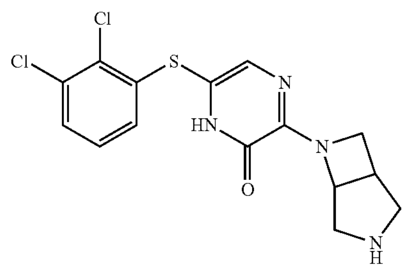 [SMILES: O=c1[nH]c(Sc2cccc(Cl)c2Cl)cnc1N1CC2CNCC21] | 3-(3,6-diazabicyclo[3.2.0]heptan-6-yl)-6-((2,3-dichlorophenyl)thio)pyrazin-2(1H)-one |
| 10 | 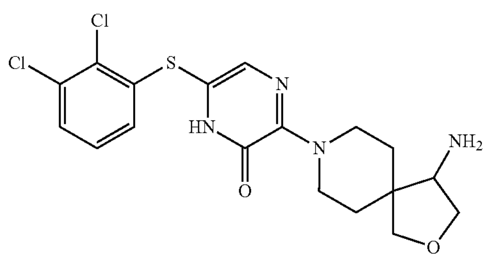 [SMILES: NC1COCC12CCN(c1ncc(Sc3cccc(Cl)c3Cl)[nH]c1=O)CC2] | 3-(4-amino-2-oxa-8-azaspiro[4.5]decan-8-yl)-6-((2,3-dichlorophenyl)thio)pyrazin-2(1H)-one |
| 11 | 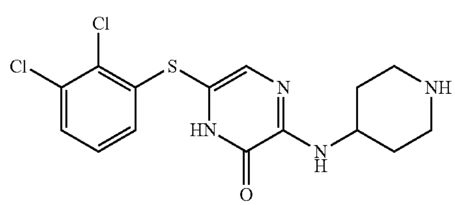 [SMILES: O=c1[nH]c(Sc2cccc(Cl)c2Cl)cnc1NC1CCNCC1] | 6-((2,3-dichlorophenyl)thio)-3-(piperidin-4-ylamino)pyrazin-2(1H)-one |
| 12 | 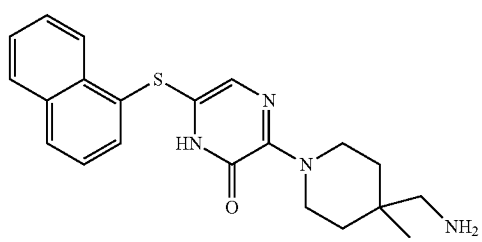 [SMILES: CC1(CN)CCN(c2ncc(Sc3cccc4ccccc34)[nH]c2=O)CC1] | 3-(4-(aminomethyl)-4-methylpiperidin-1-yl)-6-(naphthalen-1-ylthio)pyrazin-2(1H)-one |
| 13 | 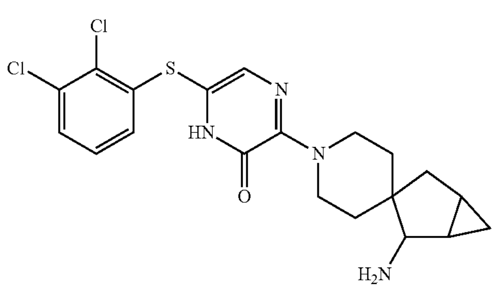 [SMILES: NC1C2CC2CC12CCN(c1ncc(Sc3cccc(Cl)c3Cl)[nH]c1=O)CC2] | 3-(2-aminospiro[bicyclo[3.1.0]hexane-3,4'-piperidin]-1'-yl)-6-((2,3-dichlorophenyl)thio)pyrazin-2(1H)-one |

TABLE 1-continued

| Compound ID | Structure | Compound name |
|---|---|---|
| 14 | 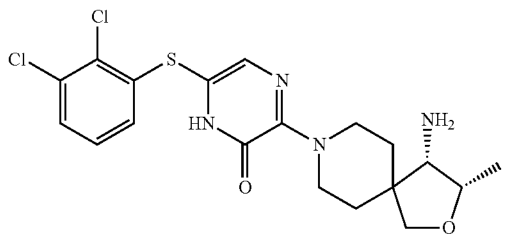 [SMILES: C[C@@H]1OCC2(CCN(c3ncc(Sc4cccc(Cl)c4Cl)[nH]c3=O)CC2)[C@@H]1N] | 3-((3S,4S)-4-amino-3-methyl-2-oxa-8-azaspiro[4.5]decan-8-yl)-6-((2,3-dichlorophenyl)thio)pyrazin-2(1H)-one |
| 15 | 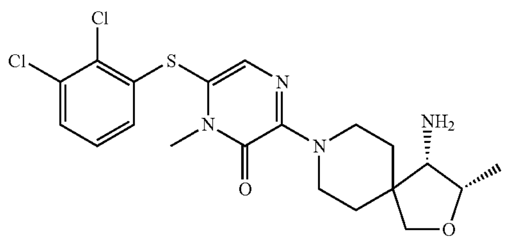 [SMILES: C[C@@H]1OCC2(CCN(c3ncc(Sc4cccc(Cl)c4Cl)n(C)c3=O)CC2)[C@@H]1N] | 3-((3S,4S)-4-amino-3-methyl-2-oxa-8-azaspiro[4.5]decan-8-yl)-6-((2,3-dichlorophenyl)thio)-1-methylpyrazin-2(1H)-one |
| 16 | 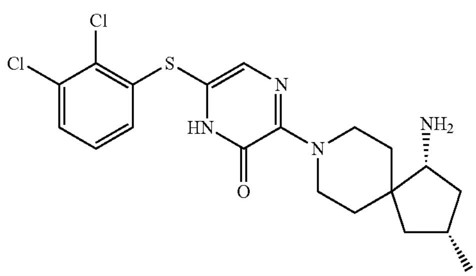 [SMILES: C[C@H]1C[C@@H](N)C2(CCN(c3ncc(Sc4cccc(Cl)c4Cl)[nH]c3=O)CC2)C1] | 3-((1R,3R)-1-amino-3-methyl-8-azaspiro[4.5]decan-8-yl)-6-((2,3-dichlorophenyl)thio)pyrazin-2(1H)-one |
| 17 | 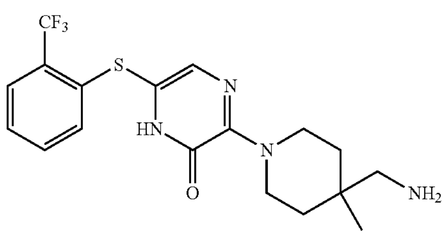 [SMILES: CC1(CN)CCN(c2ncc(Sc3ccccc3C(F)(F)F)[nH]c2=O)CC1] | 3-(4-(aminomethyl)-4-methylpiperidin-1-yl)-6-((2-(trifluoromethyl)phenyl)thio)pyrazin-2(1H)-one |
| 18 | 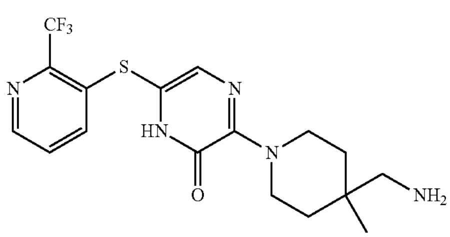 [SMILES: CC1(CN)CCN(c2ncc(Sc3cccnc3C(F)(F)F)[nH]c2=O)CC1] | 3-(4-(aminomethyl)-4-methylpiperidin-1-yl)-6-((2-(trifluoromethyl)pyridin-3-yl)thio)pyrazin-2(1H)-one |
| 19 | 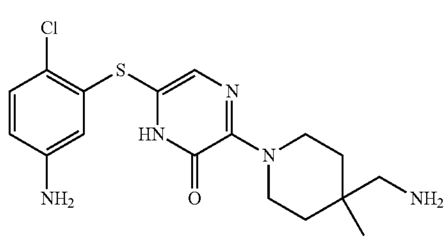 [SMILES: CC1(CN)CCN(c2ncc(Sc3cc(N)ccc3Cl)[nH]c2=O)CC1] | 6-((5-amino-2-chlorophenyl)thio)-3-(4-(aminomethyl)-4-methylpiperidin-1-yl)pyrazin-2(1H)-one |

TABLE 1-continued

| Compound ID | Structure | Compound name |
|---|---|---|
| 20 | 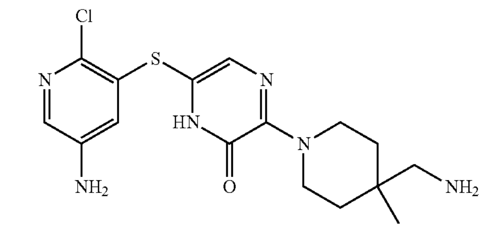 [SMILES: CC1(CN)CCN(c2ncc(Sc3cc(N)cnc3Cl)[nH]c2=O)CC1] | 6-((5-amino-2-chloropyridin-3-yl)thio)-3-(4-(aminomethyl)-4-methylpiperidin-1-yl)pyrazin-2(1H)-one |
| 21 | 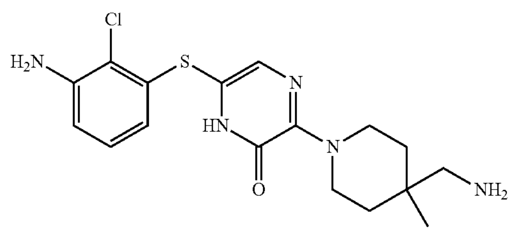 | 6-((3-amino-2-chlorophenyl)thio)-3-(4-(aminomethyl)-4-methylpiperidin-1-yl)pyrazin-2(1H)-one |
| 22 | 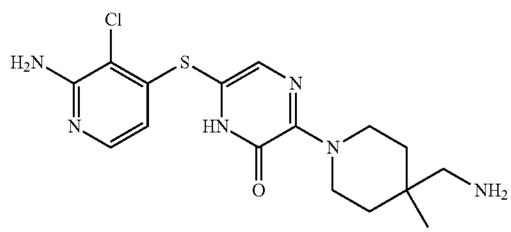 [SMILES: CC1(CN)CCN(c2ncc(Sc3ccnc(N)c3Cl)[nH]c2=O)CC1] | 6-((2-amino-3-chloropyridin-4-yl)thio)-3-(4-(aminomethyl)-4-methylpiperidin-1-yl)pyrazin-2(1H)-one |
| 23 | 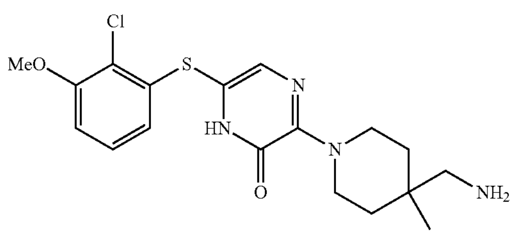 [SMILES: COc1cccc(Sc2cnc(N3CCC(C)(CN)CC3)c(=O)[nH]2)c1Cl] | 3-(4-(aminomethyl)-4-methylpiperidin-1-yl)-6-((2-chloro-3-methoxyphenyl)thio)pyrazin-2(1H)-one |
| 24 | 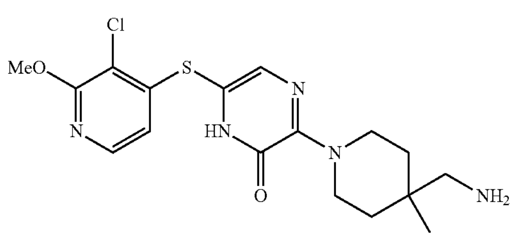 | 3-(4-(aminomethyl)-4-methylpiperidin-1-yl)-6-((3-chloro-2-methoxypyridin-4-yl)thio)pyrazin-2(1H)-one |
| 25 | 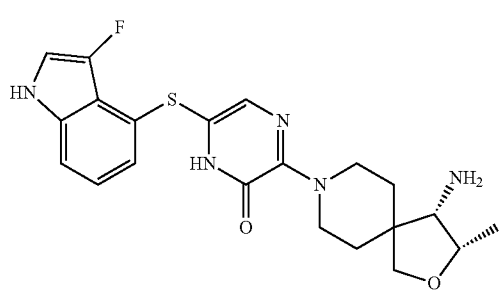 [SMILES: C[C@@H]1OCC2(CCN(c3ncc(Sc4cccc5[nH]cc(F)c45)[nH]c3=O)CC2)[C@@H]1N] | 3-((3S,4S)-4-amino-3-methyl-2-oxa-8-azaspiro[4.5]decan-8-yl)-6-((3-fluoro-1H-indol-4-yl)thio)pyrazin-2(1H)-one |

TABLE 1-continued

| Compound ID | Structure | Compound name |
|---|---|---|
| 26 | 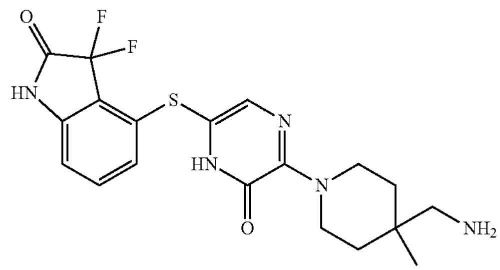 [SMILES: CC1(CN)CCN(c2ncc(Sc3cccc4c3C(F)(F)C(=O)N4)[nH]c2=O)CC1] | 4-((5-(4-(aminomethyl)-4-methylpiperidin-1-yl)-6-oxo-1,6-dihydropyrazin-2-yl)thio)-3,3-difluoroindolin-2-one |
| 27 | 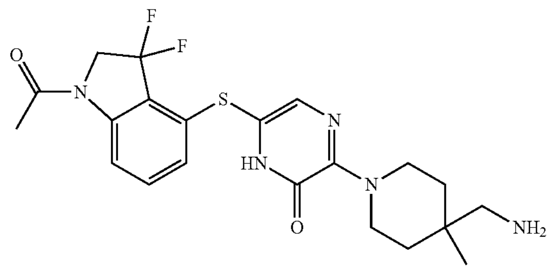 [SMILES: CC(=O)N1CC(F)(F)c2c(Sc3cnc(N4CCC(C)(CN)CC4)c(=O)[nH]3)cccc21] | 6-((1-acetyl-3,3-difluoroindolin-4-yl)thio)-3-(4-(aminomethyl)-4-methylpiperidin-1-yl)pyrazin-2(1H)-one |
| 28 | 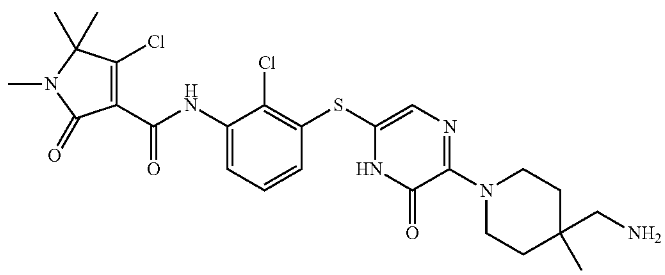 [SMILES: CN1C(=O)C(C(=O)Nc2cccc(Sc3cnc(N4CCC(C)(CN)CC4)c(=O)[nH]3)c2Cl)=C(Cl)C1(C)C] | N-(3-((5-(4-(aminomethyl)-4-methylpiperidin-1-yl)-6-oxo-1,6-dihydropyrazin-2-yl)thio)-2-chlorophenyl)-4-hydroxy-1,5,5-trimethyl-2-oxo-2,5-dihydro-1H-pyrrole-3-carboxamide |
| 29 | 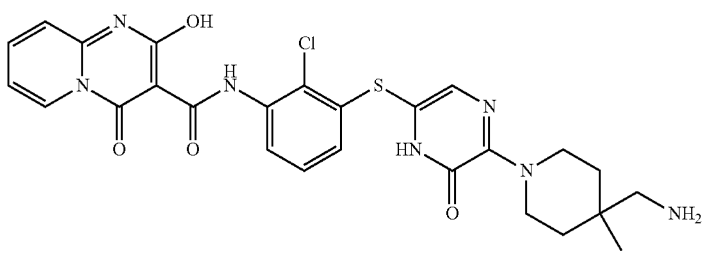 [SMILES: CC1(CN)CCN(c2ncc(Sc3cccc(NC(=O)c4c(O)nc5ccccn5c4=O)c3Cl)[nH]c2=O)CC1] | N-(3-((5-(4-(aminomethyl)-4-methylpiperidin-1-yl)-6-oxo-1,6-dihydropyrazin-2-yl)thio)-2-chlorophenyl)-2-hydroxy-4-oxo-4H-pyrido[1,2-a]pyrimidine-3-carboxamide |
| 30 | 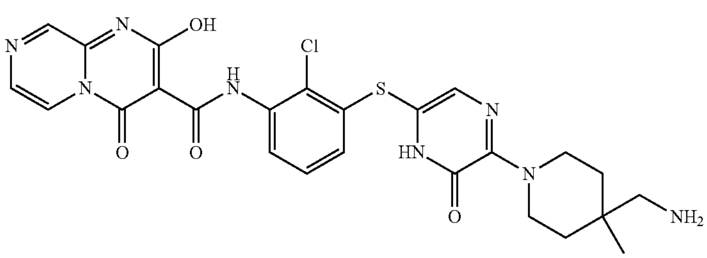 [SMILES: CC1(CN)CCN(c2ncc(Sc3cccc(NC(=O)c4c(O)nc5cnccn5c4=O)c3Cl)[nH]c2=O)CC1] | N-(3-((5-(4-(aminomethyl)-4-methylpiperidin-1-yl)-6-oxo-1,6-dihydropyrazin-2-yl)thio)-2-chlorophenyl)-2-hydroxy-4-oxo-4H-pyrazino[1,2-a]pyrimidine-3-carboxamide |
| 31 | 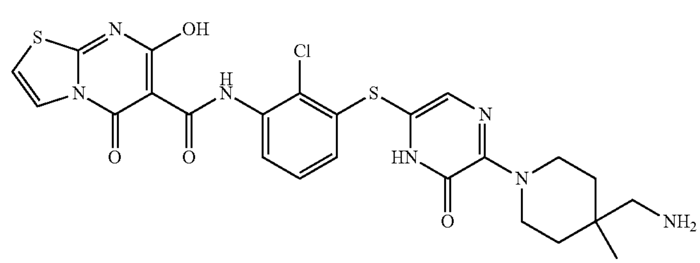 [SMILES: CC1(CN)CCN(c2ncc(Sc3cccc(NC(=O)c4c(O)nc5sccn5c4=O)c3Cl)[nH]c2=O)CC1] | N-(3-((5-(4-(aminomethyl)-4-methylpiperidin-1-yl)-6-oxo-1,6-dihydropyrazin-2-yl)thio)-2-chlorophenyl)-7-hydroxy-5-oxo-5H-thiazolo[3,2-a]pyrimidine-6-carboxamide |

TABLE 1-continued

| Compound ID | Structure | Compound name |
|---|---|---|
| 32 | 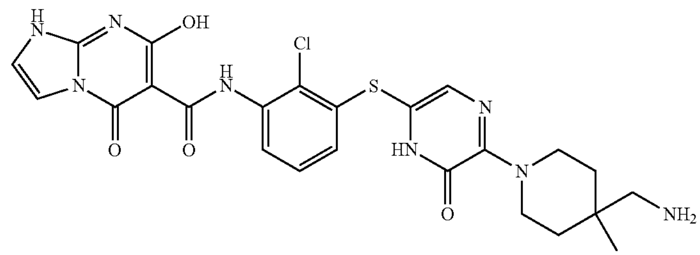 [SMILES: CC1(CN)CCN(c2ncc(Sc3cccc(NC(=O)c4c(O)nc5[nH]ccn5c4=O)c3Cl)[nH]c2=O)CC1] | N-(3-((5-(4-(aminomethyl)-4-methylpiperidin-1-yl)-6-oxo-1,6-dihydropyrazin-2-yl)thio)-2-chlorophenyl)-7-hydroxy-5-oxo-1,5-dihydroimidazo[1,2-a]pyrimidine-6-carboxamide |
| 33 | 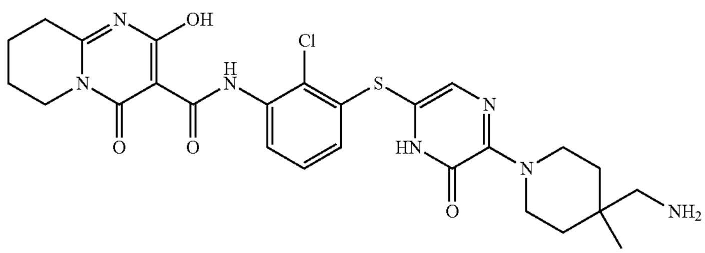 [SMILES: CC1(CN)CCN(c2ncc(Sc3cccc(NC(=O)c4c(O)nc5n(c4=O)CCCC5)c3Cl)[nH]c2=O)CC1] | N-(3-((5-(4-(aminomethyl)-4-methylpiperidin-1-yl)-6-oxo-1,6-dihydropyrazin-2-yl)thio)-2-chlorophenyl)-2-hydroxy-4-oxo-6,7,8,9-tetrahydro-4H-pyrido[1,2-a]pyrimidine-3-carboxamide |
| 34 | 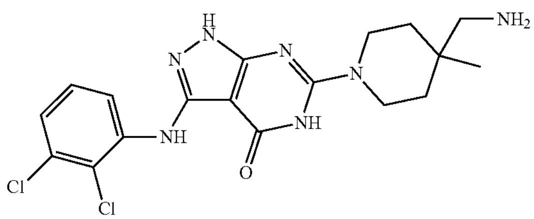 [SMILES: CC1(CN)CCN(c2nc3[nH]nc(Nc4cccc(Cl)c4Cl)c3c(=O)[nH]2)CC1] | 6-(4-(aminomethyl)-4-methylpiperidin-1-yl)-3-((2,3-dichlorophenyl)amino)-1,5-dihydro-4H-pyrazolo[3,4-d]pyrimidin-4-one |
| 35 | 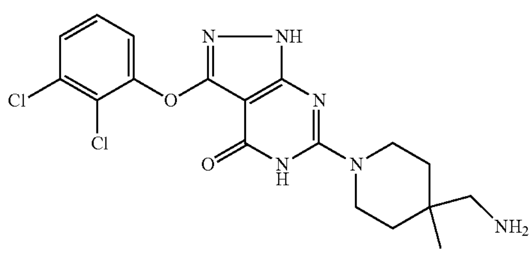 [SMILES: CC1(CN)CCN(c2nc3[nH]nc(Oc4cccc(Cl)c4Cl)c3c(=O)[nH]2)CC1] | 6-(4-(aminomethyl)-4-methylpiperidin-1-yl)-3-(2,3-dichlorophenoxy)-1,5-dihydro-4H-pyrazolo[3,4-d]pyrimidin-4-one |
| 36 | 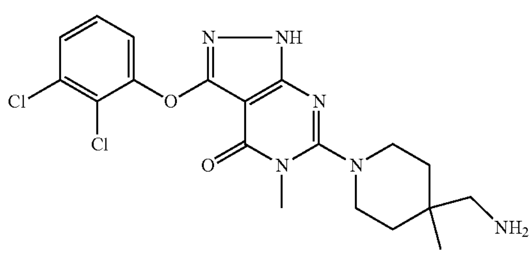 [SMILES: Cn1c(N2CCC(C)(CN)CC2)nc2[nH]nc(Oc3cccc(Cl)c3Cl)c2c1=O] | 6-(4-(aminomethyl)-4-methylpiperidin-1-yl)-3-((2,3-dichlorophenyl)amino)-5-methyl-1,5-dihydro-4H-pyrazolo[3,4-d]pyrimidin-4-one |
| 37 | 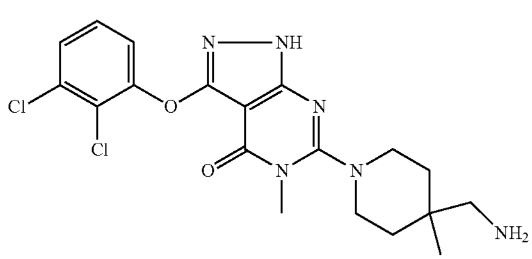 [SMILES: Cn1c(N2CCC(C)(CN)CC2)nc2[nH]nc(Oc3cccc(Cl)c3Cl)c2c1=O] | 6-(4-(aminomethyl)-4-methylpiperidin-1-yl)-3-(2,3-dichlorophenoxy)-5-methyl-1,5-dihydro-4H-pyrazolo[3,4-d]pyrimidin-4-one |

TABLE 1-continued

| Compound ID | Structure | Compound name |
|---|---|---|
| 38 | 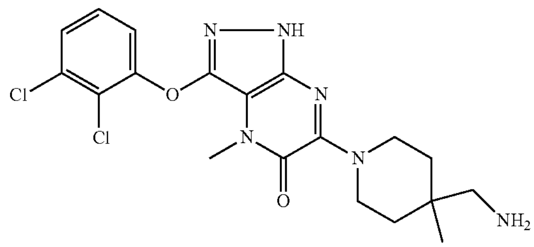 [SMILES: Cn1c(=O)c(N2CCC(C)(CN)CC2)nc2[nH]nc(Oc3cccc(Cl)c3Cl)c21] | 6-(4-(aminomethyl)-4-methylpiperidin-1-yl)-3-(2,3-dichlorophenoxy)-4-methyl-1,4-dihydro-5H-pyrazolo[3,4-b]pyrazin-5-one |
| 39 | 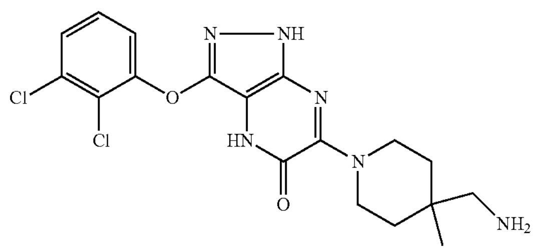 [SMILES: CC1(CN)CCN(c2nc3[nH]nc(Oc4cccc(Cl)c4Cl)c3[nH]c2=O)CC1] | 6-(4-(aminomethyl)-4-methylpiperidin-1-yl)-3-(2,3-dichlorophenoxy)-1,4-dihydro-5H-pyrazolo[3,4-b]pyrazin-5-one |
| 40 | 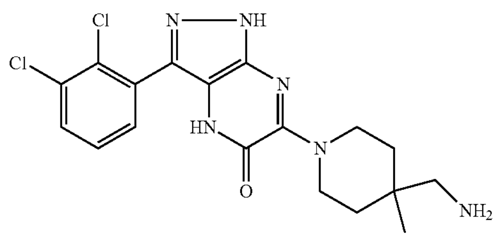 [SMILES: CC1(CN)CCN(c2nc3[nH]nc(-c4cccc(Cl)c4Cl)c3[nH]c2=O)CC1] | 6-(4-(aminomethyl)-4-methylpiperidin-1-yl)-3-(2,3-dichlorophenyl)-1,4-dihydro-5H-pyrazolo[3,4-b]pyrazin-5-one |
| 41 | 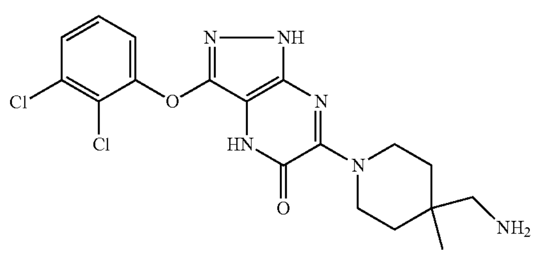 [SMILES: CC1(CN)CCN(c2nc3[nH]nc(Oc4cccc(Cl)c4Cl)c3[nH]c2=O)CC1] | 6-(4-(aminomethyl)-4-methylpiperidin-1-yl)-3-((2,3-dichlorophenyl)thio)-1,4-dihydro-5H-pyrazolo[3,4-b]pyrazin-5-one |
| 42 | 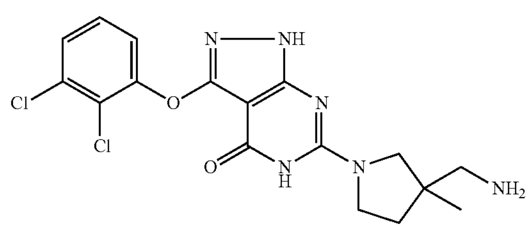 [SMILES: CC1(CN)CCN(c2nc3[nH]nc(Oc4cccc(Cl)c4Cl)c3c(=O)[nH]2)C1] | 6-(3-(aminomethyl)-3-methylpyrrolidin-1-yl)-3-(2,3-dichlorophenoxy)-1,5-dihydro-4H-pyrazolo[3,4-d]pyrimidin-4-one |
| 43 | 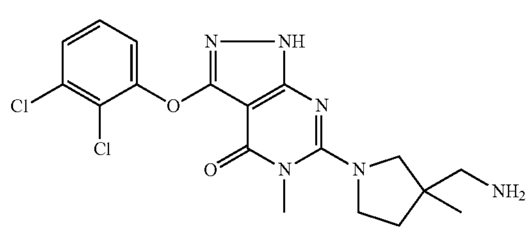 [SMILES: Cn1c(N2CCC(C)(CN)C2)nc2[nH]nc(Oc3cccc(Cl)c3Cl)c2c1=O] | 6-(3-(aminomethyl)-3-methylpyrrolidin-1-yl)-3-(2,3-dichlorophenoxy)-5-methyl-1,5-dihydro-4H-pyrazolo[3,4-d]pyrimidin-4-one |

TABLE 1-continued

| Compound ID | Structure | Compound name |
|---|---|---|
| 44 | 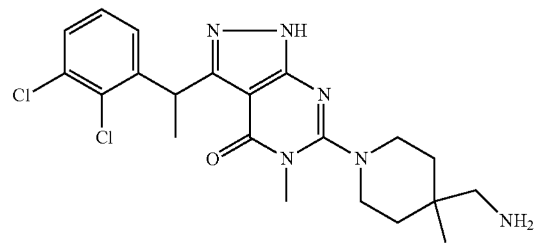 [SMILES: CC(c1cccc(Cl)c1Cl)c1n[nH]c2nc(N3CCC(C)(CN)CC3)n(C)c(=O)c12] | 6-(4-(aminomethyl)-4-methylpiperidin-1-yl)-3-(1-(2,3-dichlorophenyl)ethyl)-5-methyl-1,5-dihydro-4H-pyrazolo[3,4-d]pyrimidin-4-one |
| 45 | 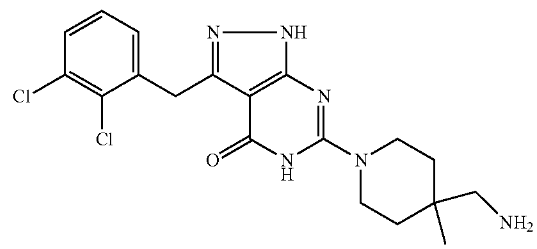 [SMILES: CC1(CN)CCN(c2nc3[nH]nc(Cc4cccc(Cl)c4Cl)c3c(=O)[nH]2)CC1] | 6-(4-(aminomethyl)-4-methylpiperidin-1-yl)-3-(2,3-dichlorobenzyl)-1,5-dihydro-4H-pyrazolo[3,4-d]pyrimidin-4-one |
| 46 | 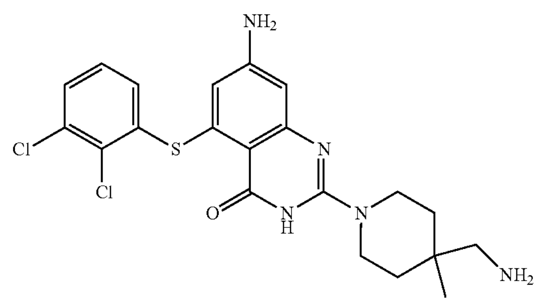 [SMILES: CC1(CN)CCN(c2nc3cc(N)cc(Sc4cccc(Cl)c4Cl)c3c(=O)[nH]2)CC1] | 7-amino-2-(4-(aminomethyl)-4-methylpiperidin-1-yl)-5-((2,3-dichlorophenyl)thio)quinazolin-4(3H)-one |
| 47 | 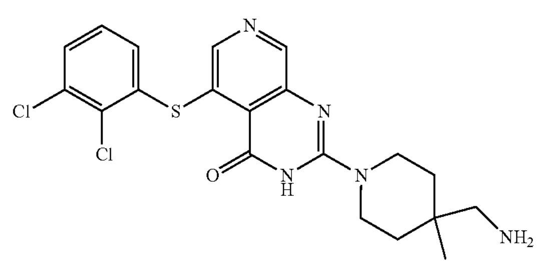 [SMILES: CC1(CN)CCN(c2nc3cncc(Sc4cccc(Cl)c4Cl)c3c(=O)[nH]2)CC1] | 2-(4-(aminomethyl)-4-methylpiperidin-1-yl)-5-((2,3-dichlorophenyl)thio)pyrido[3,4-d]pyrimidin-4(3H)-one |
| 48 | 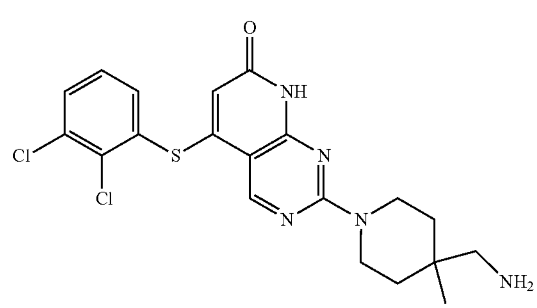 [SMILES: CC1(CN)CCN(c2ncc3c(Sc4cccc(Cl)c4Cl)cc(=O)[nH]c3n2)CC1] | 2-(4-(aminomethyl)-4-methylpiperidin-1-yl)-5-((2,3-dichlorophenyl)thio)pyrido[2,3-d]pyrimidin-7(8H)-one |

TABLE 1-continued

| Compound ID | Structure | Compound name |
|---|---|---|
| 49 | 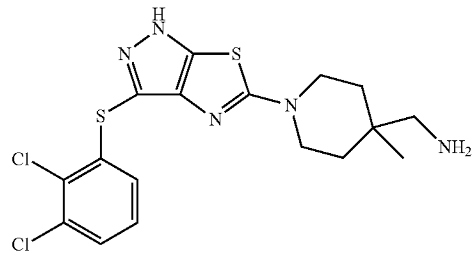 [SMILES: CC1(CN)CCN(c2nc3c(Sc4cccc(Cl)c4Cl)n[nH]c3s2)CC1] | (1-(3-((2,3-dichlorophenyl)thio)-1H-pyrazolo[4,3-d]thiazol-5-yl)-4-methylpiperidin-4-yl)methanamine |
| 50 | 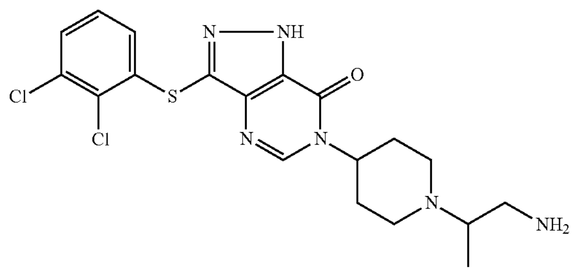 [SMILES: CC(CN)N1CCC(n2cnc3c(Sc4cccc(Cl)c4Cl)n[nH]c3c2=O)CC1] | 6-(1-(1-aminopropan-2-yl)piperidin-4-yl)-3-((2,3-dichlorophenyl)thio)-1,6-dihydro-7H-pyrazolo[4,3-d]pyrimidin-7-one |
| 51 | 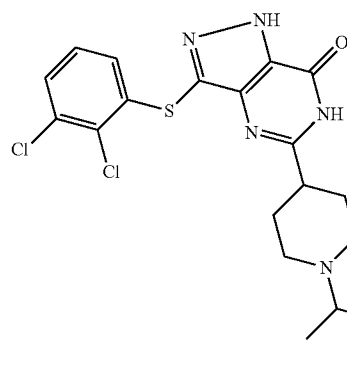 | 5-(1-(1-aminopropan-2-yl)piperidin-4-yl)-3-((2,3-dichlorophenyl)thio)-1,6-dihydro-7H-pyrazolo[4,3-d]pyrimidin-7-one |
| 52 | 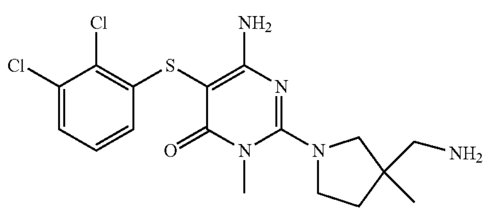 [SMILES: Cn1c(N2CCC(C)(CN)C2)nc(N)c(Sc2cccc(Cl)c2Cl)c1=O] | 6-amino-2-(3-(aminomethyl)-3-methylpyrrolidin-1-yl)-5-((2,3-dichlorophenyl)thio)-3-methylpyrimidin-4(3H)-one |
| 53 | 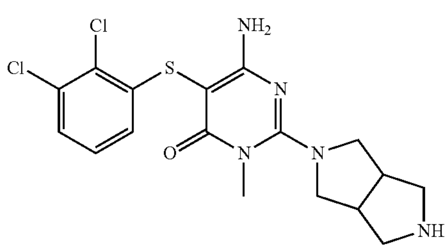 [SMILES: Cn1c(N2CC3CNCC3C2)nc(N)c(Sc2cccc(Cl)c2Cl)c1=O] | 6-amino-5-((2,3-dichlorophenyl)thio)-2-(hexahydropyrrolo[3,4-c]pyrrol-2(1H)-yl)-3-methylpyrimidin-4(3H)-one |
| 54 | 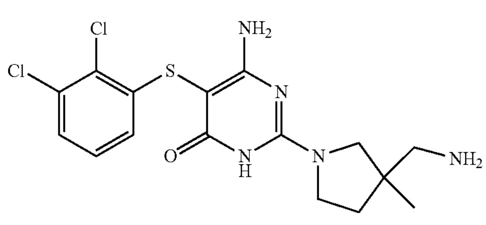 [SMILES: CC1(CN)CCN(c2nc(N)c(Sc3cccc(Cl)c3Cl)c(=O)[nH]2)C1] | 6-amino-2-(3-(aminomethyl)-3-methylpyrrolidin-1-yl)-5-((2,3-dichlorophenyl)thio)pyrimidin-4(3H)-one |

TABLE 1-continued

| Compound ID | Structure | Compound name |
|---|---|---|
| 55 | 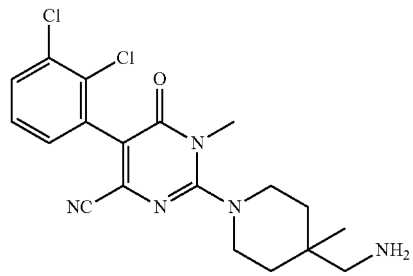 [SMILES: Cn1c(N2CCC(C)(CN)CC2)nc(C#N)c(-c2cccc(Cl)c2Cl)c1=O] | 2-(4-(aminomethyl)-4-methylpiperidin-1-yl)-5-(2,3-dichlorophenyl)-1-methyl-6-oxo-1,6-dihydropyrimidine-4-carbonitrile |
| 56 | 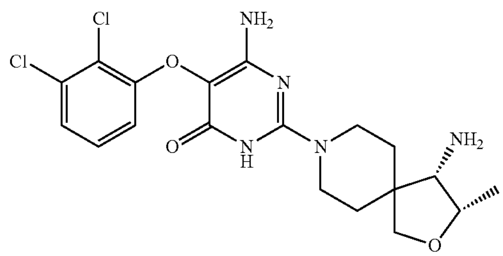 [SMILES: C[C@@H]1OCC2(CCN(c3nc(N)c(Oc4cccc(Cl)c4Cl)c(=O)[nH]3)CC2)[C@@H]1N] | 6-amino-2-((3S,4S)-4-amino-3-methyl-2-oxa-8-azaspiro[4.5]decan-8-yl)-5-(2,3-dichlorophenoxy)pyrimidin-4(3H)-one |
| 57 | 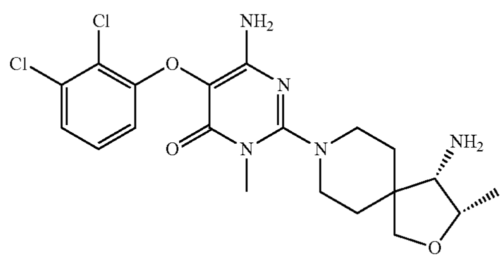 [SMILES: C[C@@H]1OCC2(CCN(c3nc(N)c(Oc4cccc(Cl)c4Cl)c(=O)n3C)CC2)[C@@H]1N] | 6-amino-2-((3S,4S)-4-amino-3-methyl-2-oxa-8-azaspiro[4.5]decan-8-yl)-5-(2,3-dichlorophenoxy)-3-methylpyrimidin-4(3H)-one |
| 58 | 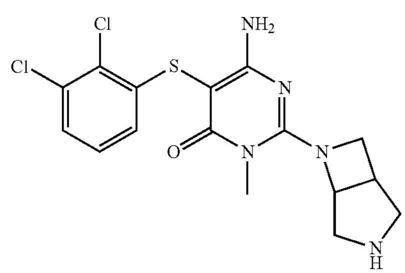 [SMILES: Cn1c(N2CC3CNCC32)nc(N)c(Sc2cccc(Cl)c2Cl)c1=O] | 6-amino-2-(3,6-diazabicyclo[3.2.0]heptan-6-yl)-5-((2,3-dichlorophenyl)thio)-3-methylpyrimidin-4(3H)-one |
| 59 | 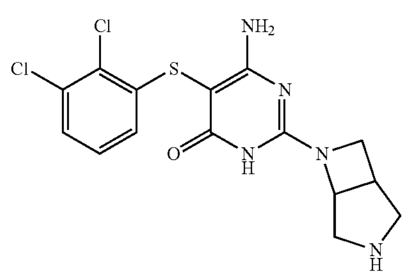 [SMILES: Nc1nc(N2CC3CNCC32)[nH]c(=O)c1Sc1cccc(Cl)c1Cl] | 6-amino-2-(3,6-diazabicyclo[3.2.0]heptan-6-yl)-5-((2,3-dichlorophenyl)thio)pyrimidin-4(3H)-one |
| 60 | 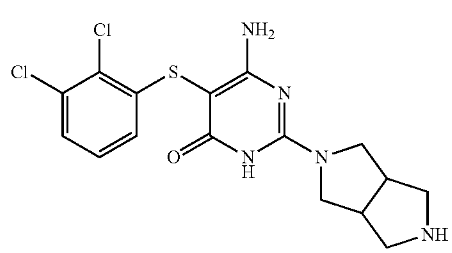 [SMILES: Nc1nc(N2CC3CNCC3C2)[nH]c(=O)c1Sc1cccc(Cl)c1Cl] | 6-amino-5-((2,3-dichlorophenyl)thio)-2-(hexahydropyrrolo[3,4-c]pyrrol-2(1H)-yl)pyrimidin-4(3H)-one |

TABLE 1-continued

| Compound ID | Structure | Compound name |
|---|---|---|
| 61 | 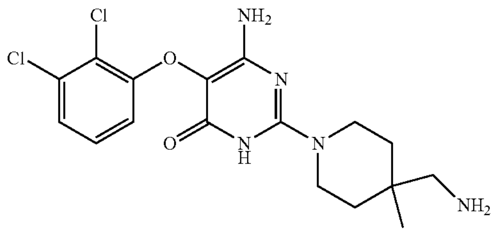 [SMILES: CC1(CN)CCN(c2nc(N)c(Oc3cccc(Cl)c3Cl)c(=O)[nH]2)CC1] | 6-amino-2-(4-(aminomethyl)-4-methylpiperidin-1-yl)-5-(2,3-dichlorophenoxy)pyrimidin-4(3H)-one |
| 62 | 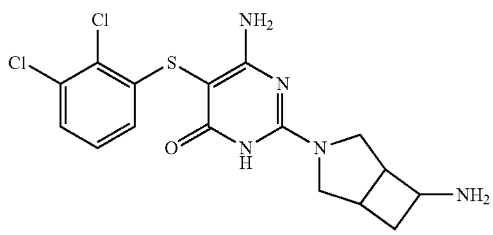 [SMILES: Nc1nc(N2CC3CC(N)C3C2)[nH]c(=O)c1Sc1cccc(Cl)c1Cl] | 6-amino-2-(6-amino-3-azabicyclo[3.2.0]heptan-3-yl)-5-((2,3-dichlorophenyl)thio)pyrimidin-4(3H)-one |
| 63 | 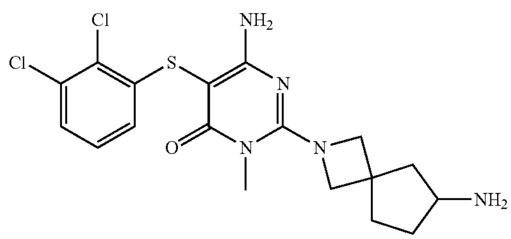 [SMILES: Cn1c(N2CC3(CCC(N)C3)C2)nc(N)c(Sc2cccc(Cl)c2Cl)c1=O] | 6-amino-2-(6-amino-2-azaspiro[3.4]octan-2-yl)-5-((2,3-dichlorophenyl)thio)-3-methylpyrimidin-4(3H)-one |
| 64 | 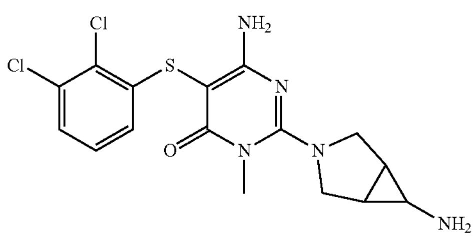 | 6-amino-2-(6-amino-3-azabicyclo[3.1.0]hexan-3-yl)-5-((2,3-dichlorophenyl)thio)-3-methylpyrimidin-4(3H)-one |
| 65 | 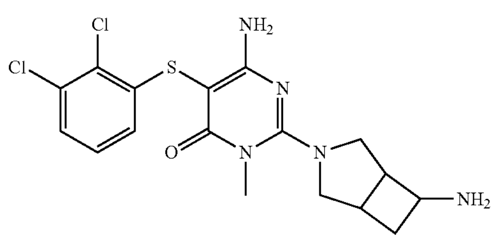 [SMILES: Cn1c(N2CC3CC(N)C3C2)nc(N)c(Sc2cccc(Cl)c2Cl)c1=O] | 6-amino-2-(6-amino-3-azabicyclo[3.2.0]heptan-3-yl)-5-((2,3-dichlorophenyl)thio)-3-methylpyrimidin-4(3H)-one |
| 66 | 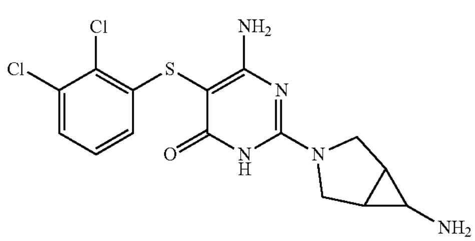 [SMILES: Nc1nc(N2CC3C(N)C3C2)[nH]c(=O)c1Sc1cccc(Cl)c1Cl] | 6-amino-2-(6-amino-3-azabicyclo[3.1.0]hexan-3-yl)-5-((2,3-dichlorophenyl)thio)pyrimidin-4(3H)-one |

TABLE 1-continued

| Compound ID | Structure | Compound name |
|---|---|---|
| 67 | 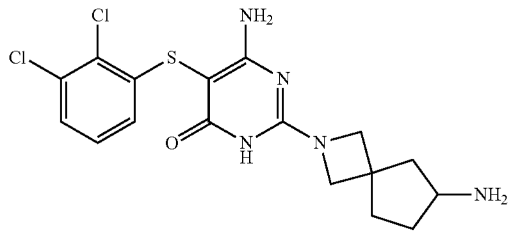 [SMILES: Nc1nc(N2CC3(CCC(N)C3)C2)[nH]c(=O)c1Sc1cccc(Cl)c1Cl] | 6-amino-2-(6-amino-2-azaspiro[3.4]octan-2-yl)-5-((2,3-dichlorophenyl)thio)pyrimidin-4(3H)-one |
| 68 | 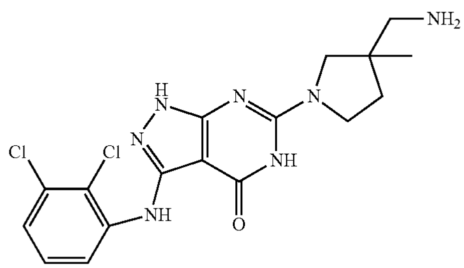 [SMILES: CC1(CN)CCN(c2nc3[nH]nc(Nc4cccc(Cl)c4Cl)c3c(=O)[nH]2)C1] | 6-(3-(aminomethyl)-3-methylpyrrolidin-1-yl)-3-((2,3-dichlorophenyl)amino)-1,5-dihydro-4H-pyrazolo[3,4-d]pyrimidin-4-one |
| 69 | 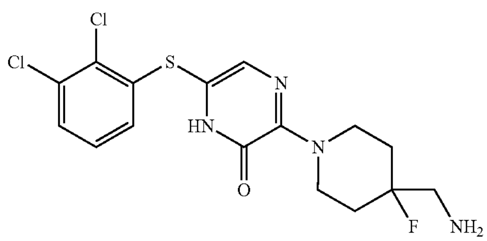 [SMILES: NCC1(F)CCN(c2ncc(Sc3cccc(Cl)c3Cl)[nH]c2=O)CC1] | 3-(4-(aminomethyl)-4-fluoropiperidin-1-yl)-6-((2,3-dichlorophenyl)thio)pyrazin-2(1H)-one |
| 70 | 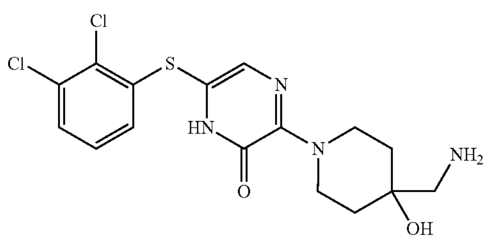 [SMILES: NCC1(O)CCN(c2ncc(Sc3cccc(Cl)c3Cl)[nH]c2=O)CC1] | 3-(4-(aminomethyl)-4-hydroxypiperidin-1-yl)-6-((2,3-dichlorophenyl)thio)pyrazin-2(1H)-one |
| 71 | 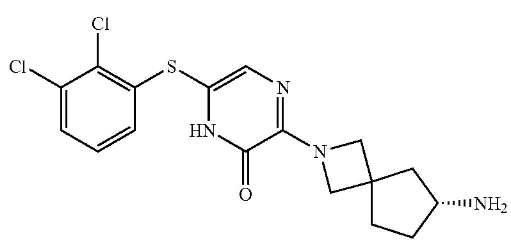 [SMILES: N[C@@H]1CCC2(C1)CN(c1ncc(Sc3cccc(Cl)c3Cl)[nH]c1=O)C2] | (R)-3-(6-amino-2-azaspiro[3.4]octan-2-yl)-6-((2,3-dichlorophenyl)thio)pyrazin-2(1H)-one |
| 72 | 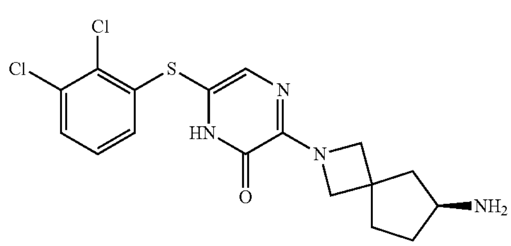 [SMILES: N[C@H]1CCC2(C1)CN(c1ncc(Sc3cccc(Cl)c3Cl)[nH]c1=O)C2] | (S)-3-(6-amino-2-azaspiro[3.4]octan-2-yl)-6-((2,3-dichlorophenyl)thio)pyrazin-2(1H)-one |

TABLE 1-continued

| Compound ID | Structure | Compound name |
|---|---|---|
| 73 | 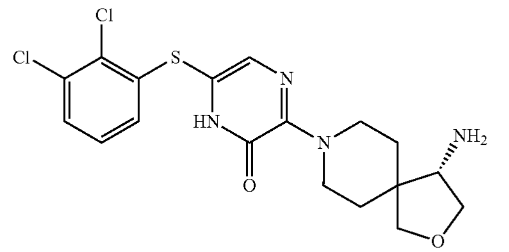 | (S)-3-(4-amino-2-oxa-8-azaspiro[4.5]decan-8-yl)-6-((2,3-dichlorophenyl)thio)pyrazin-2(1H)-one |
| 74 | 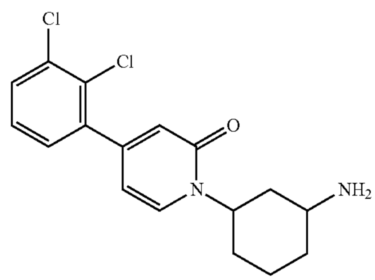 [SMILES: NC1CCCC(n2ccc(-c3cccc(Cl)c3Cl)cc2=O)C1] | 1-(3-aminocyclohexyl)-4-(2,3-dichlorophenyl)pyridin-2(1H)-one |
| 75 | 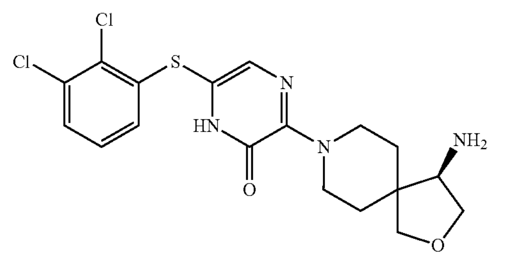 [SMILES: N[C@H]1COCC12CCN(c1ncc(Sc3cccc(Cl)c3Cl)[nH]c1=O)CC2] | (R)-3-(4-amino-2-oxa-8-azaspiro[4.5]decan-8-yl)-6-((2,3-dichlorophenyl)thio)pyrazin-2(1H)-one |
| 76 | 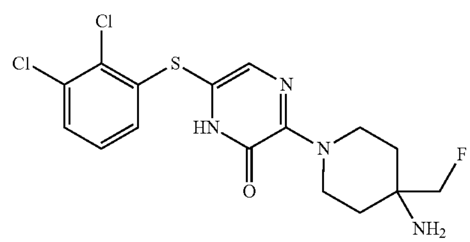 [SMILES: NC1(CF)CCN(c2ncc(Sc3cccc(Cl)c3Cl)[nH]c2=O)CC1] | 3-(4-amino-4-(fluoromethyl)piperidin-1-yl)-6-((2,3-dichlorophenyl)thio)pyrazin-2(1H)-one |
| 77 | 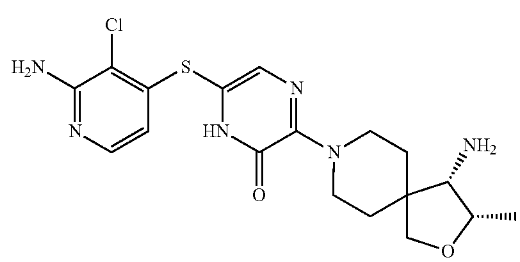 [SMILES: C[C@@H]1OCC2(CCN(c3ncc(Sc4ccnc(N)c4Cl)[nH]c3=O)CC2)[C@@H]1N] | 6-((2-amino-3-chloropyridin-4-yl)thio)-3-((3S,4S)-4-amino-3-methyl-2-oxa-8-azaspiro[4.5]decan-8-yl)pyrazin-2(1H)-one |
| 78 | 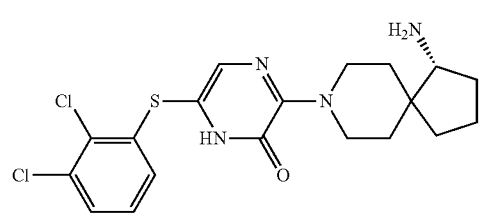 [SMILES: N[C@@H]1CCCC12CCN(c1ncc(Sc3cccc(Cl)c3Cl)[nH]c1=O)CC2] | (R)-3-(1-amino-8-azaspiro[4.5]decan-8-yl)-6-((2,3-dichlorophenyl)thio)pyrazin-2(1H)-one |

TABLE 1-continued

| Compound ID | Structure | Compound name |
|---|---|---|
| 79 | 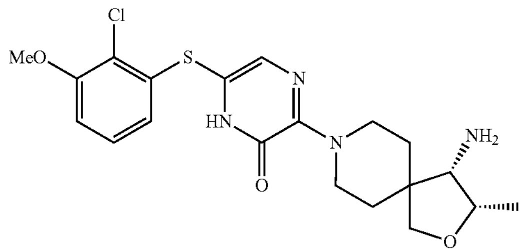 [SMILES: COc1cccc(Sc2cnc(N3CCC4(CC3)CO[C@@H](C)[C@H]4N)c(=O)[nH]2)c1Cl] | 3-((3S,4S)-4-amino-3-methyl-2-oxa-8-azaspiro[4.5]decan-8-yl)-6-((2-chloro-3-methoxyphenyl)thio)pyrazin-2(1H)-one |
| 80 | 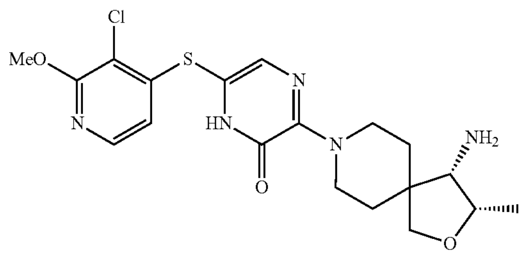 | 3-((3S,4S)-4-amino-3-methyl-2-oxa-8-azaspiro[4.5]decan-8-yl)-6-((3-chloro-2-methoxypyridin-4-yl)thio)pyrazin-2(1H)-one |
| 81 | 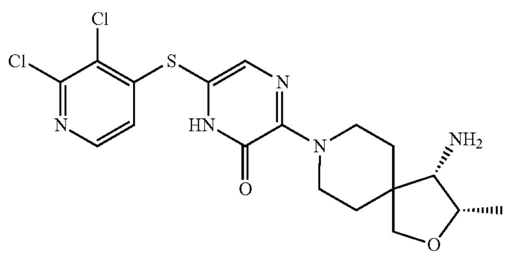 [SMILES: C[C@@H]1OCC2(CCN(c3ncc(Sc4ccnc(Cl)c4Cl)[nH]c3=O)CC2)[C@@H]1N] | 3-((3S,4S)-4-amino-3-methyl-2-oxa-8-azaspiro[4.5]decan-8-yl)-6-((2,3-dichloropyridin-4-yl)thio)pyrazin-2(1H)-one |
| 82 | 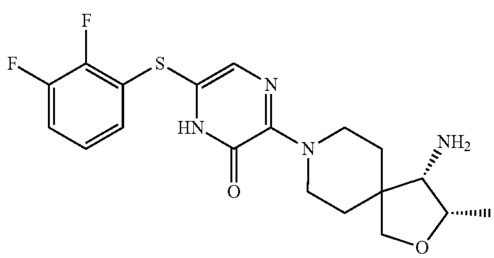 [SMILES: C[C@@H]1OCC2(CCN(c3ncc(Sc4cccc(F)c4F)[nH]c3=O)CC2)[C@@H]1N] | 3-((3S,4S)-4-amino-3-methyl-2-oxa-8-azaspiro[4.5]decan-8-yl)-6-((2,3-difluorophenyl)thio)pyrazin-2(1H)-one |
| 83 | 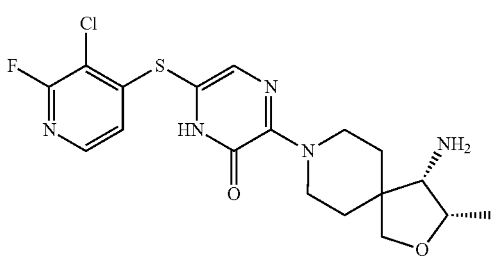 [SMILES: C[C@@H]1OCC2(CCN(c3ncc(Sc4ccnc(F)c4F)[nH]c3=O)CC2)[C@@H]1N] | 3-((3S,4S)-4-amino-3-methyl-2-oxa-8-azaspiro[4.5]decan-8-yl)-6-((3-chloro-2-fluoropyridin-4-yl)thio)pyrazin-2(1H)-one |
| 84 | 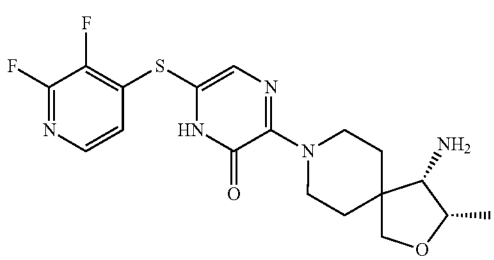 | 4-((5-(4-(aminomethyl)-4-methylpiperidin-1-yl)-6-oxo-1,6-dihydropyrazin-2-yl)thio)-3,3-difluoroindolin-2-one |

TABLE 1-continued

| Compound ID | Structure | Compound name |
|---|---|---|
| 85 | 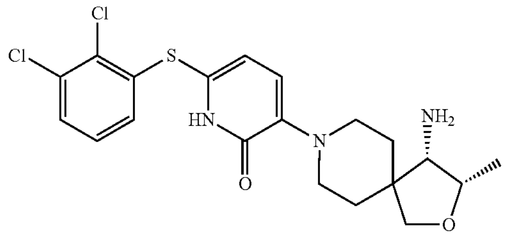 | 3-((3S,4S)-4-amino-3-methyl-2-oxa-8-azaspiro[4.5]decan-8-yl)-6-((2,3-dichlorophenyl)thio)pyridin-2(1H)-one |
| 86 | 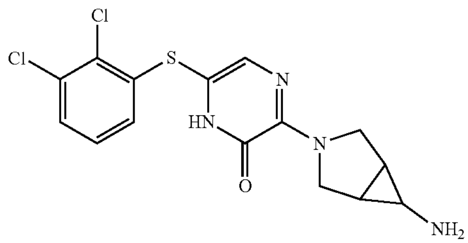 [SMILES: NC1C2CN(c3ncc(Sc4cccc(Cl)c4Cl)[nH]c3=O)CC12] | 3-(6-amino-3-azabicyclo[3.1.0]hexan-3-yl)-6-((2,3-dichlorophenyl)thio)pyrazin-2(1H)-one |
| 87 | 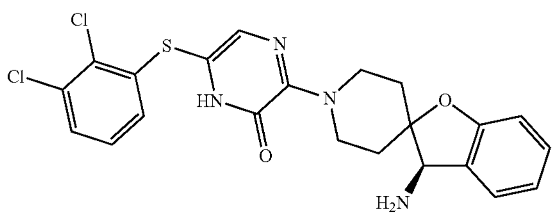 [SMILES: N[C@@H]1c2ccccc2OC12CCN(c1ncc(Sc3cccc(Cl)c3Cl)[nH]c1=O)CC2] | (R)-3-(3-amino-3H-spiro[benzofuran-2,4'-piperidin]-1'-yl)-6-((2,3-dichlorophenyl)thio)pyrazin-2(1H)-one |
| 88 | 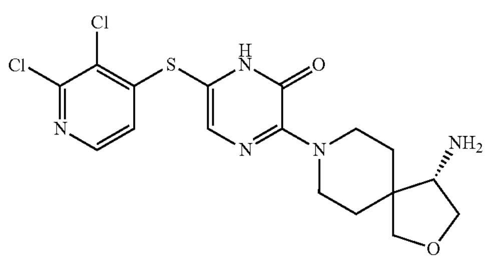 [SMILES: N[C@@H]1COCC12CCN(c1ncc(Sc3ccnc(Cl)c3Cl)[nH]c1=O)CC2] | (S)-3-(4-amino-2-oxa-8-azaspiro[4.5]decan-8-yl)-6-((2,3-dichloropyridin-4-yl)thio)pyrazin-2(1H)-one |
| 89 | 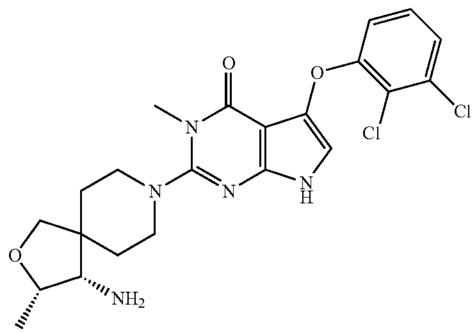 [SMILES: C[C@@H]1OCC2(CCN(c3nc4[nH]cc(Oc5cccc(Cl)c5Cl)c4c(=O)n3C)CC2)[C@@H]1N] | 2-((3S,4S)-4-amino-3-methyl-2-oxa-8-azaspiro[4.5]decan-8-yl)-5-(2,3-dichlorophenoxy)-3-methyl-3,7-dihydro-4H-pyrrolo[2,3-d]pyrimidin-4-one |

TABLE 1-continued

| Compound ID | Structure | Compound name |
|---|---|---|
| 90 | 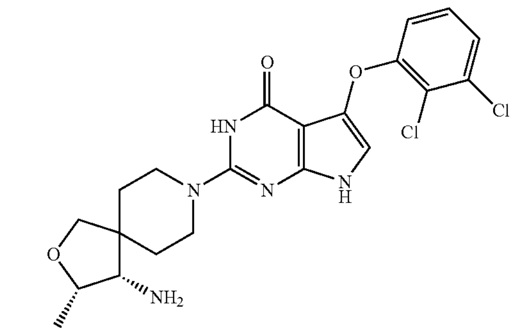 [SMILES: C[C@@H]1OCC2(CCN(c3nc4[nH]cc(Oc5cccc(Cl)c5Cl)c4c(=O)[nH]3)CC2)[C@@H]1N] | 2-((3S,4S)-4-amino-3-methyl-2-oxa-8-azaspiro[4.5]decan-8-yl)-5-(2,3-dichlorophenoxy)-3,7-dihydro-4H-pyrrolo[2,3-d]pyrimidin-4-one |
| 91 | 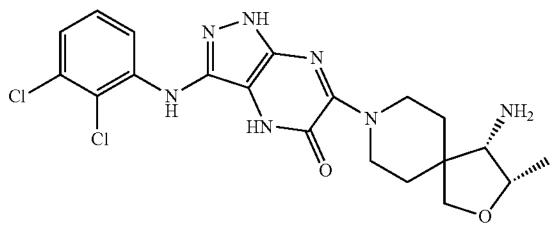 [SMILES: C[C@@H]1OCC2(CCN(c3nc4[nH]nc(Nc5cccc(Cl)c5Cl)c4[nH]c3=O)CC2)[C@@H]1N] | 6-((3S,4S)-4-amino-3-methyl-2-oxa-8-azaspiro[4.5]decan-8-yl)-3-((2,3-dichlorophenyl)amino)-1,4-dihydro-5H-pyrazolo[3,4-b]pyrazin-5-one |
| 92 | 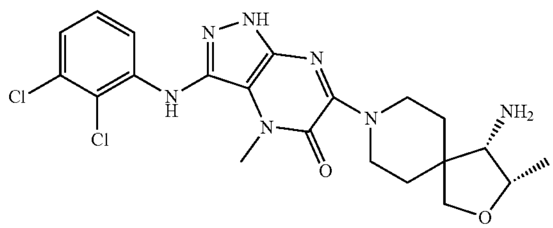 [SMILES: C[C@@H]1OCC2(CCN(c3nc4[nH]nc(Nc5cccc(Cl)c5Cl)c4n(C)c3=O)CC2)[C@@H]1N] | 6-((3S,4S)-4-amino-3-methyl-2-oxa-8-azaspiro[4.5]decan-8-yl)-3-((2,3-dichlorophenyl)amino)-4-methyl-1,4-dihydro-5H-pyrazolo[3,4-b]pyrazin-5-one |
| 93 | 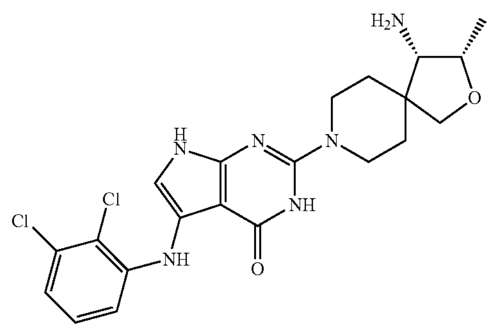 [SMILES: C[C@@H]1OCC2(CCN(c3nc4[nH]cc(Nc5cccc(Cl)c5Cl)c4c(=O)[nH]3)CC2)[C@@H]1N] | 2-((3S,4S)-4-amino-3-methyl-2-oxa-8-azaspiro[4.5]decan-8-yl)-5-((2,3-dichlorophenyl)amino)-3,7-dihydro-4H-pyrrolo[2,3-d]pyrimidin-4-one |
| 94 | 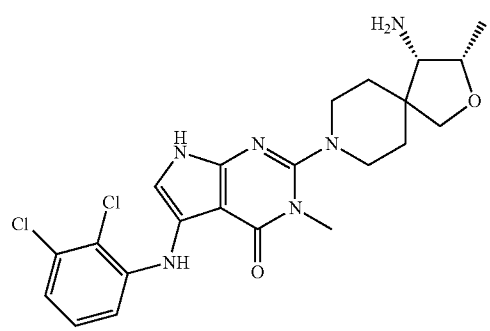 [SMILES: C[C@@H]1OCC2(CCN(c3nc4[nH]cc(Nc5cccc(Cl)c5Cl)c4c(=O)n3C)CC2)[C@@H]1N] | 2-((3S,4S)-4-amino-3-methyl-2-oxa-8-azaspiro[4.5]decan-8-yl)-5-((2,3-dichlorophenyl)amino)-3-methyl-3,7-dihydro-4H-pyrrolo[2,3-d]pyrimidin-4-one |

TABLE 1-continued

| Compound ID | Structure | Compound name |
|---|---|---|
| 95 | 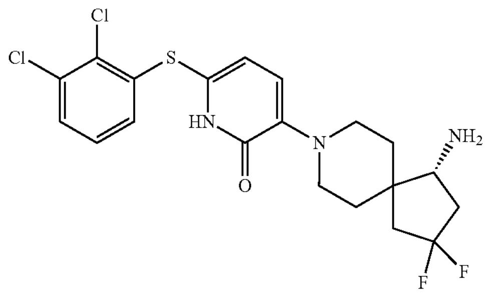 [SMILES: N[C@@H]1CC(F)(F)CC12CCN(c1ccc(Sc3cccc(Cl)c3Cl)[nH]c1=O)CC2] | (R)-3-(1-amino-3,3-difluoro-8-azaspiro[4.5]decan-8-yl)-6-((2,3-dichlorophenyl)thio)pyrazin-2(1H)-one |
| 96 | 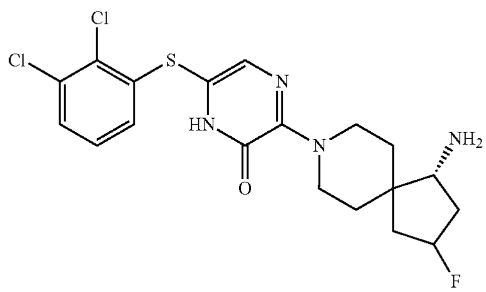 [SMILES: N[C@@H]1CC(F)CC12CCN(c1ncc(Sc3cccc(Cl)c3Cl)[nH]c1=O)CC2] | 3-((1R)-1-amino-3-fluoro-8-azaspiro[4.5]decan-8-yl)-6-((2,3-dichlorophenyl)thio)pyrazin-2(1H)-one |
| 97 | 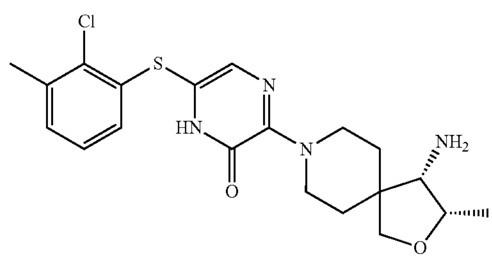 | 3-((3S,4S)-4-amino-3-methyl-2-oxa-8-azaspiro[4.5]decan-8-yl)-6-((2-chloro-3-methylphenyl)thio)pyrazin-2(1H)-one |
| 98 | 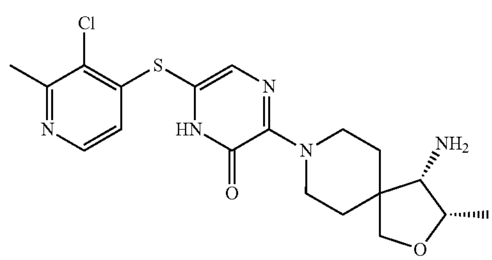 | 3-((3S,4S)-4-amino-3-methyl-2-oxa-8-azaspiro[4.5]decan-8-yl)-6-((3-chloro-2-methylpyridin-4-yl)thio)pyrazin-2(1H)-one |
| 99 | 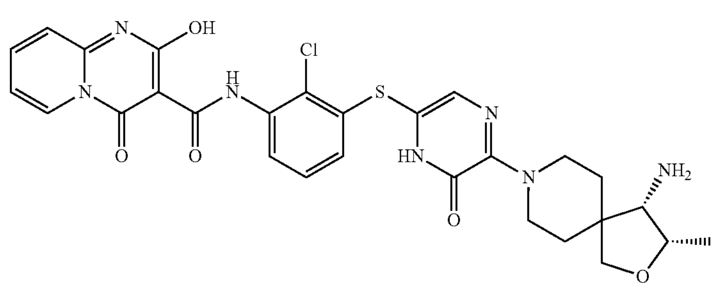 [SMILES: C[C@@H]1OCC2(CCN(c3ncc(Sc4cccc(NC(=O)c5c(O)nc6ccccn6c5=O)c4Cl)[nH]c3=O)CC2)[C@@H]1N] | N-(3-((5-((3S,4S)-4-amino-3-methyl-2-oxa-8-azaspiro[4.5]decan-8-yl)-6-oxo-1,6-dihydropyrazin-2-yl)thio)-2-chlorophenyl)-2-hydroxy-4-oxo-4H-pyrido[1,2-a]pyrimidine-3-carboxamide |

TABLE 1-continued

| Compound ID | Structure | Compound name |
|---|---|---|
| 100 | 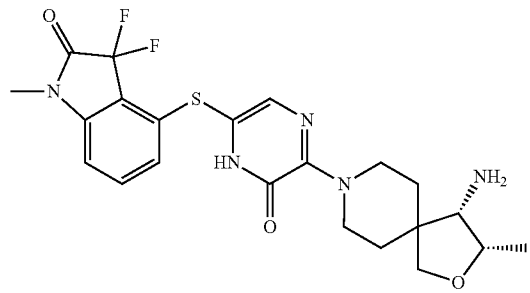 | 4-((5-((3S,4S)-4-amino-3-methyl-2-oxa-8-azaspiro[4.5]decan-8-yl)-6-oxo-1,6-dihydropyrazin-2-yl)thio)-3,3-difluoro-1-methylindolin-2-one |
| 101 | 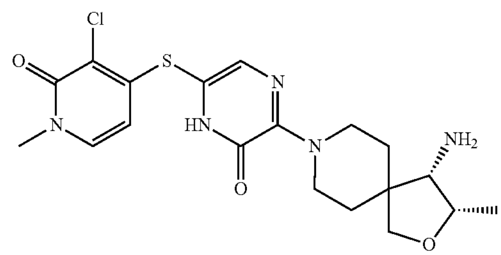 [SMILES: C[C@@H]1OCC2(CCN(c3ncc(Sc4ccn(C)c(=O)c4Cl)[nH]c3=O)CC2)[C@@H]1N] | 3-((3S,4S)-4-amino-3-methyl-2-oxa-8-azaspiro[4.5]decan-8-yl)-6-((3-chloro-1-methyl-2-oxo-1,2-dihydropyridin-4-yl)thio)pyrazin-2(1H)-one |
| 102 | 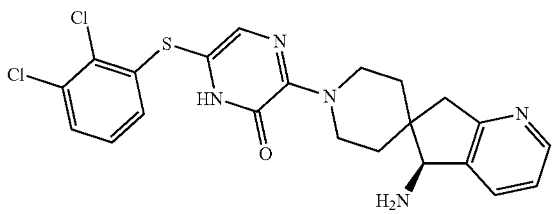 [SMILES: N[C@@H]1c2cccnc2CC12CCN(c1ncc(Sc3cccc(Cl)c3Cl)[nH]c1=O)CC2] | (S)-3-(5-amino-5,7-dihydrospiro[cyclopenta[b]pyridine-6,4'-piperidin]-1'-yl)-6-((2,3-dichlorophenyl)thio)pyrazin-2(1H)-one |
| 103 | 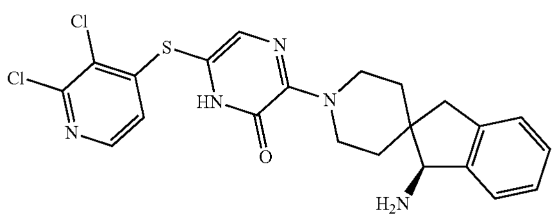 | (S)-3-(1-amino-1,3-dihydrospiro[indene-2,4'-piperidin]-1'-yl)-6-((2,3-dichloropyridin-4-yl)thio)pyrazin-2(1H)-one |
| 104 | 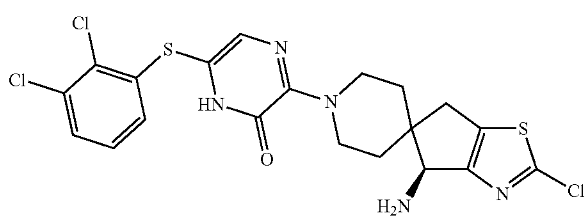 [SMILES: N[C@@H]1c2nc(Cl)sc2CC12CCN(c1ncc(Sc3cccc(Cl)c3Cl)[nH]c1=O)CC2] | (S)-3-(4-amino-2-chloro-4,6-dihydrospiro[cyclopenta[d]thiazole-5,4'-piperidin]-dichlorophenyl)thio)pyrazin-2(1H)-one |
| 105 | 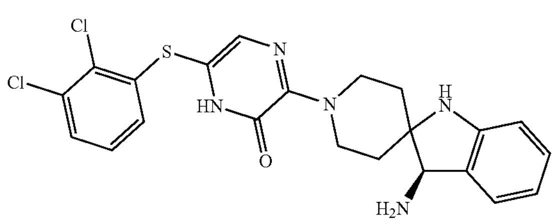 [SMILES: N[C@@H]1c2ccccc2NC12CCN(c1ncc(Sc3cccc(Cl)c3Cl)[nH]c1=O)CC2] | (R)-3-(3-aminospiro[indoline-2,4'-piperidin]-1'-yl)-6-((2,3-dichlorophenyl)thio)pyrazin-2(1H)-one |

TABLE 1-continued

| Compound ID | Structure | Compound name |
|---|---|---|
| 106 | 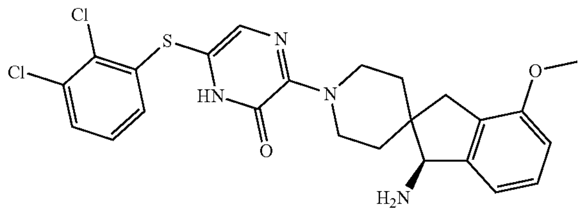 [SMILES: COc1cccc2c1CC1(CCN(c3ncc(Sc4cccc(Cl)c4Cl)[nH]c3=O)CC1)[C@@H]2N] | (S)-3-(1-amino-4-methoxy-1,3-dihydrospiro[indene-2,4'-piperidin]-1'-yl)-6-((2,3-dichlorophenyl)thio)pyrazin-2(1H)-one |
| 107 | 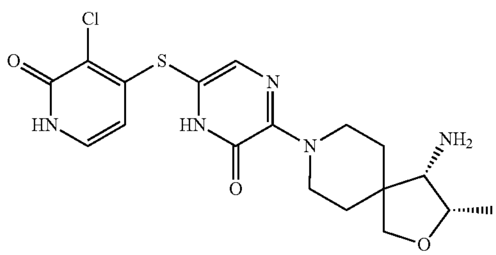 [SMILES: C[C@@H]1OCC2(CCN(c3ncc(Sc4cc[nH]c(=O)c4Cl)[nH]c3=O)CC2)[C@@H]1N] | 3-((3S,4S)-4-amino-3-methyl-2-oxa-8-azaspiro[4.5]decan-8-yl)-6-((3-chloro-2-oxo-1,2-dihydropyridin-4-yl)thio)pyrazin-2(1H)-one |
| 108 | 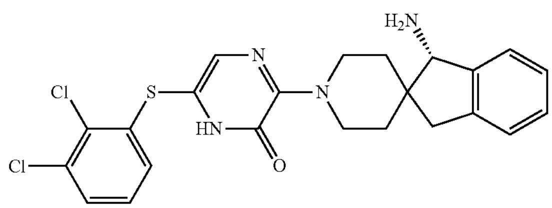 [SMILES: N[C@@H]1c2ccccc2CC12CCN(c1ncc(Sc3cccc(Cl)c3Cl)[nH]c1=O)CC2] | (S)-3-(1-amino-1,3-dihydrospiro[indene-2,4'-piperidin]-1'-yl)-6-((2,3-dichlorophenyl)thio)pyrazin-2(1H)-one |
| 109 | 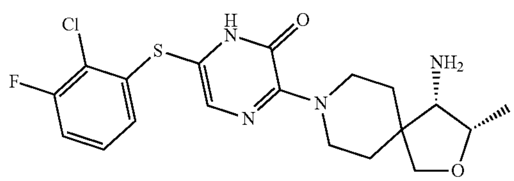 [SMILES: C[C@@H]1OCC2(CCN(c3ncc(Sc4cccc(F)c4Cl)[nH]c3=O)CC2)[C@@H]1N] | 3-((3S,4S)-4-amino-3-methyl-2-oxa-8-azaspiro[4.5]decan-8-yl)-6-((2-chloro-3-fluorophenyl)thio)pyrazin-2(1H)-one |
| 110 | 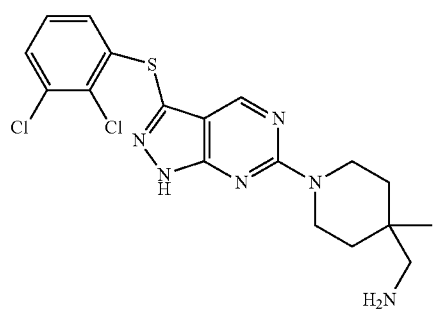 [SMILES: CC1(CN)CCN(c2ncc3c(Sc4cccc(Cl)c4Cl)n[nH]c3n2)CC1] | (1-(3-((2,3-dichlorophenyl)thio)-1H-pyrazolo[3,4-d]pyrimidin-6-yl)-4-methylpiperidin-4-yl)methanamine |
| 111 | 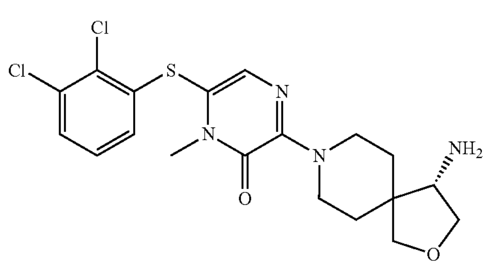 [SMILES: Cn1c(Sc2cccc(Cl)c2Cl)cnc(N2CCC3(CC2)COC[C@H]3N)c1=O] | 3-(4-amino-2-oxa-8-azaspiro[4.5]decan-8-yl)-6-((2,3-dichlorophenyl)thio)-1-methylpyrazin-2(1H)-one |

TABLE 1-continued

| Compound ID | Structure | Compound name |
|---|---|---|
| 112 | 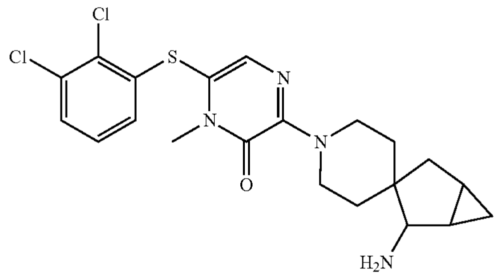 [SMILES: Cn1c(Sc2cccc(Cl)c2Cl)cnc(N2CCC3(CC2)CC2CC2C3N)c1=O] | 3-(2-aminospiro[bicyclo[3.1.0]hexane-3,4'-piperidin]-1'-yl)-6-((2,3-dichlorophenyl)thio)-1-methylpyrazin-2(1H)-one |
| 113 | 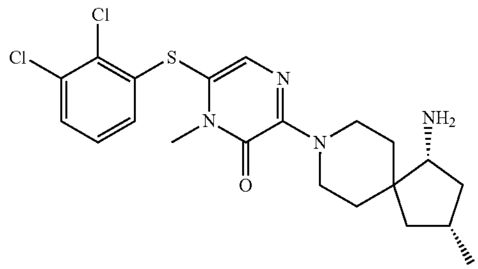 [SMILES: C[C@H]1C[C@@H](N)C2(CCN(c3ncc(Sc4cccc(Cl)c4Cl)n(C)c3=O)CC2)C1] | 3-((1R,3R)-1-amino-3-methyl-8-azaspiro[4.5]decan-8-yl)-6-((2,3-dichlorophenyl)thio)-1-methylpyrazin-2(1H)-one |
| 114 | 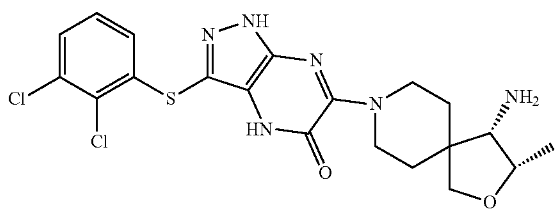 [SMILES: C[C@@H]1OCC2(CCN(c3nc4[nH]nc(Sc5cccc(Cl)c5Cl)c4[nH]c3=O)CC2)[C@@H]1N] | 6-((3S,4S)-4-amino-3-methyl-2-oxa-8-azaspiro[4.5]decan-8-yl)-3-(2,3-dichlorophenoxy)-1,4-dihydro-5H-pyrazolo[3,4-b]pyrazin-5-one |

An example, not as an attempt to limit the scope of the disclosure, of a useful composition for a dosage form containing about 10-1000 mg of compound 83 is shown in Table 113 below:

TABLE 1B

Example of dosage form of compound 83

| Component | Amount (wt/wt) |
|---|---|
| Compound 83 | 30-70% |
| lubricant | 1-10% |
| diluent | 20-70% |
| disintegrant | 1-10% |

A pharmaceutical composition comprising a compound of Formula 1 may be adapted for oral, or parental, such as intravenous, intramuscular, topical, intraperitoneal, nasal, buccal, sublingual, or subcutaneous administration, or for administration via respiratory tract in the form of, for example, an aerosol or an air-suspended fine powder. The dosage of a compound of Formula 1 may vary depending on the route of administration, body weight, age, the type and condition of the disease being treated. A pharmaceutical composition provided herein may optionally comprise two or more compounds of the Formula 1 without an additional therapeutic agent, or may comprise an additional therapeutic agent (i.e., a therapeutic agent other than a compound provided herein). For example, the subject compounds can be administered simultaneously, sequentially, or separately in combination with at least one other therapeutic agent. The other therapeutic agent can be a small molecule, an anti-body-drug conjugate, or a biologic. Therapeutic agents suitable for combination with a subject compound include, but are not limited to antibiotics, antiemetic agents, antidepressants, and antifungal agents, anti-inflammatory agents, antiviral agents, and anticancer agents that are known in the art. In some embodiments, the other therapeutic agents are chemotherapy agents, for example, mitotic inhibitors such as a taxane, a vinca alkaloid, paclitaxel; or tyrosine kinase inhibitors, for example Erlotinib; ALK inhibitors such as Crizotinib; BRAF inhibitors such as Vemurafanib; MEK inhibitors such as trametinib; or other anticancer agents, i.e. cisplatin, flutamide, gemcitabine, CTLA-4 inhibitors, PD-1 inhibitors and PD-L1 inhibitors. Such combination may offer significant advantages, including synergistic activity, in therapy. The pharmaceutical composition may be used for the treatment of cancer, autoimmune diseases, inflammatory diseases, autoinflammatory conditions, and other SHP2 mediated disorders in patients. The term "patient" herein means a mammal (e.g., a human or an animal). In some embodiments, the patient has cancer.

The pharmaceutical composition described herein can be prepared by combining a compound of Formula 1 with at least one pharmaceutical acceptable inert ingredient, such as a carrier, excipient, filler, lubricant, flavoring agent, buffer, etc., selected on the basis of the chosen route of administration and standard pharmaceutical practice as described, for example, in Remington's Pharmaceutical Sciences, 2005, the disclosure of which is hereby incorporated herein by reference, in its entirety. The relative proportions of active ingredient and carrier may be determined, for example, by the solubility and chemical nature of the compounds, chosen route of administration and standard pharmaceutical practice.

Some embodiments include a method of treating a SHP2 mediated disease or disorder comprising administering a therapeutically effective amount of a compound of Formula 1, or any compound described herein, or a pharmaceutically acceptable salt thereof ("subject compound"), or a pharmaceutical composition comprising a subject compound to a patient in need thereof. The term a "therapeutically effective amount" herein refers to an amount of a subject compound, or a pharmaceutical composition containing a subject compound, sufficient to be effective in inhibiting SHP2 and thus providing a benefit in the treatment of cancer, autoimmune diseases, inflammatory diseases, autoinflammatory conditions, and other SHP2 mediated disorders in patients, such as to delay or minimize symptoms associated with cancer, autoimmune, inflammatory diseases, and autoinflammatory conditions, or to ameliorate a disease or infection or cause thereof, or to prevent the further development of a disorder, or reducing the severity of symptoms that are otherwise expected to develop without treatment.

The following embodiments are contemplated:

Embodiment 1

A compound represented by a formula:

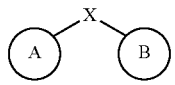

or a pharmaceutically acceptable salt thereof;
wherein X is S, O, $NR^A$, $CHR^A$, SO, $SO_2$, CO, or a bond;
Ring A is an optionally substituted aryl, heteroaryl or bicyclic ring system;
Ring B is an optionally substituted heterocyclic ring system, comprising a mono-cyclic ring, a bicyclic ring system, a tricyclic ring system, or a tetracyclic ring system, wherein the heterocyclic ring system contains heteroaryl and at least 2 ring nitrogen atoms; and
$R^A$ is H or $C_{1-6}$ hydrocarbyl.

Embodiment 2

The compound of embodiment 1, wherein Ring A is optionally substituted Phenyl.

Embodiment 3

The compound of embodiment 1, wherein Ring A is optionally substituted naphthalen-1-yl.

Embodiment 4

The compound of embodiment 1, wherein Ring A is optionally substituted pyridin-3-yl.

Embodiment 5

The compound of embodiment 1, wherein Ring A is optionally substituted pyridin-4-yl.

Embodiment 6

The compound of embodiment 1, wherein Ring A is optionally substituted 2-oxo-1,2-dihydropyridin-4-yl.

Embodiment 7

The compound of embodiment 1, wherein Ring A is optionally substituted 1H-indol-4-yl.

Embodiment 8

The compound of embodiment 1, wherein Ring A is optionally substituted 2-oxoindolin-4-yl.

Embodiment 9

The compound of embodiment 1, wherein Ring A is optionally substituted indolin-4-yl.

Embodiment 10

The compound of embodiment 1, wherein Ring A is optionally substituted 3-(2-oxo-2,5-dihydro-1H-pyrrole-3-carboxannido)phenyl.

Embodiment 11

The compound of embodiment 1, wherein Ring A is optionally substituted 3-(4-oxo-4H-pyrido[1,2-α]pyrimidine-3-carboxannido)phenyl.

Embodiment 12

The compound of embodiment 1, wherein Ring A is optionally substituted 3-(4-oxo-4H-pyrazino[1,2-α]pyrimidine-3-carboxannido)phenyl.

Embodiment 13

The compound of embodiment 1, wherein Ring A is optionally substituted 3-(5-oxo-5H-thiazolo[3,2-α]pyrimidine-6-carboxamido)phenyl.

Embodiment 14

The compound of embodiment 1, wherein Ring A is optionally substituted 3-(5-oxo-1,5-dihydroimidazo[1,2-α]pyrimidine-6-carboxamido)phenyl.

Embodiment 15

The compound of embodiment 1, wherein Ring A is optionally substituted 3-(4-oxo-6,7,8,9-tetrahydro-4H-pyrido[1,2-α]pyrimidine-3-carboxamido)phenyl.

Embodiment 16

The compound of embodiment 1, wherein Ring A is optionally substituted 2,3-dichlorophenyl.

Embodiment 17

The compound of embodiment 1, wherein Ring A is optionally substituted 2,3-dichloro-pyridin-4-yl.

Embodiment 18

The compound of embodiment 1, wherein Ring A is optionally substituted 2-amino-3-chloropyridin-4-yl

Embodiment 19

The compound of embodiment 1, 2, 3, 4, 5, 6, 7, 8, 9, 10, 11, 12, 13, 14, 15, 16, 17, or 18, wherein Ring A is unsubstituted.

Embodiment 20

The compound of embodiment 1, 2, 3, 4, 5, 6, 7, 8, 9, 10, 11, 12, 13, 14, 15, 16, 17, or 18, wherein Ring A has a Cl substituent.

Embodiment 21

The compound of embodiment 1, 2, 3, 4, 5, 6, 7, 8, 9, 10, 11, 12, 13, 14, 15, 16, 17, or 18, wherein Ring A has two Cl substituents.

Embodiment 22

The compound of embodiment 1, 2, 3, 4, 5, 6, 7, 8, 9, 10, 11, 12, 13, 14, 15, 16, 17, or 18, wherein Ring A has a $CF_3$ substituent.

Embodiment 23

The compound of embodiment 1, 2, 3, 4, 5, 6, 7, 8, 9, 10, 11, 12, 13, 14, 15, 16, 17, or 18, wherein Ring A has an $NH_2$ substituent.

Embodiment 24

The compound of embodiment 1, 2, 3, 4, 5, 6, 7, 8, 9, 10, 11, 12, 13, 14, 15, 16, 17, or 18, wherein Ring A has a —$OCH_3$ substituent.

Embodiment 25

The compound of embodiment 1, 2, 3, 4, 5, 6, 7, 8, 9, 10, 11, 12, 13, 14, 15, 16, 17, or 18, wherein Ring A has an F substituent.

Embodiment 26

The compound of embodiment 1, 2, 3, 4, 5, 6, 7, 8, 9, 10, 11, 12, 13, 14, 15, 16, 17, or 18, wherein Ring A has an acetyl substituent.

Embodiment 27

The compound of embodiment 1, 2, 3, 4, 5, 6, 7, 8, 9, 10, 11, 12, 13, 14, 15, 16, 17, or 18, wherein Ring A has a $CH_3$ substituent.

Embodiment 28

The compound of embodiment 1, 2, 3, 4, 5, 6, 7, 8, 9, 10, 11, 12, 13, 14, 15, 16, 17, or 18, wherein Ring A has an OH substituent.

Embodiment 29

The compound of embodiment 1, 2, 3, 4, 5, 6, 7, 8, 9, 10, 11, 12, 13, 14, 15, 16, 17, or 18, wherein Ring A has multiple substituents with any combination of the substituent of embodiment 20, 21, 22, 23, 24, 25, 26, 27, or 28, at any positions that are chemically permissible.

Embodiment 30

The compound of embodiment 1, wherein Ring A is any one of the following: phenyl, 2,3-dichlorophenyl, naphthalen-1-yl, 2-(trifluoromethyl)phenyl, 2-(trifluoromethyl)pyridin-3-yl, 5-amino-2-chlorophenyl, 5-amino-2-chloropyridin-3-yl, 3-amino-2-chlorophenyl, 2-amino-3-chloropyridin-4-yl, 2-chloro-3-methoxyphenyl, 3-chloro-2-methoxypyridin-4-yl, 3-fluoro-1H-indol-4-yl, 3,3-difluoro-2-oxoindolin-4-yl, 1-acetyl-3,3-difluoroindolin-4-yl, 2-chloro-3-(4-hydroxy-1,5,5-trimethyl-2-oxo-2,5-dihydro-1H-pyrrole-3-carboxamido)phenyl, 2-chloro-3-(2-hydroxy-4-oxo-4H-pyrido[1,2-a]pyrimidine-3-carboxamido)phenyl, 2-chloro-3-(2-hydroxy-4-oxo-4H-pyrazino[1,2-a]pyrimidine-3-carboxannido)phenyl, 2-chloro-3-(7-hydroxy-5-oxo-5H-thiazolo[3,2-a]pyrimidine-6-carboxamido)phenyl, 2-chloro-3-(7-hydroxy-5-oxo-1,5-dihydroimidazo[1,2-a]pyrimidine-6-carboxannido)phenyl, 2-chloro-3-(2-hydroxy-4-oxo-6,7,8,9-tetrahydro-4H-pyrido[1,2-a]pyrimidine-3-carboxamido)phenyl, 2,3-dichloropyridin-4-yl, 2,3-difluorophenyl, 3-chloro-2-fluoropyridin-4-yl, 2,3-difluoropyridin-4-yl, 2-chloro-3-methylphenyl, 3-chloro-2-methylpyridin-4-yl, 3,3-difluoro-1-methyl-2-oxoindolin-4-yl, 3-chloro-1-methyl-2-oxo-1,2-dihydropyridin-4-yl, or 2-chloro-3-fluorophenyl.

Embodiment 31

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-5-(piperidin-1-yl)-1,6-dihydropyrazin-2-yl.

Embodiment 32

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-5-(pyrrolidin-1-yl)-1,6-dihydropyrazin-2-yl.

Embodiment 33

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 5-(hexahydropyrrolo[3,4-c]pyrrol-2(1H)-yl)-6-oxo-1,6-dihydropyrazin-2-yl.

Embodiment 34

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 5-(3,6-diazabicyclo[3.2.0]hepta n-6-yl)-6-oxo-1,6-dihydropyrazin-2-yl.

Embodiment 35

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-5-(2-oxa-8-azaspiro[4.5]decan-8-yl)-1,6-dihydropyrazin-2-yl.

Embodiment 36

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-5-(piperidin-4-ylamino)-1,6-dihydropyrazin-2-yl.

Embodiment 37

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-5-(spiro[bicyclo[3.1.0]hexane-3,4'-piperidin]-1'-yl)-1,6-dihydropyrazin-2-yl.

Embodiment 38

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-5-(8-azaspiro[4.5]decan-8-yl)-1,6-dihydropyrazin-2-yl.

Embodiment 39

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 4-oxo-6-(piperidin-1-yl)-4,5-dihydro-1H-pyrazolo[3,4-d]pyrimidin-3-yl.

Embodiment 40

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 4-oxo-6-(pyrrolidin-1-yl)-4,5-dihydro-1H-pyrazolo[3,4-d]pyrimidin-3-yl.

Embodiment 41

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 4-oxo-2-(piperidin-1-yl)-3,4-dihydroquinazolin-5-yl.

Embodiment 42

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 4-oxo-2-(piperidin-1-yl)-3,4-dihydropyrido[3,4-d]pyrimidin-5-yl.

Embodiment 43

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 7-oxo-2-(piperidin-1-yl)-7,8-dihydropyrido[2,3-d]pyrimidin-5-yl.

Embodiment 44

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 5-(piperidin-1-yl)-1H-pyrazolo[4,3-d]thiazol-3-yl.

Embodiment 45

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 7-oxo-6-(piperidin-4-yl)-6,7-dihydro-1H-pyrazolo[4,3-d]pyrimidin-3-yl.

Embodiment 46

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-8-(piperidin-1-yl)-6,7-dihydro-1H-purin-2-yl.

Embodiment 47

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 8-(piperidin-1-yl)-7H-purin-2-yl.

Embodiment 48

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-2-(pyrrolidin-1-yl)-1,6-dihydropyrimidin-5-yl.

Embodiment 49

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-2-(piperidin-1-yl)-1,6-dihydropyrimidin-5-yl.

Embodiment 50

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-2-(2-oxa-8-azaspiro[4.5]decan-8-yl)-1,6-dihydropyrimidin-5-yl.

Embodiment 51

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 2-(3,6-diazabicyclo[3.2.0]hepta n-6-yl)-6-oxo-1,6-dihydropyrimidin-5-yl.

Embodiment 52

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 2-(hexa hydropyrrolo[3,4-c]pyrrol-2(1H)-yl)-6-oxo-1,6-dihydropyrimidin-5-yl.

Embodiment 53

The compound of embodiment 1, 2, 3, 4, 5, 6, 7, 8, 9, 10, 11, 12, 13, 14, 15, 16, 17, 18, 19, 20, 21, 22, 23, 24, 25, 26,

67

27, 28, 29, or 30, wherein Ring B is optionally substituted 2-(3-azabicyclo[3.2.0]heptan-3-yl)-6-oxo-1,6-dihydropyrimidin-5-yl.

Embodiment 54

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-2-(2-azaspiro[3.4]octan-2-yl)-1,6-dihydropyrimidin-5-yl.

Embodiment 55

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 2-(3-azabicyclo[3.1.0]hexan-3-yl)-6-oxo-1,6-dihydropyrimidin-5-yl.

Embodiment 56

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-2-(2-azaspiro[3.4]octan-2-yl)-1,6-dihydropyrimidin-5-yl.

Embodiment 57

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 5-oxo-6-(2-oxa-8-azaspiro[4.5]decan-8-yl)-4,5-dihydro-1H-pyrazolo[3,4-b]pyrazin-3-yl.

Embodiment 58

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 5-oxo-6-(piperidin-1-yl)-4,5-dihydro-1H-pyrazolo[3,4-b]pyrazin-3-yl.

Embodiment 59

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-(piperidin-1-yl)-1H-pyrazolo[3,4-d]pyrimidin-3-yl.

Embodiment 60

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-5-(2-azaspiro[3.4]octan-2-yl)-1,6-dihydropyrazin-2-yl.

Embodiment 61

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 1-cyclohexyl-2-oxo-1,2-dihydropyridin-4-yl.

Embodiment 62

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 5-(3-azabicyclo[3.1.0]hexan-3-yl)-6-oxo-1,6-dihydropyrazin-2-yl.

Embodiment 63

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-5-(3H-spiro[benzofuran-2,4'-piperidin]-1'-yl)-1,6-dihydropyrazin-2-yl.

Embodiment 64

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 4-oxo-2-(2-oxa-8-azaspiro[4.5]decan-8-yl)-4,7-dihydro-3H-pyrrolo[2,3-d]pyrimidin-5-yl.

Embodiment 65

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 5-(5,7-dihydrospiro[cyclopenta[b]pyridine-6,4'-piperidin]-1'-yl)-6-oxo-1,6-dihydropyrazin-2-yl.

Embodiment 66

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 5-(1,3-dihydrospiro[indene-2,4'-piperidin]-1'-yl)-6-oxo-1,6-dihydropyrazin-2-yl.

Embodiment 67

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 5-(4,6-dihydrospiro[cyclopenta[d]thiazole-5,4'-piperidin]-1'-yl)-6-oxo-1,6-dihydropyrazin-2-yl.

Embodiment 68

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 6-oxo-5-(spiro[indoline-2,4'-piperidin]-1'-yl)-1,6-dihydropyrazin-2-yl.

Embodiment 69

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is optionally substituted 5-((3S,4S)-4-amino-3-methyl-2-oxa-8-azaspiro[4.5]decan-8-yl)-6-oxo-1,6-dihydropyrazin-2-yl.

Embodiment 70

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42,

Embodiment 71

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69, wherein Ring B has a —CH$_3$ substituent.

Embodiment 72

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69, wherein Ring B has an —CH$_2$NH$_2$ substituent.

Embodiment 73

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69, wherein Ring B has an —NH$_2$ substituent.

Embodiment 74

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69, wherein Ring B has a —CH$_2$CH$_2$NH$_2$ substituent.

Embodiment 75

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69, wherein Ring B has a 1-aminopropan-2-yl substituent.

Embodiment 76

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69, wherein Ring B has a —CN substituent.

Embodiment 77

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69, wherein Ring B has an —F substituent.

Embodiment 78

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69, wherein Ring B has a —Cl substituent.

Embodiment 79

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69, wherein Ring B has a —CH$_2$F substituent.

Embodiment 80

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69, wherein Ring B has an —OH substituent.

Embodiment 81

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69, wherein Ring B has an —OCH$_3$ substituent.

Embodiment 82

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69, wherein Ring B has multiple substituents with any combination of the substituent of embodiment 72, 73, 74, 75, 76, 77, 78, 79, 80, or 81, at any positions that are chemically permissible.

Embodiment 83

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein Ring B is any one of the following: 5-(4-(aminomethyl)-4-methylpiperidin-1-yl)-6-oxo-1,6-dihydropyrazin-2-yl, 5-(3-(aminomethyl)-3-methylpyrrolidin-1-yl)-6-oxo-1,6-dihydropyrazin-2-yl, 5-(hexahydropyrrolo[3,4-c]pyrrol-2(1H)-yl)-6-oxo-1,6-dihydropyrazin-2-yl, 5-(3,6-diazabicyclo[3.2.0]heptan-6-yl)-6-oxo-1,6-dihydropyrazin-2-yl, (S)-5-(4-amino-2-oxa-8-azaspiro[4.5]decan-8-yl)-6-oxo-1,6-dihydropyrazin-2-yl, 6-oxo-5-(piperidin-4-ylamino)-1,6-dihydropyrazin-2-yl, 5-(2-aminospiro[bicyclo[3.1.0]hexane-3,4'-piperidin]-1'-yl)-6-oxo-1,6-dihydropyrazin-2-yl, 5-((1R,3R)-1-amino-3-methyl-8-azaspiro[4.5]decan-8-yl)-6-oxo-1,6-dihydropyrazin-2-yl, (6-(4-(aminomethyl)-4-methylpiperidin-1-yl)-4-oxo-4,5-dihydro-1H-pyrazolo[3,4-d]pyrimidin-3-yl)amino, 6-(3-(aminomethyl)-3-methylpyrrolidin-1-yl)-4-oxo-4,5-dihydro-1H-pyrazolo[3,4-d]pyrimidin-3-yl, 7-amino-2-(4-

(aminomethyl)-4-methylpiperidin-1-yl)-4-oxo-3,4-dihydroquinazolin-5-yl, 2-(4-(aminomethyl)-4-methylpiperidin-1-yl)-4-oxo-3,4-dihydropyrido[3,4-d]pyrimidin-5-yl, 2-(4-(aminomethyl)-4-methylpiperidin-1-yl)-7-oxo-7,8-dihydropyrido[2,3-d]pyrimidin-5-yl, 5-(4-(aminomethyl)-4-methylpiperidin-1-yl)-1H-pyrazolo[4,3-d]thiazol-3-yl, 6-(1-(1-aminopropan-2-yl)piperidin-4-yl)-7-oxo-6,7-dihydro-1H-pyrazolo[4,3-d]pyrimidin-3-yl, 8-(4-(aminomethyl)-4-methylpiperidin-1-yl)-6-oxo-6,7-dihydro-1H-purin-2-yl, 6-amino-8-(4-(aminomethyl)-4-methylpiperidin-1-yl)-7H-purin-2-yl, 4-amino-2-(3-(aminomethyl)-3-methylpyrrolidin-1-yl)-6-oxo-1,6-dihydropyrimidin-5-yl, 2-(4-(aminomethyl)-4-methylpiperidin-1-yl)-4-cyano-1-methyl-6-oxo-1,6-dihydropyrimidin-5-yl, 4-amino-2-(4-amino-2-oxa-8-azaspiro[4.5]decan-8-yl)-6-oxo-1,6-dihydropyrimidin-5-yl, 4-amino-2-(3,6-diazabicyclo[3.2.0]heptan-6-yl)-6-oxo-1,6-dihydropyrimidin-5-yl, 4-amino-2-(hexahydropyrrolo[3,4-c]pyrrol-2(1H)-yl)-6-oxo-1,6-dihydropyrimidin-5-yl, 4-amino-2-(4-(aminomethyl)-4-methylpiperidin-1-yl)-6-oxo-1,6-dihydropyrimidin-5-yl, 4-amino-2-(6-amino-3-azabicyclo[3.2.0]heptan-3-yl)-6-oxo-1,6-dihydropyrimidin-5-yl, 4-amino-2-(6-amino-2-azaspiro[3.4]octan-2-yl)-1-methyl-6-oxo-1,6-dihydropyrimidin-5-yl, 4-amino-2-(6-amino-3-azabicyclo[3.1.0]hexan-3-yl)-6-oxo-1,6-dihydropyrimidin-5-yl, 4-amino-2-(6-amino-2-azaspiro[3.4]octan-2-yl)-6-oxo-1,6-dihydropyrimidin-5-yl, 5-(4-(aminomethyl)-4-methylpiperidin-1-yl)-1-methyl-6-oxo-1,6-dihydropyrazin-2-yl, 5-(4-amino-2-oxa-8-azaspiro[4.5]decan-8-yl)-6-oxo-1,6-dihydropyrazin-2-yl, (S)-5-(4-amino-2-oxa-8-azaspiro[4.5]decan-8-yl)-1-methyl-6-oxo-1,6-dihydropyrazin-2-yl, 5-(2-aminospiro[bicyclo[3.1.0]hexane-3,4'-piperidin]-1'-yl)-1-methyl-6-oxo-1,6-dihydropyrazin-2-yl, 5-((3S,4S)-4-amino-3-methyl-2-oxa-8-azaspiro[4.5]decan-8-yl)-6-oxo-1,6-dihydropyrazin-2-yl, 5-((3S,4S)-4-amino-3-methyl-2-oxa-8-azaspiro[4.5]decan-8-yl)-1-methyl-6-oxo-1,6-dihydropyrazin-2-yl, 5-((1R,3R)-1-amino-3-methyl-8-azaspiro[4.5]decan-8-yl)-1-methyl-6-oxo-1,6-dihydropyrazin-2-yl, 5-(4-(aminomethyl)-4-methylpiperidin-1-yl)-6-oxo-1,6-dihydropyrazin-2-yl, 6-(4-(aminomethyl)-4-methylpiperidin-1-yl)-4-oxo-4,5-dihydro-1H-pyrazolo[3,4-d]pyrimidin-3-yl, 6-(4-(aminomethyl)-4-methylpiperidin-1-yl)-4-methyl-5-oxo-4,5-dihydro-1H-pyrazolo[3,4-b]pyrazin-3-yl, 6-(4-(aminomethyl)-4-methylpiperidin-1-yl)-5-oxo-4,5-dihydro-1H-pyrazolo[3,4-b]pyrazin-3-yl, 6-(3-(aminomethyl)-3-methylpyrrolidin-1-yl)-5-methyl-4-oxo-4,5-dihydro-1H-pyrazolo[3,4-d]pyrimidin-3-yl, 6-(4-(aminomethyl)-4-methylpiperidin-1-yl)-5-methyl-4-oxo-4,5-dihydro-1H-pyrazolo[3,4-d]pyrimidin-3-yl, 6-(4-(aminomethyl)-4-methylpiperidin-1-yl)-1H-pyrazolo[3,4-d]pyrimidin-3-yl, 4-amino-2-(hexahydropyrrolo[3,4-c]pyrrol-2(1H)-yl)-1-methyl-6-oxo-1,6-dihydropyrimidin-5-yl, 4-amino-2-((3S,4S)-4-amino-3-methyl-2-oxa-8-azaspiro[4.5]decan-8-yl)-6-oxo-1,6-dihydropyrimidin-5-yl, 4-amino-2-((3S,4S)-4-amino-3-methyl-2-oxa-8-azaspiro[4.5]decan-8-yl)-1-methyl-6-oxo-1,6-dihydropyrimidin-5-yl, 4-amino-2-(6-amino-3-azabicyclo[3.1.0]hexan-3-yl)-1-methyl-6-oxo-1,6-dihydropyrimidin-5-yl, 4-amino-2-(6-amino-3-azabicyclo[3.2.0]heptan-3-yl)-1-methyl-6-oxo-1,6-dihydropyrimidin-5-yl, 5-(4-(aminomethyl)-4-fluoropiperidin-1-yl)-6-oxo-1,6-dihydropyrazin-2-yl, 5-(4-(aminomethyl)-4-hydroxypiperidin-1-yl)-6-oxo-1,6-dihydropyrazin-2-yl, (R)-5-(6-amino-2-azaspiro[3.4]octan-2-yl)-6-oxo-1,6-dihydropyrazin-2-yl, (S)-5-(6-amino-2-azaspiro[3.4]octan-2-yl)-6-oxo-1,6-dihydropyrazin-2-yl, 1-(3-aminocyclohexyl)-2-oxo-1,2-dihydropyridin-4-yl, (R)-5-(4-amino-2-oxa-8-azaspiro[4.5]decan-8-yl)-6-oxo-1,6-dihydropyrazin-2-yl, 5-(4-amino-4-(fluoromethyl)piperidin-1-yl)-6-oxo-1,6-dihydropyrazin-2-yl, 5-((3S,4S)-4-amino-3-methyl-2-oxa-8-azaspiro[4.5]decan-8-yl)-6-oxo-1,6-dihydropyrazin-2-yl, (R)-5-(1-amino-8-azaspiro[4.5]decan-8-yl)-6-oxo-1,6-dihydropyrazin-2-yl, 5-(6-amino-3-azabicyclo[3.1.0]hexan-3-yl)-6-oxo-1,6-dihydropyrazin-2-yl, (R)-5-(3-amino-3H-spiro[benzofuran-2,4'-piperidin]-1'-yl)-6-oxo-1,6-dihydropyrazin-2-yl, 2-((3S,4S)-4-amino-3-methyl-2-oxa-8-azaspiro[4.5]decan-8-yl)-3-methyl-4-oxo-4,7-dihydro-3H-pyrrolo[2,3-d]pyrimidin-5-yl, 2-((3S,4S)-4-amino-3-methyl-2-oxa-8-azaspiro[4.5]decan-8-yl)-4-oxo-4,7-dihydro-3H-pyrrolo[2,3-d]pyrimidin-5-yl, (R)-5-(1-amino-3,3-difluoro-8-azaspiro[4.5]decan-8-yl)-6-oxo-1,6-dihydropyrazin-2-yl, 5-((1R)-1-amino-3-fluoro-8-azaspiro[4.5]decan-8-yl)-6-oxo-1,6-dihydropyrazin-2-yl, (S)-5-(5-amino-5,7-dihydrospiro[cyclopenta[b]pyridine-6,4'-piperidin]-1'-yl)-6-oxo-1,6-dihydropyrazin-2-yl, (S)-5-(1-amino-1,3-dihydrospiro[indene-2,4'-piperidin]-1'-yl)-6-oxo-1,6-dihydropyrazin-2-yl, (S)-5-(4-amino-2-chloro-4,6-dihydrospiro[cyclopenta[d]thiazole-5,4'-piperidin]-1'-yl)-6-oxo-1,6-dihydropyrazin-2-yl, (R)-5-(3-aminospiro[indoline-2,4'-piperidin]-1'-yl)-6-oxo-1,6-dihydropyrazin-2-yl, or (S)-5-(1-amino-4-methoxy-1,3-dihydrospiro[indene-2,4'-piperidin]-1'-yl)-6-oxo-1,6-dihydropyrazin-2-yl.

Embodiment 84

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, or 83, wherein X is S.

Embodiment 85

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, or 83, wherein X is a bond.

Embodiment 86

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, or 83, wherein X is O.

Embodiment 87

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, or 83, wherein X is NH.

Embodiment 88

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, or 83, wherein X is CH(CH$_3$).

Embodiment 89

The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, or 83, wherein X is CH$_2$.

Embodiment 90

The compound of any preceding embodiment, wherein R$^A$ is H.

Embodiment 91

The compound of any preceding embodiment, wherein R$^A$ is CH$_3$.

Embodiment 92

A compound of any preceding embodiments, or a pharmaceutically acceptable salt thereof, wherein the compound is optionally substituted at any position that is chemically permissible.

Embodiment 93

The compound of any one of the preceding embodiments, wherein the compound is an R-enantiomer.

Embodiment 94

The compound of any one of the preceding embodiments, wherein the compound is an S-enantiomer.

Embodiment 95

The compound of any one of the preceding embodiments, wherein the compound is deuterated.

Embodiment 96

A compound, or a pharmaceutically acceptable salt thereof, wherein the compound is any one of the following compounds that is optionally substituted: 3-(4-(aminomethyl)-4-methylpiperidin-1-yl)-6-(2,3-dichlorophenyl) pyrazin-2(1H)-one, 3-(4-(aminomethyl)-4-methylpiperidin-1-yl)-6-((2,3-dichlorophenyl)thio)pyrazin-2(1H)-one, 3-(4-(aminomethyl)-4-methylpiperidin-1-yl)-6-((2,3-dichlorophenyl)thio)-1-methylpyrazin-2(1H)-one, 3-(4-(aminomethyl)-4-methylpiperidin-1-yl)-6-(2,3-dichlorophenoxy)pyrazin-2(1H)-one, 3-(4-(aminomethyl)-4-methylpiperidin-1-yl)-6-((2,3-dichlorophenyl)amino) pyrazin-2(1H)-one, 3-(4-(aminomethyl)-4-methylpiperidin-1-yl)-6-(2,3-dichlorophenoxy)-1-methylpyrazin-2(1H)-one, 3-(3-(aminomethyl)-3-methylpyrrolidin-1-yl)-6-((2,3-dichlorophenyl)thio)pyrazin-2(1H)-one, 6-((2,3-dichlorophenyl)thio)-3-(hexahydropyrrolo[3,4-c]pyrrol-2(1H)-yl)pyrazin-2(1H)-one, 3-(3,6-diazabicyclo[3.2.0]heptan-6-yl)-6-((2,3-dichlorophenyl)thio)pyrazin-2(1H)-one, 3-(4-amino-2-oxa-8-azaspiro[4.5]decan-8-yl)-6-((2,3-dichlorophenyl)thio)pyrazin-2(1H)-one, 6-((2,3-dichlorophenyl)thio)-3-(piperidin-4-ylamino)pyrazin-2(1H)-one, 3-(4-(aminomethyl)-4-methylpiperidin-1-yl)-6-(naphthalen-1-ylthio)pyrazin-2(1H)-one, 3-(2-aminospiro[bicyclo[3.1.0]hexane-3,4'-piperidin]-1'-yl)-6-((2,3-dichlorophenyl)thio)pyrazin-2(1H)-one, 3-((3S,4S)-4-amino-3-methyl-2-oxa-8-azaspiro[4.5]decan-8-yl)-6-((2,3-dichlorophenyl)thio)pyrazin-2(1H)-one, 3-((3S,4S)-4-amino-3-methyl-2-oxa-8-azaspiro[4.5]decan-8-yl)-6-((2,3-dichlorophenyl)thio)-1-methylpyrazin-2(1H)-one, 3-((1R,3R)-1-amino-3-methyl-8-azaspiro[4.5]decan-8-yl)-6-((2,3-dichlorophenyl)thio)pyrazin-2(1H)-one, 3-(4-(aminomethyl)-4-methylpiperidin-1-yl)-6-((2-(trifluoromethyl)phenyl)thio)pyrazin-2(1H)-one, 3-(4-(aminomethyl)-4-methylpiperidin-1-yl)-6-((2-(trifluoromethyl)pyridin-3-yl)thio)pyrazin-2(1H)-one, 6-((5-amino-2-chlorophenyl)thio)-3-(4-(aminomethyl)-4-methylpiperidin-1-yl)pyrazin-2(1H)-one, 6-((5-amino-2-chloropyridin-3-yl)thio)-3-(4-(aminomethyl)-4-methylpiperidin-1-yl)pyrazin-2(1H)-one, 6-((3-amino-2-chlorophenyl)thio)-3-(4-(aminomethyl)-4-methylpiperidin-1-yl)pyrazin-2(1H)-one, 6-((2-amino-3-chloropyridin-4-yl)thio)-3-(4-(aminomethyl)-4-methylpiperidin-1-yl)pyrazin-2(1H)-one, 3-(4-(aminomethyl)-4-methylpiperidin-1-yl)-6-((2-chloro-3-methoxyphenyl)thio)pyrazin-2(1H)-one, 3-(4-(aminomethyl)-4-methylpiperidin-1-yl)-6-((3-chloro-2-methoxypyridin-4-yl)thio)pyrazin-2(1H)-one, 3-((3S,4S)-4-amino-3-methyl-2-oxa-8-azaspiro[4.5]decan-8-yl)-6-((3-fluoro-1H-indol-4-yl)thio)pyrazin-2(1H)-one, 4-((5-(4-(aminomethyl)-4-methylpiperidin-1-yl)-6-oxo-1,6-dihydropyrazin-2-yl)thio)-3,3-difluoroindolin-2-one, 6-((1-acetyl-3,3-difluoroindolin-4-yl)thio)-3-(4-(aminomethyl)-4-methylpiperidin-1-yl)pyrazin-2(1H)-one, N-(3-((5-(4-(aminomethyl)-4-methylpiperidin-1-yl)-6-oxo-1,6-dihydropyrazin-2-yl)thio)-2-chlorophenyl)-4-hydroxy-1,5,5-trimethyl-2-oxo-2,5-dihydro-1H-pyrrole-3-carboxamide, N-(3-((5-(4-(aminomethyl)-4-methylpiperidin-1-yl)-6-oxo-1,6-dihydropyrazin-2-yl)thio)-2-chlorophenyl)-2-hydroxy-4-oxo-4H-pyrido[1,2-a]pyrimidine-3-carboxamide, N-(3-((5-(4-(aminomethyl)-4-methylpiperidin-1-yl)-6-oxo-1,6-dihydropyrazin-2-yl)thio)-2-chlorophenyl)-2-hydroxy-4-oxo-4H-pyrazino[1,2-a]pyrimidine-3-carboxamide, N-(3-((5-(4-(aminomethyl)-4-methylpiperidin-1-yl)-6-oxo-1,6-dihydropyrazin-2-yl)thio)-2-chlorophenyl)-7-hydroxy-5-oxo-5H-thiazolo[3,2-a]pyrimidine-6-carboxamide, N-(3-((5-(4-(aminomethyl)-4-methylpiperidin-1-yl)-6-oxo-1,6-dihydropyrazin-2-yl)thio)-2-chlorophenyl)-7-hydroxy-5-oxo-1,5-dihydroinnidazo[1,2-a]pyrimidine-6-carboxamide, N-(3-((5-(4-(aminomethyl)-4-methylpiperidin-1-yl)-6-oxo-1,6-dihydropyrazin-2-yl)thio)-2-chlorophenyl)-2-hydroxy-4-oxo-6,7,8,9-tetrahydro-4H-pyrido[1,2-a]pyrimidine-3-carboxamide, 6-(4-(aminomethyl)-4-methylpiperidin-1-yl)-3-((2,3-dichlorophenyl)amino)-1,5-dihydro-4H-pyrazolo[3,4-d]pyrimidin-4-one, 6-(4-(aminomethyl)-4-methylpiperidin-1-yl)-3-(2,3-dichlorophenoxy)-1,5-dihydro-4H-pyrazolo[3,4-d]pyrimidin-4-one, 6-(4-(aminomethyl)-4-methylpiperidin-1-yl)-3-((2,3-dichlorophenyl)amino)-5-methyl-1,5-dihydro-4H-pyrazolo[3,4-d]pyrimidin-4-one, 6-(4-(aminomethyl)-4-methylpiperidin-1-yl)-3-(2,3-dichlorophenoxy)-5-methyl-1,5-dihydro-4H-pyrazolo[3,4-d]pyrimidin-4-one, 6-(4-(aminomethyl)-4-methylpiperidin-1-yl)-3-(2,3-dichlorophenoxy)-4-methyl-1,4-dihydro-5H-pyrazolo[3,4-b]pyrazin-5-one, 6-(4-(aminomethyl)-4-methylpiperidin-1-yl)-3-(2,3-dichlorophenoxy)-1,4-dihydro-5H-pyrazolo[3,4-b]pyrazin-5-one, 6-(4-(aminomethyl)-4-methylpiperidin-1-yl)-3-(2,3-dichlorophenyl)-1,4-dihydro-5H-pyrazolo[3,4-b]pyrazin-5-one, 6-(4-(aminomethyl)-4-methylpiperidin-1- yl)-3-((2,3-dichlorophenyl)thio)-1,4-dihydro-5H-pyrazolo [3,4-b]pyrazin-5-one, 6-(3-(aminomethyl)-3-methylpyrrolidin-1-yl)-3-(2,3-dichlorophenoxy)-1,5-dihydro-4H-pyrazolo[3,4-d]pyrimidin-4-one, 6-(3-(aminomethyl)-3-methylpyrrolidin-1-yl)-3-(2,3-dichlorophenoxy)-5-methyl-1,5-dihydro-4H-pyrazolo[3,4-d]pyrimidin-4-one, 6-(4-(aminomethyl)-4-methylpiperidin-1-yl)-3-(1-(2,3-dichlorophenyl)ethyl)-5-methyl-1,5-dihydro-4H-pyrazolo[3,4-d]pyrimidin-4-one, 6-(4-(aminomethyl)-4-methylpiperidin-1-yl)-3-(2,3-dichlorobenzyl)-1,5-dihydro-4H-pyrazolo[3,4-d]pyrimidin-4-one, 7-amino-2-(4-(aminomethyl)-4-methylpiperidin-1-yl)-5-((2,3-dichlorophenyl)thio)quinazolin-4(3H)-one, 2-(4-(aminomethyl)-4-methylpiperidin-1-yl)-5-((2,3-dichlorophenyl)thio)pyrido[3,4-d]pyrimidin-4(3H)-one, 2-(4-(aminomethyl)-4-methylpiperidin-1-yl)-5-((2,3-dichlorophenyl)thio)pyrido[2,3-d]pyrimidin-7(8H)-one, (1-(3-((2,3-dichlorophenyl)thio)-1H-pyrazolo[4,3-d]thiazol-5-yl)-4-methylpiperidin-4-yl)methanamine, 6-(1-(1-aminopropan-2-yl)piperidin-4-yl)-3-((2,3-dichlorophenyl)thio)-1,6-dihydro-7H-pyrazolo[4,3-d]pyrimidin-7-one, 5-(1-(1-aminopropan-2-yl)piperidin-4-yl)-3-((2,3-dichlorophenyl)thio)-1,6-dihydro-7H-pyrazolo[4,3-d]pyrimidin-7-one, 6-amino-2-(3-(aminomethyl)-3-methylpyrrolidin-1-yl)-5-((2,3-dichlorophenyl)thio)-3-methylpyrimidin-4(3H)-one, 6-amino-5-((2,3-dichlorophenyl)thio)-2-(hexahydropyrrolo[3,4-c]pyrrol-2(1H)-yl)-3-methylpyrimidin-4(3H)-one, 6-amino-2-(3-(aminomethyl)-3-methylpyrrolidin-1-yl)-5-((2,3-dichlorophenyl)thio)pyrimidin-4(3H)-one, 2-(4-(aminomethyl)-4-methylpiperidin-1-yl)-5-(2,3-dichlorophenyl)-1-methyl-6-oxo-1,6-dihydropyrimidine-4-carbonitrile, 6-amino-2-((3S,4S)-4-amino-3-methyl-2-oxa-8-azaspiro[4.5]decan-8-yl)-5-(2,3-dichlorophenoxy)pyrimidin-4(3H)-one, 6-amino-2-((3S,4S)-4-amino-3-methyl-2-oxa-8-azaspiro[4.5]decan-8-yl)-5-(2,3-dichlorophenoxy)-3-methylpyrimidin-4(3H)-one, 6-amino-2-(3,6-diazabicyclo[3.2.0]heptan-6-yl)-5-((2,3-dichlorophenyl)thio)-3-methylpyrimidin-4(3H)-one, 6-amino-2-(3,6-diazabicyclo[3.2.0]heptan-6-yl)-5-((2,3-dichlorophenyl)thio)pyrimidin-4(3H)-one, 6-amino-5-((2,3-dichlorophenyl)thio)-2-(hexahydropyrrolo[3,4-c]pyrrol-2(1H)-yl)pyrimidin-4(3H)-one, 6-amino-2-(4-(aminomethyl)-4-methylpiperidin-1-yl)-5-(2,3-dichlorophenoxy)pyrimidin-4(3H)-one, 6-amino-2-(6-amino-3-azabicyclo[3.2.0]heptan-3-yl)-5-((2,3-dichlorophenyl)thio)pyrimidin-4(3H)-one, 6-amino-2-(6-amino-2-azaspiro[3.4]octan-2-yl)-5-((2,3-dichlorophenyl)thio)-3-methylpyrimidin-4(3H)-one, 6-amino-2-(6-amino-3-azabicyclo[3.1.0]hexan-3-yl)-5-((2,3-dichlorophenyl)thio)-3-methylpyrimidin-4(3H)-one, 6-amino-2-(6-amino-3-azabicyclo[3.2.0]heptan-3-yl)-5-((2,3-dichlorophenyl)thio)-3-methylpyrimidin-4(3H)-one, 6-amino-2-(6-amino-3-azabicyclo[3.1.0]hexan-3-yl)-5-((2,3-dichlorophenyl)thio)pyrimidin-4(3H)-one, 6-amino-2-(6-amino-2-azaspiro[3.4]octan-2-yl)-5-((2,3-dichlorophenyl)thio)pyrimidin-4(3H)-one, 6-(3-(aminomethyl)-3-methylpyrrolidin-1-yl)-3-((2,3-dichlorophenyl)amino)-1,5-dihydro-4H-pyrazolo[3,4-d]pyrimidin-4-one, 3-(4-(aminomethyl)-4-fluoropiperidin-1-yl)-6-((2,3-dichlorophenyl)thio)pyrazin-2(1H)-one, 3-(4-(aminomethyl)-4-hydroxypiperidin-1-yl)-6-((2,3-dichlorophenyl)thio)pyrazin-2(1H)-one, (R)-3-(6-amino-2-azaspiro[3.4]octan-2-yl)-6-((2,3-dichlorophenyl)thio)pyrazin-2(1H)-one, (S)-3-(6-amino-2-azaspiro[3.4]octan-2-yl)-6-((2,3-dichlorophenyl)thio)pyrazin-2(1H)-one, (S)-3-(4-amino-2-oxa-8-azaspiro[4.5]decan-8-yl)-6-((2,3-dichlorophenyl)thio)pyrazin-2(1H)-one, 1-(3-aminocyclohexyl)-4-(2,3-dichlorophenyl)pyridin-2(1H)-one, (R)-3-(4-amino-2-oxa-8-azaspiro[4.5]decan-8-yl)-6-((2,3-dichlorophenyl)thio)pyrazin-2(1H)-one, 3-(4-amino-4-(fluoromethyl)piperidin-1-yl)-6-((2,3-dichlorophenyl)thio)pyrazin-2(1H)-one, 6-((2-amino-3-chloropyridin-4-yl)thio)-3-((3S,4S)-4-amino-3-methyl-2-oxa-8-azaspiro[4.5]decan-8-yl)pyrazin-2(1H)-one, (R)-3-(1-amino-8-azaspiro[4.5]decan-8-yl)-6-((2,3-dichlorophenyl)thio)pyrazin-2(1H)-one, 3-((3S,4S)-4-amino-3-methyl-2-oxa-8-azaspiro[4.5]decan-8-yl)-6-((2-chloro-3-methoxyphenyl)thio)pyrazin-2(1H)-one, 3-((3S,4S)-4-amino-3-methyl-2-oxa-8-azaspiro[4.5]decan-8-yl)-6-((3-chloro-2-methoxypyridin-4-yl)thio)pyrazin-2(1H)-one, 3-((3S,4S)-4-amino-3-methyl-2-oxa-8-azaspiro[4.5]decan-8-yl)-6-((2,3-dichloropyridin-4-yl)thio)pyrazin-2(1H)-one, 3-((3S,4S)-4-amino-3-methyl-2-oxa-8-azaspiro[4.5]decan-8-yl)-6-((2,3-difluorophenyl)thio)pyrazin-2(1H)-one, 3-((3S,4S)-4-amino-3-methyl-2-oxa-8-azaspiro[4.5]decan-8-yl)-6-((3-chloro-2-fluoropyridin-4-yl)thio)pyrazin-2(1H)-one, 4-((5-(4-(aminomethyl)-4-methylpiperidin-1-yl)-6-oxo-1,6-dihydropyrazin-2-yl)thio)-3,3-difluoroindolin-2-one, 3-((3S,4S)-4-amino-3-methyl-2-oxa-8-azaspiro[4.5]decan-8-yl)-6-((2,3-dichlorophenyl)thio)pyridin-2(1H)-one, 3-(6-amino-3-azabicyclo[3.1.0]hexan-3-yl)-6-((2,3-dichlorophenyl)thio)pyrazin-2(1H)-one, (R)-3-(3-amino-3H-spiro[benzofuran-2,4'-piperidin]-1'-yl)-6-((2,3-dichlorophenyl)thio)pyrazin-2(1H)-one, (S)-3-(4-amino-2-oxa-8-azaspiro[4.5]decan-8-yl)-6-((2,3-dichloropyridin-4-yl)thio)pyrazin-2(1H)-one, 2-((3S,4S)-4-amino-3-methyl-2-oxa-8-azaspiro[4.5]decan-8-yl)-5-(2,3-dichlorophenoxy)-3-methyl-3,7-dihydro-4H-pyrrolo[2,3-d]pyrimidin-4-one, 2-((3S,4S)-4-amino-3-methyl-2-oxa-8-azaspiro[4.5]decan-8-yl)-5-(2,3-dichlorophenoxy)-3,7-dihydro-4H-pyrrolo[2,3-d]pyrimidin-4-one, 6-((3S,4S)-4-amino-3-methyl-2-oxa-8-azaspiro[4.5]decan-8-yl)-3-((2,3-dichlorophenyl)amino)-1,4-dihydro-5H-pyrazolo[3,4-b]pyrazin-5-one, 6-((3S,4S)-4-amino-3-methyl-2-oxa-8-azaspiro[4.5]decan-8-yl)-3-((2,3-dichlorophenyl)amino)-4-methyl-1,4-dihydro-5H-pyrazolo[3,4-b]pyrazin-5-one, 2-((3S,4S)-4-amino-3-methyl-2-oxa-8-azaspiro[4.5]decan-8-yl)-5-((2,3-dichlorophenyl)amino)-3,7-dihydro-4H-pyrrolo[2,3-d]pyrimidin-4-one, 2-((3S,4S)-4-amino-3-methyl-2-oxa-8-azaspiro[4.5]decan-8-yl)-5-((2,3-dichlorophenyl)amino)-3-methyl-3,7-dihydro-4H-pyrrolo[2,3-d]pyrimidin-4-one, (R)-3-(1-amino-3,3-difluoro-8-azaspiro[4.5]decan-8-yl)-6-((2,3-dichlorophenyl)thio)pyrazin-2(1H)-one, 3-((1R)-1-amino-3-fluoro-8-azaspiro[4.5]decan-8-yl)-6-((2,3-dichlorophenyl)thio)pyrazin-2(1H)-one, 3-((3S,4S)-4-amino-3-methyl-2-oxa-8-azaspiro[4.5]decan-8-yl)-6-((2-chloro-3-methylphenyl)thio)pyrazin-2(1H)-one, 3-((3S,4S)-4-amino-3-methyl-2-oxa-8-azaspiro[4.5]decan-8-yl)-6-((3-chloro-2-methylpyridin-4-yl)thio)pyrazin-2(1H)-one, N-(3-((5-((3S,4S)-4-amino-3-methyl-2-oxa-8-azaspiro[4.5]decan-8-yl)-6-oxo-1,6-dihydropyrazin-2-yl)thio)-2-chlorophenyl)-2-hydroxy-4-oxo-4H-pyrido[1,2-a]pyrimidine-3-carboxamide, 4-((5-((3S,4S)-4-amino-3-methyl-2-oxa-8-azaspiro[4.5]decan-8-yl)-6-oxo-1,6-dihydropyrazin-2-yl)thio)-3,3-difluoro-1-methylindolin-2-one, 3-((3S,4S)-4-amino-3-methyl-2-oxa-8-azaspiro[4.5]decan-8-yl)-6-((3-chloro-1-methyl-2-oxo-1,2-dihydropyridin-4-yl)thio)pyrazin-2(1H)-one, (S)-3-(5-amino-5,7-dihydrospiro[cyclopenta[b]pyridine-6,4'-piperidin]-1'-yl)-6-((2,3-dichlorophenyl)thio)pyrazin-2(1H)-one, (S)-3-(1-amino-1,3-dihydrospiro[indene-2,4'-piperidin]-1'-yl)-6-((2,3-dichloropyridin-4-yl)thio)pyrazin-2(1H)-one, (S)-3-(4-amino-2-chloro-4,6-dihydrospiro[cyclopenta[d]thiazole-5,4'-piperidin]-1'-yl)-6-((2,3-dichlorophenyl)thio)pyrazin-2(1H)-one, (R)-3-(3-aminospiro[indoline-2,4'-piperidin]-1'-yl)-6-((2,3- dichlorophenyl)thio)pyrazin-2(1H)-one, (S)-3-(1-amino-4-methoxy-1,3-dihydrospiro[indene-2,4'-piperidin]-1'-yl)-6-((2,3-dichlorophenyl)thio)pyrazin-2(1H)-one, 3-((3S,4S)-4-amino-3-methyl-2-oxa-8-azaspiro[4.5]decan-8-yl)-6-((3-chloro-2-oxo-1,2-dihydropyridin-4-yl)thio)pyrazin-2(1H)-one, (S)-3-(1-amino-1,3-dihydrospiro[indene-2,4'-piperidin]-1'-yl)-6-((2,3-dichlorophenyl)thio)pyrazin-2(1H)-one, 3-((3S,4S)-4-amino-3-methyl-2-oxa-8-azaspiro[4.5]decan-8-yl)-6-((2-chloro-3-fluorophenyl)thio)pyrazin-2(1H)-one, (1-(3-((2,3-dichlorophenyl)thio)-1H-pyrazolo[3,4-d]pyrimidin-6-yl)-4-methylpiperidin-4-yl)methanamine, 3-(4-amino-2-oxa-8-azaspiro[4.5]decan-8-yl)-6-((2,3-dichlorophenyl)thio)-1-methylpyrazin-2(1H)-one, 3-(2-aminospiro[bicyclo[3.1.0]hexane-3,4'-piperidin]-1'-yl)-6-((2,3-dichlorophenyl)thio)-1-methylpyrazin-2(1H)-one, 3-((1R,3R)-1-amino-3-methyl-8-azaspiro[4.5]decan-8-yl)-6-((2,3-dichlorophenyl)thio)-1-methylpyrazin-2(1H)-one, or 6-((3S,4S)-4-amino-3-methyl-2-oxa-8-azaspiro[4.5]decan-8-yl)-3-(2,3-dichlorophenoxy)-1,4-dihydro-5H-pyrazolo[3,4-b]pyrazin-5-one.

Embodiment 97

Any substituent of a compound of embodiment 1 has a molecular weight of about 15 g/mol to about 200 g/mol.

Embodiment 98

A pharmaceutical composition comprising a compound of any preceding embodiments or a pharmaceutically acceptable salt thereof, and a pharmaceutically acceptable vehicle, diluent, or carrier.

Embodiment 99

A method of treating a mammal, including a human, having a disease, disorders, or condition associated with the aberrant activity of SHP2, including cancer and autoimmune disorders, comprising administering to a mammal in need thereof a therapeutically effective amount of the compound of any preceding embodiment.

Embodiment 100

A medicament comprising a composition comprising a therapeutically effective amount of the compound of any preceding embodiment.

Embodiment 101

A kit comprising a medicament of embodiment 100 and a label indicating that the medicament is for treating a disease, disorders, or condition associated with the aberrant activity of SHP2.

EXPERIMENTAL

General Synthetic Methods:

The compounds of the present invention, or their pharmaceutically acceptable salts, can be synthesized using the methods described below in schemes 1-6. It will be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that optimum reaction conditions may vary with the particular reactants or solvents used, but such conditions can be determined by the person skilled in the art, using routine optimization procedures. Additionally, one skilled in the art will recognize that in many cases, these compounds will be mixtures of stereoisomers that may be separated at various stages of the synthetic schemes using conventional techniques, such as, but limited to, crystallization, normal-phase chromatography, reversed phase chromatography and chiral chromatography, to afford single enantiomers. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999. The schemes 1-6 are representative of methods useful in synthesizing the compounds of the present invention. They are not to constrain the scope of the invention in any way.

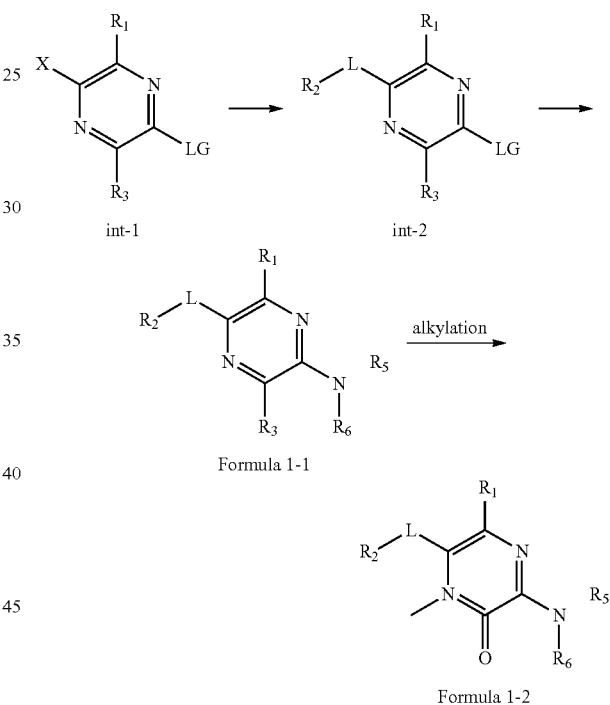

Scheme 1 illustrates a method for preparing compounds of Formula 1. In which L is S, O, N or a bond; $R_1$ is H, $C_1$-$C_6$ alkyl, $NH_2$, or CN; $R_2$ is aryl, heterocycloalkyl or heteroaryl; $R_3$ is $C_1$-$C_6$ alkyl, $OR_1$; $R_5$ is alkyl, H; $R_6$ is alkyl, H; $R_5$ and $R_6$ together with the atom or atoms to which they are attached, can combine to form a monocyclic or polycyclic $C_3$-$C_{12}$ cycloalkyl or heterocycle.

Compound int-1 is treated with aryl or alkyl boronic acids or esters or salts (where L is a bond) under suitable metal catalysts (such $Pd_2(dba)_3$, or the like), suitable ligands (such as dppf, or the like), suitable bases (such as $Cs_2CO_3$, or the like), suitable solvents (such as DMF, or the like) to provide a product of int-2. In other cases, where the L of Formula 1 is O, N or S, compound int-1 was reacted with corresponding phenols, thiophenols, thioalcohols or amines under suitable metal catalysts (such as CuI, $Pd_2(dba)_3$), suitable ligands (such as TMEDA, XPHOS, Xantphos, or the like), suitable salts or bases (such as $Cs_2CO_3$, $K_3PO_4$ or the like), suitable solvents (such as DMF, dioxane or the like) to provide a product of int-2. The reaction temperature is ranged from 80° C. to 140° C., and the reaction takes 1-24 hours to complete. Compound int-2 reacted with amines with or without bases (such as DIPEA), in suitable solvents (such as DMF, NMP or the like) under the temperature range from 80° C. to 140° C. to offer compound of Formula 1. If desired, further transformations may be performed to provide a product of Formula 1-2. For example, the compound of Formula 1-1 wherein $R_3$=OH may be subjected to an alkylation reaction to provide a compound of Formula 1-2.

Scheme 2

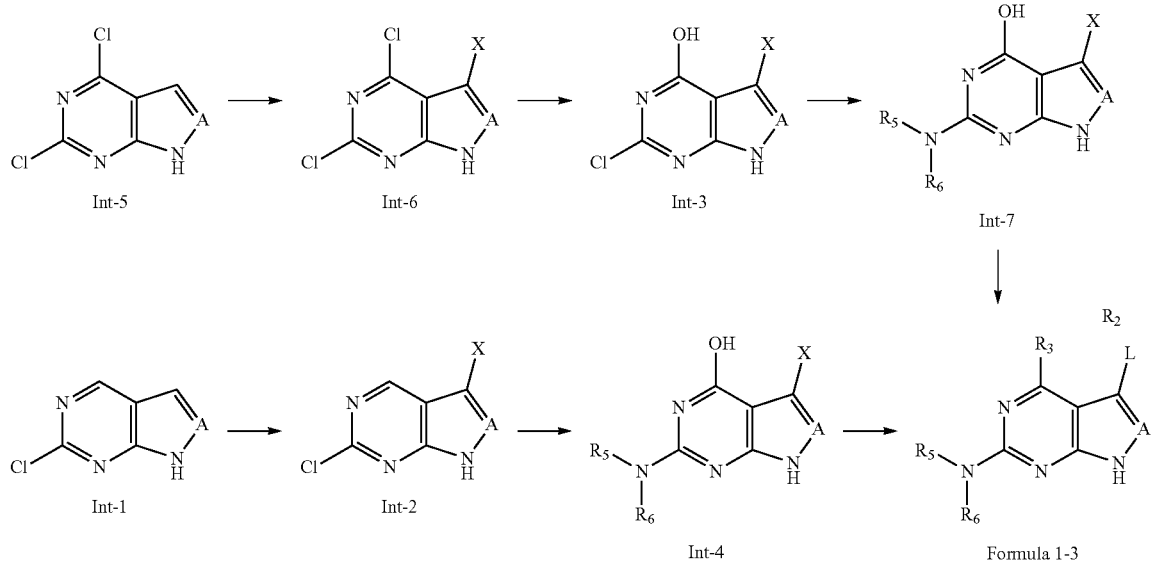

Scheme 2 illustrates a method for preparing compounds of Formula 1-3. Compound Int-1 was first halogenated to provide intermediate Int-2. The activated chlorine in Int-2 was displaced by an amine to afford Int-4. Int-4 reacted with an aryl amine or phenol to provide target compounds of Formula 1-3 ($R_3$=H).

For the compounds of Formula 1-3 where $R_3$ was OH, Int-6 was regioselectively hydrolyzed to provide Int-3, and then followed by substitutions and couplings to offer target compounds.

Deprotection steps can be incorporated either before or after the coupling reactions.

Scheme 3

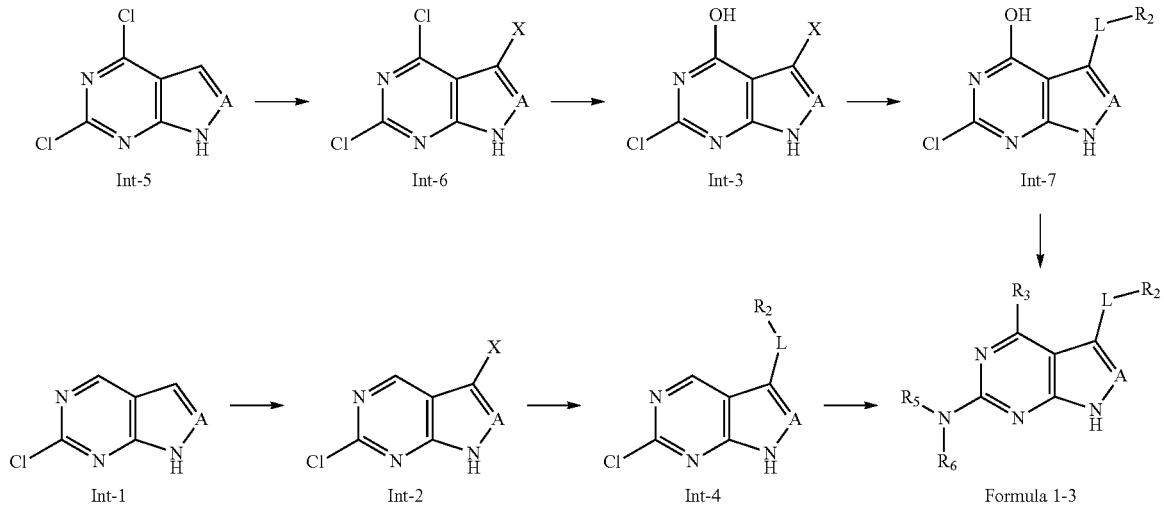

Additionally, the compounds of Formula 1-3 can be synthesized using an alternative way, as illustrated in Scheme 3. The order of reaction steps may alter. Coupling reactions may occur before the amine displacement.

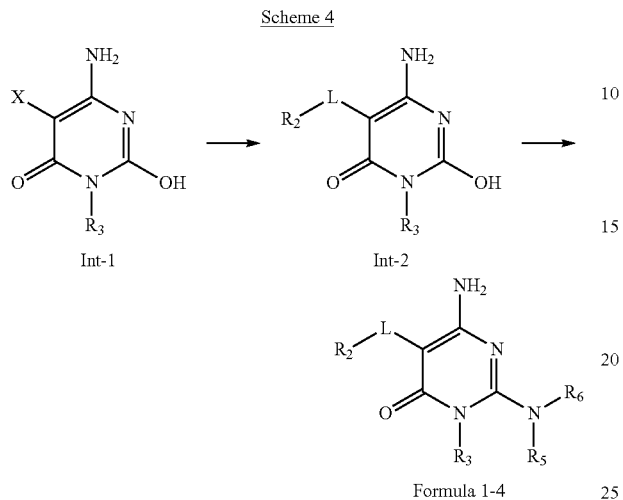

Scheme 4

Scheme 4 illustrates a method for preparing compounds of Formula 1-4. Int-1 was reacted with an aryl amine or phenol in the presence of a suitable metal catalyst (such as CuI, or the like), a suitable ligand (such as TMEDA, TMHD, or the like), a suitable salt (such as $K_3PO_4$, or the like) and a suitable solvent (such as dioxane or the like). The reaction proceeds at a temperature ranged 80° C. to 140° C., with the reaction time from 1-24 hours. Int-2 reacted with an amine in the presence of a suitable coupling reagent (such as BOP—Cl, or the like), a suitable base (such DIEPA, DBU, or the like), and a suitable solvent (such as DMF, THF or the like). The reaction proceeded at temperature 80° C. to 130° C. with 1-24 hours to finish.

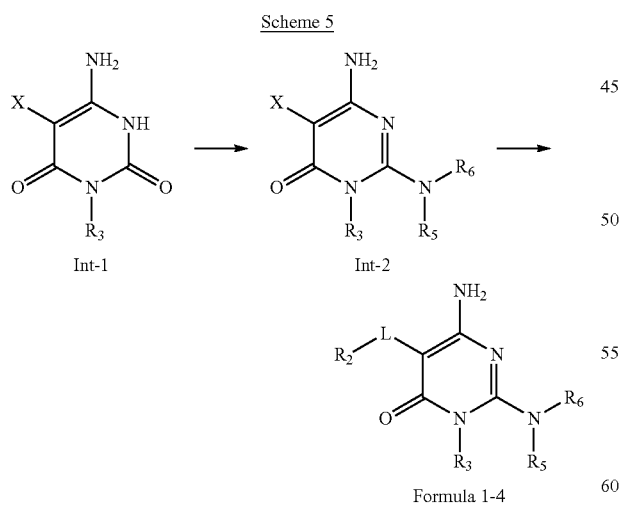

Scheme 5

Alternatively, as illustrated in Scheme 5, the order of reactions can be modified to change the overall synthesis to allow for variations at different positions of the molecule at different stages of the preparation. For example, in Scheme 5, compound of Formula Int-1 is activated and reacted with an amine to provide Int-2 first, and then followed with the coupling reaction, to provide compound of Formula 1-4.

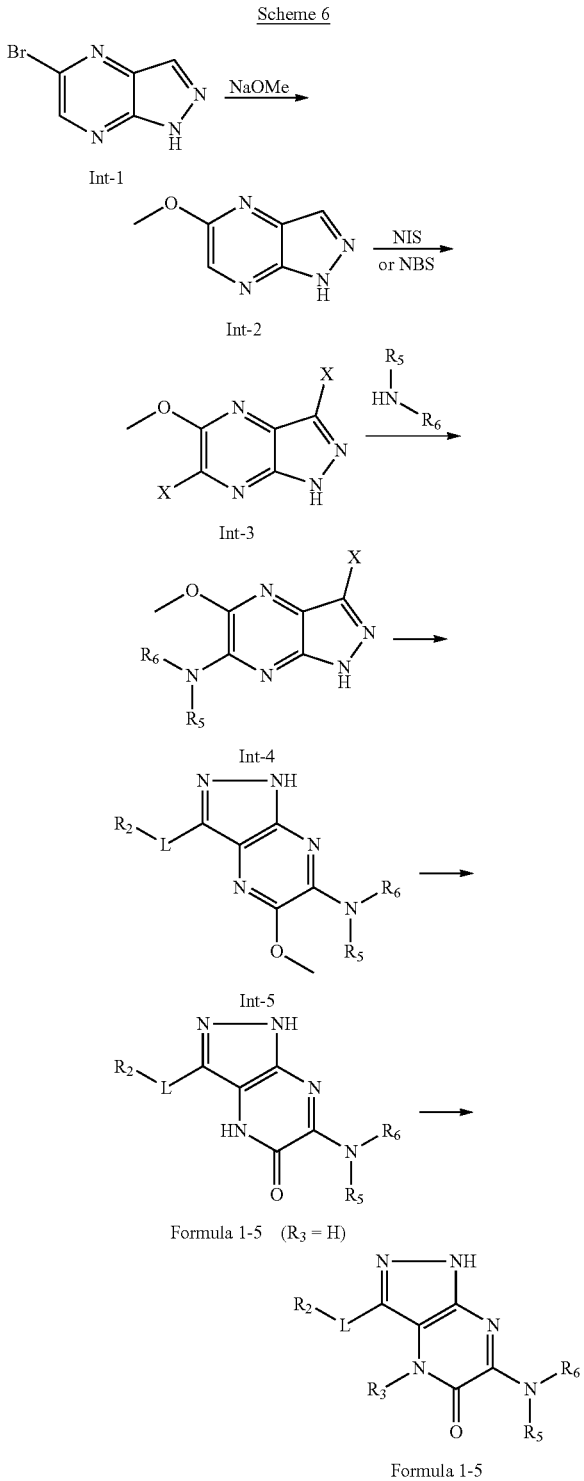

Scheme 6

Scheme 6 illustrates a method for preparing compounds of Formula 1-5.

Bromine of Int-1 was displaced with methoxy group to afford Int-2, and then Int-2 was halogenated with NBS or NIS to offer Int-3. From Int-3, after the substitution, coupling and deprotection compounds of formula 1-5 ($R_3$=H)

were synthesized. The compound of Formula 1-5 wherein R3=H may be subjected to an alkylation reaction to provide another series compound of Formula 1-5.

EXPERIMENTAL PROCEDURES AND EXAMPLES

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate. Products were generally dried under vacuum before being carried on to further reactions or submitted for biological testing. Mass spectrometry data is reported from liquid chromatography-mass spectrometry (LCMS) instrumentation. Mass spectra, MS (m/z), were recorded using either electrospray ionization (ESI) or atmospheric pressure chemical ionization (APCI). Where relevant and unless otherwise stated the m/z data provided are for isotopes 19F, 35Cl, 79Br and 127I. Chemical shifts for nuclear magnetic resonance (NMR) data are expressed in parts per million (ppm, δ) referenced to residual peaks from the deuterated solvents employed, using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; d6-DMSO, derterodimethylsulphoxide; and CD$_3$OD, deuteromethanol.

In general, reactions were followed by thin layer chromatography (TLC) and/or liquid chromatography-mass spectrometry (LCMS) and subjected to work-up when appropriate. Purification was carried out by chromatographic and/or HPLC.

Unless noted otherwise, all reactants were obtained commercially.

Example 1

Preparation of 2-(4-(aminomethyl)-4-methylpiperidin-1-yl)-5-(2,3-dichlorophenyl)-1-methyl-6-oxo-1,6-dihydropyrimidine-4-carbonitrile

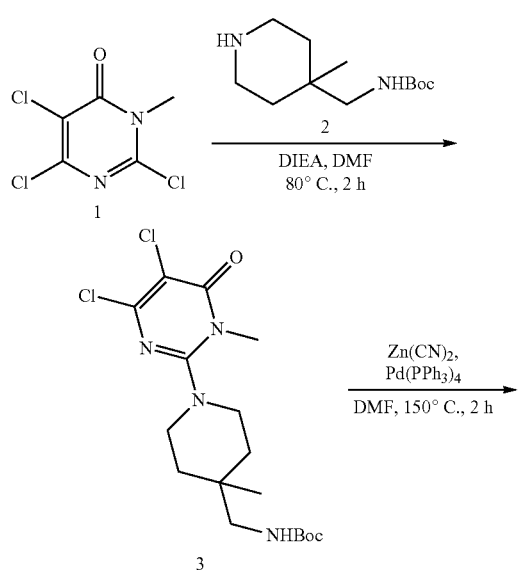

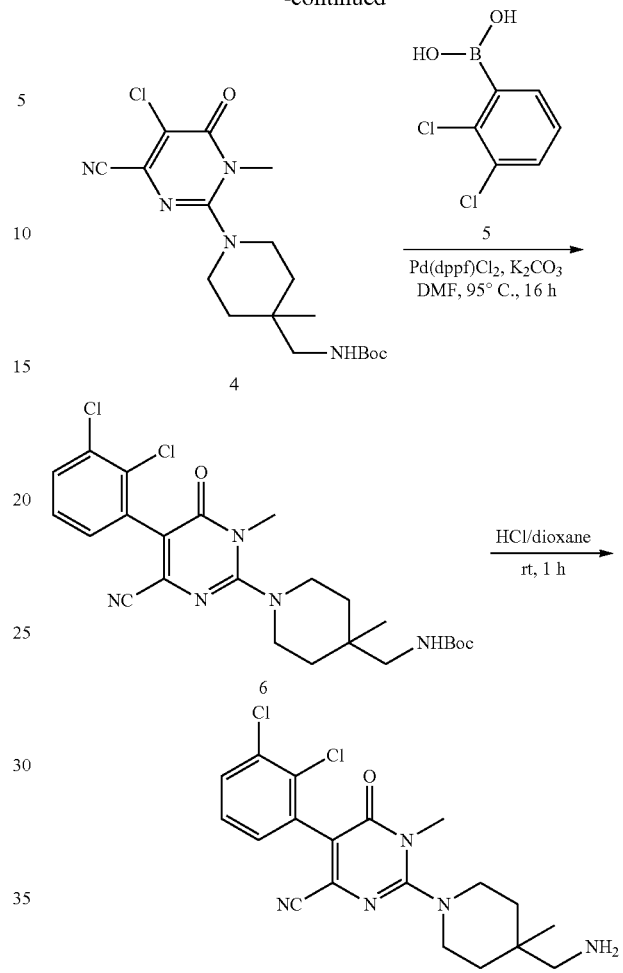

Step 1: Preparation of tert-butyl ((1-(4,5-dichloro-1-methyl-6-oxo-1,6-dihydropyrimidin-2-yl)-4-methyl-piperidin-4-yl)methyl)carbamate (3)

To a mixture of compound 1 (1.4 g, 1.0 eq) and compound 2 (1.5 g, 1.0 eq) in DMF (25 mL) was added DIEA (3.2 mL, 2.0 eq). The mixture was degassed and protected with nitrogen. The reaction was stirred at 80° C. for 2 h. EtOAc (150 mL) was added to the mixture under r.t. After standard work up procedure, the residue was purified by column chromatography to give compound 3 as a white solid (1.9 g, 71%).

Step 2: Preparation of tert-butyl ((1-(5-chloro-4-cyano-1-methyl-6-oxo-1,6-dihydropyrimidin-2-yl)-4-methylpiperidin-4-yl)methyl)carbamate (4)

A mixture of compound 3 (200 mg, 1.0 eq), Zn(CN)$_2$(57.9 g, 1.0 eq) and Pd(PPh$_3$)$_4$(56 mg, 0.1 eq) in DMF was stirred at 150° C. for 2 h, and the mixture was cooled to rt. EtOAc was added, after standard work up procedure the residue was purified by prep-TLC to give compound 4 as a white solid (60 mg, 31%).

Step 3: Preparation of tert-butyl ((1-(4-cyano-5-(2,3-dichlorophenyl)-1-methyl-6-oxo-1,6-dihydropyrimidin-2-yl)-4-methylpiperidin-4-yl)methyl)carbamate (6)

To a mixture of compound 4 (60 mg, 1.0 eq), K₂CO₃ (42 mg, 2 eq) and compound 5 (86 mg, 3.0 eq) in DMF (10 mL) was added Pd(dppf)Cl₂ (11 mg, 0.1 eq). The resulting mixture was stirred at 95° C. overnight. The mixture was diluted with EtOAc. After standard work up procedure, the residue was purified by prep-TLC to give compound 6 as a white solid (20 mg, 26%).

Step 4: Preparation of 2-(4-(aminomethyl)-4-methylpiperidin-1-yl)-5-(2,3-dichlorophenyl)-1-methyl-6-oxo-1,6-dihydropyrimidine-4-carbonitrile HCl/dioxane (0.5 mL, 10.0 eq) was added to a solution of compound 6 (19 mg, 1.0 eq) in DCM (5.0 mL), and then the reaction was stirred at rt for 1 h. The mixture was concentrated and neutralized with ammonium hydroxide, purified by prep-HPLC to give the desired compound as a white solid (2.5 mg, 17%). LC-MS: [M+H]⁺: 406.1. ¹H NMR (400 MHz, CD₃OD) δ 7.65 (dd, J=8.0, 1.6 Hz, 1H), 7.40 (t, J=8.0 Hz, 1H), 7.33 (dd, J=8.0, 1.2 Hz, 1H), 3.55-3.48 (m, 4H), 3.34-3.31 (m, 2H), 2.66 (s, 1H), 1.71-1.66 (m, 2H), 1.55-1.52 (m, 2H), 1.10 (s, 3H).

Example 2

Preparation of 3-(4-(aminomethyl)-4-methylpiperidin-1-yl)-6-(2,3-dichlorophenyl)pyrazin-2(1H)-one

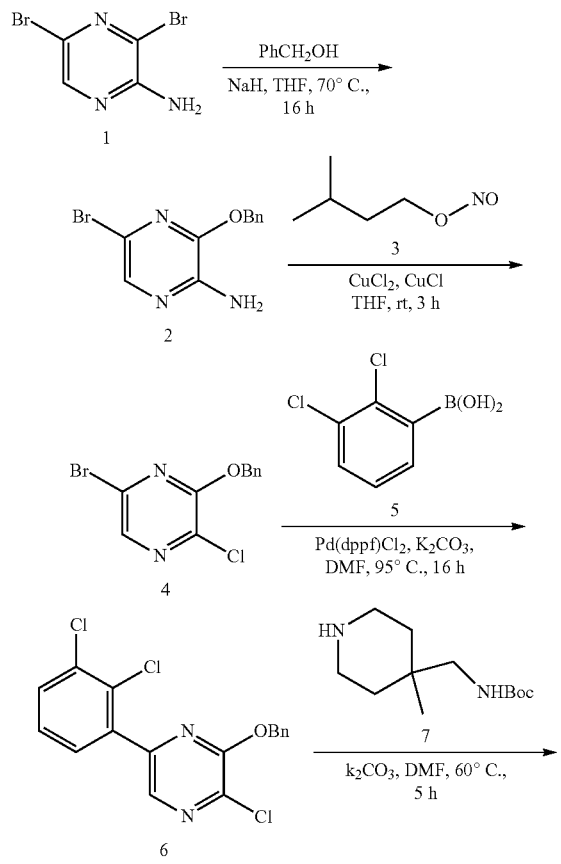

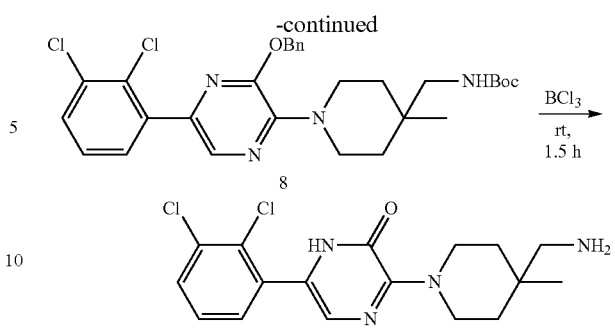

Step 1: Preparation of 3-(benzyloxy)-5-bromopyrazin-2-amine (2)

To a solution of benzyl alcohol (13.5 g, 1.05 eq) in THF (300 mL) was added NaH (60%, 5.7 g, 1.2 eq) at rt. The mixture was stirred at rt for 30 min. Compound 1 (30.0 g, 118 mmol, 1.0 eq) was added to the mixture. The mixture was heated to 70° C. and stirred overnight. The reaction was quenched by water, worked up under standard operation to give compound 2 as a yellow solid (25.0 g, 75%).

Step 2: Preparation of 3-(benzyloxy)-5-bromo-2-chloropyrazine (4)

To a solution of compound 2 (9.0 g, 1.0 eq) in THF (30 mL) was added CuCl₂ (12.96 g, 3.0 eq) and CuCl (5.75 g, 2.0 eq) at rt. Compound 3 (12.9 mL, 3.0 eq) was added dropwise to the mixture 10 min later. The reaction was worked up under standard operation to give compound 4 as a yellow oil (4.0 g, 41%).

Step 3: Preparation of 3-(benzyloxy)-2-chloro-5-(2,3-dichlorophenyl)pyrazine (6)

To a solution of compound 4 (3.0 g, 1.0 eq) in DMF (30 mL) was added K₂CO₃ (4.14 g, 3.0 eq), compound 5 (1.9 g, 1.0 eq) and Pd(dppf) Cl₂ (0.73 g, 0.1 eq). The resulting mixture was stirred at 95° C. under N₂ atmosphere overnight. The reaction was quenched by water and worked up under standard operation to give compound 6 as a yellow solid (1.5 g, 40%).

Step 4: Preparation of tert-butyl ((1-(3-(benzyloxy)-5-(2,3-dichlorophenyl)pyrazin-2-yl)-4-methylpiperidin-4-yl)methyl)carbamate (8)

To a solution of compound 6 (500 mg, 1.0 eq) in DMF (5 mL) were added compound 7 (342 mg, 1.1 eq) and K₂CO₃ (660 mg, 3.5 eq). The mixture was stirred at 60° C. under N₂ atmosphere for 5 h. The reaction was quenched by water and worked up under standard operation to give compound 8 as a white solid (400 mg, 53%).

Step 5: Preparation of 3-(4-(aminomethyl)-4-methylpiperidin-1-yl)-6-(2,3-dichlorophenyl)-pyrazin-2(1H)-one To a solution of compound 8 (100 mg, 1.0 eq) in DCM (5 mL) was added BCl₃ (1M in DCM, 5.0 eq). The mixture was stirred at rt for 1.5 h. The reaction was quenched by MeOH (5 mL) and the mixture was concentrated and purified by prep-HPLC to give target compound as a white solid (7 mg, 10%). LC-MS: [M+H]$^+$=367. $^1$H NMR (400 MHz, DMSO-d$_6$) δ 7.67 (d, J=7.4 Hz, 1H), 7.52-7.34 (m, 2H), 6.91 (s, 1H), 4.10-4.03 (m, 2H), 3.45-3.32 (m, 2H), 2.88 (d, J=6.0 Hz, 1H), 2.39 (s, 1H), 1.50-1.41 (m, 2H), 1.26-1.24 (m, 2H), 0.90 (d, J=9.2 Hz, 3H).

Example 3

Preparation of 3-(4-(aminomethyl)-4-methylpiperidin-1-yl)-6-((2,3-dichlorophenyl)thio)-1-methylpyrazin-2(1H)-one

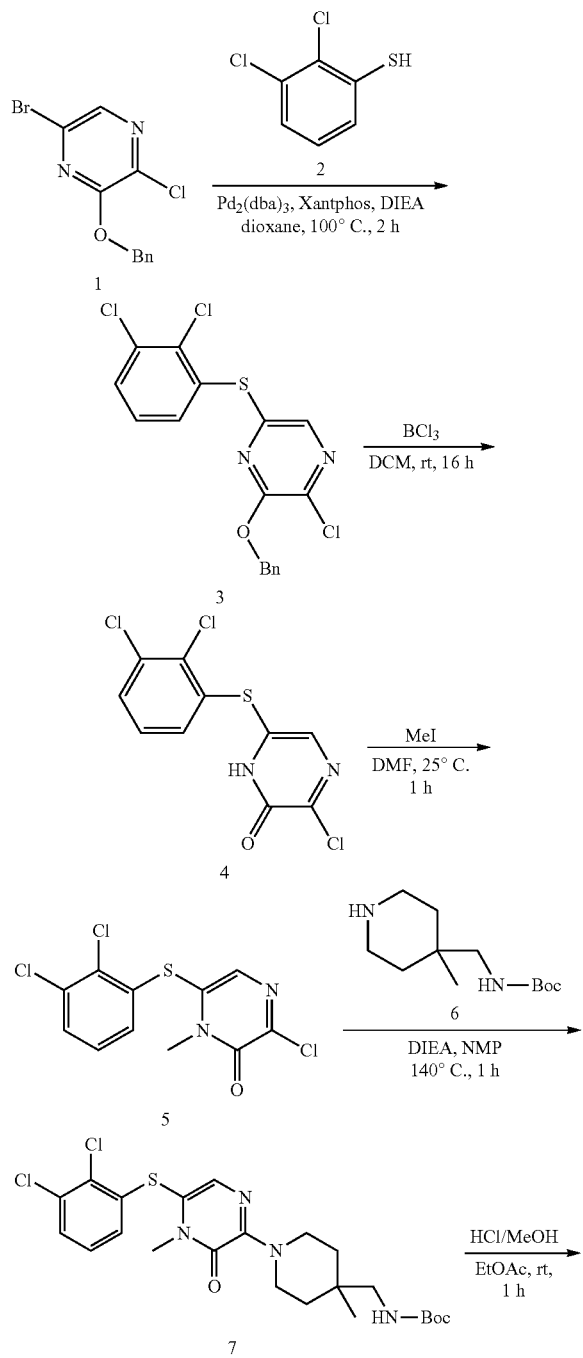

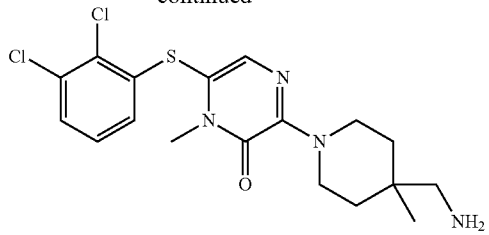

Step 1: Preparation of 3-(benzyloxy)-2-chloro-5-((2,3-dichlorophenyl)thio)pyrazine (3)

To a mixture of compound 1 (3.0 g, 1.0 eq), compound 2 (1.79 g, 1.0 eq), Pd$_2$(dba)$_3$ (300 mg) and Xantphos (300 mg) in dioxane (50 mL) was added DIEA (3.0 mL, 1.8 eq), and then the mixture was degassed and protected with nitrogen. EtOAc (150 mL) was added to the mixture 2 hours later. After standard work up procedure the residue was purified by column chromatography to give compound 3 as a colorless oil (2.9 g, 73%).

Step 2: Preparation of 3-chloro-6-((2,3-dichlorophenyl)thio)pyrazin-2(1H)-one (4)

BCl$_3$ (10.0 mL, 1M in DCM, 1.99 eq) was added to a solution of compound 3 (2.0 g, 1.0 eq) in DCM at rt and then the reaction was stirred at rt overnight. The reaction was quenched by sat. NaHCO$_3$ and stirred for 1 h. The suspension was then filtered and the solid was washed with DCM and water. The solid was dried to give the crude product 4 as a yellow solid. (3.0 g, 78%).

Step 3: Preparation of 3-chloro-6-((2,3-dichlorophenyl)thio)-1-methylpyrazin-2(1H)-one (5)

MeI (1 mL) was added to a mixture of crude 4 (2.0 g, 1.0 eq) and K$_2$CO$_3$ (2.0 g, 5.6 eq) in DMF (10 mL) and the resulting mixture was stirred at 25° C. for 1 h. The mixture was diluted with EtOAc and then was washed with brine. The organic solution was dried over Na$_2$SO$_4$ and concentrated. The residue was purified by column chromatography to give compound 5 as a white solid (505 mg, 60%).

Step 4: Preparation of tert-butyl ((1-(5-((2,3-dichlorophenyl)thio)-4-methyl-3-oxo-3,4-dihydropyrazin-2-yl)-4-methylpiperidin-4-yl)methyl)carbamate (7)

A mixture of compound 5 (96 mg, 1.0 eq), compound 6 (73 mg, 1.07 eq) and DIEA (0.7 mL, 1.8 eq) in NMP (2 mL) was stirred at 140° C. for 1 h. The mixture was diluted with EtOAc and then washed with brine. The organic solution was dried over Na$_2$SO$_4$ and concentrated. The residue was purified by column chromatography to give compound 7 as an off-shite solid (140 mg, 91%)

Step 3: Preparation of 3-(4-(aminomethyl)-4-methylpiperidin-1-yl)-6-((2,3-dichlorophenyl)thio)-1-methylpyrazin-2(1H)-one HCl/MeOH (1.0 mL, 10.0 eq) was added to the solution of compound 7 (51 mg, 1.0 eq) in EtOAc (2.0 mL) and then the reaction was stirred at rt for 1 h. The reaction solution was kept for 2 days and the obtained suspension was filtered. The solid was washed with EtOAc and the solid was dried to give the desired compound as HCl salt, white solid (24 mg, 53%). LC-MS: [m+H]+: 413.1. $^1$H NMR (400 MHz, CD$_3$OD) δ 7.45 (d, 0.1=8.0 Hz, 1H), 7.30-7.25 (m, 2H), 7.09 (d, J=8.0 Hz, 1H), 4.48-4.43 (m, 2H), 3.88-3.81 (m, 2H), 3.46 (s, 3H), 2.96 (s, 2H), 1.81-1.67 (m, 4H), 1.23 (s, 3H).

The compounds in Table A below were synthesized in the similar manner using appropriate reagents and conditions. The compounds listed in Table A are merely non-limiting examples. Other subject compounds could also be made using similar methods.

TABLE A

| Compound ID | $^1$H-NMR & MS [M + 1]$^+$ |
|---|---|
| 7 | LC-MS: [M + H]$^+$: 385.1<br>$^1$H NMR (400 MHz, CD$_3$OD) δ 7.34 (d, J = 8.4 Hz, 1H), 7.20 (t, J = 8.0 Hz, 1H), 7.13 (s, 1H), 6.93 (d, J = 7.6 Hz, 1H), 4.00-3.90 (m, 2H), 3.80-3.66 (m, 2H), 2.72 (s, 2H), 1.96-1.85 (m, 1H), 1.77-1.72 (m, 1H), 1.15 (s, 3H). |
| 2 | LC-MS: [M + H]$^+$: 399.1<br>$^1$H NMR (400 MHz, DMSO-d$_6$) δ 12.11 (br s, 1H), 7.97 (br s, 3H), 7.49 (d, J = 8.0 Hz, 1H), 7.35-7.31 (m, 1H), 7.22 (s, 1H), 6.95 (d, J = 8.0 Hz, 1H), 4.27-4.24 (m, 2H), 3.58-3.53 (m, 2H), 2.76 (s, 2H), 1.58-1.41 (m, 4H), 1.08 (s, 3H). |
| 4 | LC-MS: [M + H]$^+$: 383<br>$^1$H NMR (400 MHz, CD$_3$OD) δ 8.57 (s, 1H), 7.33 (d, J = 8.0 Hz, 1H), 7.26 (t, J = 8.0 Hz, 1H), 7.06 (d, J = 7.6 Hz, 1H), 6.96 (s, 1H), 3.67 (br s, 2H), 3.15 (br s, 2H), 2.86 (br s, 2H), 1.66 (s, 2H), 1.53-1.50 (m, 2H), 1.12 (s, 3H). |
| 6 | LC-MS: [M + H]$^+$: 397<br>$^1$H NMR (400 MHz, CD3OD) δ 7.47 (d, J = 8.4 Hz, 1H), 7.37 (t, J = 8.4 Hz, 1H), 7.21 (d, J = 8.4 Hz, 1H), 6.42 (s, 1H), 3.94-3.91 (m, 2H), 3.53 (s, 3H), 3.28-3.25 (m, 2H), 2.86 (br s, 2H), 1.68-1.61 (m, 2H), 1.54-1.51 (m, 2H), 1.13 (s, 3H). |
| 5 | LC-MS: [M + H]$^+$: 382.2<br>$^1$H NMR (400 MHz, CD$_3$OD) δ 7.14 (t, J = 8.0 Hz, 1H), 7.03 (d, J = 8.0 Hz, 1H), 6.95-6.90 (m, 2H), 4.03-3.96 (m, 2H), 3.40-3.31 (m, 2H), 2.90 (s, 2H), 1.70-1.64 (m, 2H), 1.69-1.63 (m, 2H), 1.16 (s, 3H). |
| 12 | LC-MS: [M + H]$^+$: 381.2<br>$^1$H NMR (400 MHz, CD$_3$OD) δ 8.53 (s, 1H), 8.34 (d, J = 8.4 Hz, 1H), 7.91 (d, J = 7.6 Hz, 1H), 7.82 (d, J = 8.0 Hz, 1H), 7.64-7.51 (m, 2H), 7.51-7.37 (m, 2H), 7.17 (s, 1H), 4.29-4.24 (m, 2H), 3.48-3.42 (m, 2H), 2.85 (s, 2H), 1.67-1.55 (m, 2H), 1.52-1.48 (m, 2H), 1.15 (s, 3H). |
| 8 | LC-MS: [M + H]$^+$: 383<br>$^1$H NMR (400 MHz, DMSO) δ 7.46 (d, J = 8.0 Hz, 1H), 7.32 (d, J = 8.0 Hz, 1H), 7.13 (s, 1H), 6.94 (d, J = 8.4 Hz, 1H), 3.99-3.97 (m, 2H), 3.68-3.65 (m, 2H), 2.95-2.91 (m, 2H), 2.76-2.74 (m, 2H), 2.66-2.63 (m, 2H). |
| 9 | LC-MS: [M + H]$^+$: 369.1<br>$^1$H NMR (400 MHz, CD$_3$OD) δ 7.35 (dd, J = 8.0, 1.2 Hz, 1H), 7.20 (t, J = 8.0 Hz, 1H), 7.11 (s, 1H), 6.93 (dd, J = 8.0, 1.2 Hz, 1H), 5.27-5.22 (m, 1H), 4.42-4.38 (m, 1H), 3.95-3.91 (m, 1H), 3.63-3.60 (m, 1H), 3.29-3.25 (m, 1H), 3.24-3.20 (m, 1H), 2.88-2.85 (m, 1H), 2.79-2.77 (m, 1H). |
| 11 | LC-MS: [M + H]$^+$: 371<br>$^1$H NMR (400 MHz, DMSO-d$_6$) δ 8.32 (s, 1H), 7.53 (d, J = 7.6 Hz, 1H), 7.48-7.46 (m, 1H), 7.31 (t, J = 8.0 Hz, 1H), 7.14 (s, 1H), 6.96-6.93 (m, 1H), 3.96-3.94 (m, 1H), 3.11-3.08 (m, 2H), 2.74-2.67 (m, 2H), 1.88-1.85 (m, 2H), 1.65-1.56 (m, 2H). |
| 17 | LC-MS: [M + H]+: 399.2<br>$^1$H NMR (400 MHz, CD$_3$OD) δ 8.53 (s, 1H), 7.71 (d, J = 7.6 Hz, 1H), 7.51 (t, J = 7.6 Hz, 1H), 7.36 (t, J = 7.6 Hz, 1H), 7.24 (d, J = 8.0 Hz, 1H), 7.21 (s, 1H), 4.39-4.34 (m, 2H), 3.57-3.50 (m, 2H), 2.86 (s, 2H), 1.65-1.59 (m, 2H), 1.55-1.51 (m, 2H), 1.17 (s, 3H). |
| 19 | LC-MS: [M + H]$^+$: 380.2<br>$^1$H NMR (400 MHz, CD$_3$OD) δ 7.20 (s, 1H), 7.07 (d, J = 8.6 Hz, 1H), 6.53 (dd, J = 8.4, 2.6 Hz, 1H), 6.38 (d, J = 2.6 Hz, 1H), 4.35-4.32 (m, 2H), 3.54-3.48 (m, 2H), 2.89 (s, 4H), 1.70-1.45 (m, 4H), 1.17 (s, 3H). |
| 21 | LC-MS: [M + H]$^+$: 380<br>$^1$H NMR (400 MHz, MeOD) δ 8.53 (s, 1H), 7.19 (s, 1H), 6.94 (t, J = 8.0 Hz, 1H), 6.66 (dd, J = 8.1, 1.2 Hz, 1H), 6.26 (dd, J = 7.8, 1.2 Hz, 1H), 4.42-4.24 (m, 2H), 3.51 (m, 2H), 2.86 (s, 2H), 1.61 (m, 2H), 1.52 (m, 2H), 1.16 (s, 3H). |
| 10 | LC-MS: [M + H]$^+$: 427<br>$^1$H NMR (400 MHz, DMSO) δ 8.26 (s, 1H), 7.48 (dd, J = 6.8 Hz, 1.2 Hz, 1H), 7.33 (t, J = 8.0 Hz, 1H), 7.22 (s, 1H), 6.95 (dd, J = 6.8 Hz, 1.2 Hz, 1H), 4.47-4.43 (m, 2H), 3.95 (t, J = 8.4 Hz, 1H), 3.71 (d, J = 8.4 Hz, 1H), 3.61 (d, J = 8.8 Hz, 1H), 3.30-3.28 (m, 3 H), 3.09-3.07 (m, 1H), 1.70-1.61 (m, 2H), 1.44-1.43 (m, 2H). |
| 18 | LC-MS: [M + H]$^+$: 400<br>$^1$H NMR (400 MHz, DMSO) δ 8.52 (d, J = 3.2 Hz, 1H), 8.31 (s, 1H), 7.39-7.62 (m, 2H), 7.22 (s, 1H), 4.24-4.21 (m, 2H), 3.57-3.48 (m, 2H), 2.58 (s, 2H), 1.53-1.47 (m, 2H), 1.36-1.33 (m, 2H), 0.99 (s, 3H). |
| 20 | LC-MS: [M + H]$^+$: 381.2<br>$^1$H NMR (400 MHz, CD$_3$OD) δ 7.52 (d, J = 2.8 Hz, 1H), 7.23 (s, 1H), 6.71 (d, J = 2.8 Hz, 1H), 4.28-4.23 (m, 2H), 3.53-3.47 (m, 2H), 2.61 (s, 2H), 1.62-1.55 (m, 2H), 1.47-1.43 (m, 2H), 1.07 (s, 3H). |
| 24 | LC-MS: [M + H]$^+$: 396<br>$^1$H NMR (400 MHz, MeOD) δ 8.51 (s, 1H), 7.88 (d, J = 5.5 Hz, 1H), 7.25 (s, 1H), 6.50 (d, J = 5.5 Hz, 1H), 4.41 (d, J = 13.9 Hz, 2H), 3.97 (s, 3H), 3.56 (m, 2H), 2.88 (s, 2H), 1.61 (m, 4H), 1.18 (s, 3H). |
| 69 | LC-MS: [M + H]$^+$: 403.2<br>$^1$H NMR (400 MHz, CD$_3$OD) δ 8.50 (s, 1H), 7.37 (dd, J = 8.0, 1.4 Hz, 1H), 7.26 (s, 1H), 7.21 (t, J = 8.0 Hz, 1H), 6.94 (dd, J = 8.0, 1.4 Hz, 1H), 4.82-4.79 (m, 2H), 3.37-3.34 (m, 2H), 3.14 (d, J = 19.8 Hz, 2H), 2.06-1.75 (m, 4H). |

TABLE A-continued

| Compound ID | ¹H-NMR & MS [M + 1]⁺ |
|---|---|
| 70 | LC-MS: [M + H]⁺: 437<br>¹H NMR (400 MHz, MeOD) δ 8.50 (s, 1H), 7.63 (dd, J = 8.0, 1.4 Hz, 1H), 7.42 (t, J = 7.8 Hz, 1H), 7.34 (dd, J = 7.6, 1.4 Hz, 1H), 4.68 (s, 2H), 4.36-4.24 (m, 1H), 4.05-3.92 (m, 1H), 3.85 (d, J = 9.1 Hz, 1H), 3.78-3.62 (m, 2H), 3.44 (t, J = 12.0 Hz, 1H), 3.08 (dt, J = 24.9, 6.9 Hz, 2H), 2.05-1.82 (m, 3H), 1.75 (d, J = 12.9 Hz, 1H), 1.32 (d, J = 6.5 Hz, 3H).1 |
| 71 | LC-MS: [M + H]⁺: 397<br>¹H NMR (400 MHz, MeOD) δ 8.54 (s, 1H), 7.35 (dd, J = 8.0, 1.4 Hz, 1H), 7.25-7.18 (m, 1H), 7.14 (s, 1H), 6.93 (dd, J = 8.0, 1.3 Hz, 1H), 3.30 (d, J = 1.6 Hz, 3H), 3.26 (s, 2H), 1.91 (s, 2H), 1.75 (t, J = 10.0 Hz, 2H), 1.62 (d, J = 9.2 Hz, 2H). |
| 72 | LC-MS: [M + H]⁺: 397<br>¹H NMR (400 MHz, DMSO) δ 8.36 (s, 1H), 7.47 (dd, J = 8.0, 1.3 Hz, 1H), 7.32 (t, J = 8.0 Hz, 1H), 7.12 (d, J = 5.2 Hz, 1H), 6.95 (d, J = 8.0 Hz, 1H), 5.67 (s, 1H), 3.53 (dd, J = 167.4, 77.9 Hz, 7H), 1.66 (dd, J = 37.8, 25.8 Hz, 4H), 1.44 (s, 2H). |
| 14 | LC-MS: [M + H]⁺: 441.2<br>¹H NMR (400 MHz, DMSO) δ 8.53 (s, 1H), 7.36 (d, J = 8.0 Hz, 1H), 7.21 (dd, J = 15.9, 7.8 Hz, 2H), 6.92 (d, J = 8.0 Hz, 1H), 4.65-4.39 (m, 2H), 4.35-4.14 (m, 1H), 3.92 (d, J = 8.9 Hz, 1H), 3.79 (d, J = 8.9 Hz, 1H), 3.31-3.21 (m, 3H), 2.01-1.57 (m, 4H), 1.27 (d, J = 6.4 Hz, 3H). |
| 15 | LC-MS: [M + H]⁺: 441.2<br>¹H NMR (400 MHz, DMSO) δ 8.53 (s, 1H), 7.36 (d, J = 8.0 Hz, 1H), 7.21 (dd, J = 15.9, 7.8 Hz, 2H), 6.92 (d, J = 8.0 Hz, 1H), 4.65-4.39 (m, 2H), 4.35-4.14 (m, 4H), 3.92 (d, J = 8.9 Hz, 1H), 3.79 (d, J = 8.9 Hz, 1H), 3.31-3.21 (m, 3H), 2.01-1.57 (m, 4H), 1.27 (d, J = 6.4 Hz, 3H). |
| 22 | LC-MS: [M + H]⁺: 381.2<br>¹H NMR (400 MHz, CD₃OD) δ 8.50 (s, 1H), 7.69 (d, J = 5.6 Hz, 1H), 7.23 (s, 1H), 6.17 (d, J = 5.6 Hz, 1H), 4.58 (s, 1H), 4.41 (d, J = 14.0 Hz, 2H), 3.64-3.48 (m, 2H), 2.89 (s, 2H), 1.63-1.58 (m, 4H), 1.18 (s, 3H). |
| 73 | LC-MS: [M + H]⁺: 427<br>¹H NMR (400 MHz, MeOD) δ 8.49 (s, 1H), 7.37 (d, J = 7.8 Hz, 1H), 7.22 (dd, J = 16.3, 8.3 Hz, 2H), 6.92 (d, J = 8.1 Hz, 1H), 4.69-4.52 (m, 2H), 4.15 (dd, J = 10.1, 5.8 Hz, 1H), 3.90 (dd, J = 18.7, 9.1 Hz, 2H), 3.73 (d, J = 10.3 Hz, 1H), 3.46 (s, 3H), 1.83 (d, J = 9.8 Hz, 2H), 1.71 (d, J = 13.8 Hz, 2H). |
| 75 | LC-MS: [M + H]⁺: 427<br>¹H NMR (400 MHz, MeOD) δ 8.53 (s, 1H), 7.36 (dd, J = 8.0, 1.3 Hz, 1H), 7.22 (dd, J = 15.0, 7.0 Hz, 2H), 6.92 (dd, J = 8.1, 1.3 Hz, 1H), 4.71-4.50 (m, 2H), 4.13 (dd, J = 9.7, 6.1 Hz, 1H), 3.86 (s, 2H), 3.63 (dd, J = 9.7, 4.1 Hz, 1H), 3.35 (d, J = 11.1 Hz, 2H), 3.24-3.15 (m, 1H), 1.81 (td, J = 15.0, 4.0 Hz, 2H), 1.65 (d, J = 14.4 Hz, 2H). |
| 76 | LC-MS: [M + H]⁺: 403<br>¹H NMR (400 MHz, MeOD) δ 8.49 (s, 1H), 7.37 (dd, J = 8.0, 1.3 Hz, 1H), 7.30-7.17 (m, 2H), 6.94 (dd, J = 8.1, 1.3 Hz, 1H), 3.36-3.31 (m, 2H), 3.30-3.24 (m, 2H), 3.16 (d, J = 19.9 Hz, 2H), 2.04-1.72 (m, 4H). |
| 77 | LC-MS: [M + H]⁺: 423.2<br>¹H NMR (400 MHz, MeOD) δ 7.69 (d, J = 5.4 Hz, 1H), 7.24 (s, 1H), 6.17 (d, J = 5.5 Hz, 1H), 4.65-4.55 (m, 4H), 4.35-4.22 (m, 1H), 3.94 (d, J = 9.0 Hz, 1H), 3.83 (d, J = 9.0 Hz, 1H), 3.31-3.21 (m, 1H), 1.93-1.49 (m, 4H), 1.28 (d, J = 6.5 Hz, 3H). |
| 78 | LC-MS: [M + H]⁺: 425<br>¹H NMR (400 MHz, MeOD) δ 7.36-7.34 (m, 1H), 7.22-7.18 (m, 2H), 6.92-6.90 (m, 1H), 4.38-4.34 (m, 1H).3.27-.325 (m, 2H), 3.10-3.03 (m, 2H), 2.16-2.13 (m, 1H), 1.97-1.87 (m, 1H), 1.87-1.66 (m, 8H), |
| 79 | LC-MS: [M + H]⁺: 437.2<br>¹H NMR (400 MHz, DMSO) δ 7.22 (s, 1H), 7.18 (t, J = 8.2 Hz, 1H), 6.91 (d, J = 8.2 Hz, 1H), 6.55 (d, J = 8.0 Hz, 1H), 4.70-4.60 (m, 4H), 4.30-4.27 (m, 1H), 3.97 (d, J = 9.2 Hz, 1H), 3.86 (d, J = 11.6 Hz, 1H), 3.41 (d, J = 4.1 Hz, 1H), 3.26-3.08 (m, 2H), 1.94-1.61 (m, 4H), 1.31 (d, J = 6.5 Hz, 3H). |
| 80 | LC-MS: [M + H]⁺: 438<br>¹H NMR (400 MHz, MeOD) δ 8.49 (s, 1H), 7.88 (d, J = 5.5 Hz, 1H), 7.25 (s, 1H), 6.50 (d, J = 5.5 Hz, 1H), 4.75-4.58 (m, 2H), 4.27 (dd, J = 6.5, 4.4 Hz, 1H), 4.06-3.90 (m, 4H), 3.84 (d, J = 9.1 Hz, 1H), 3.36 (s, 1H), 3.28-3.11 (m, 2H), 1.86 (dd, J = 17.1, 7.3 Hz, 3H), 1.67 (d, J = 13.5 Hz, 1H), 1.29 (d, J = 6.5 Hz, 3H). |
| 81 | LC-MS: [M + H]⁺: 442<br>¹H NMR (400 MHz, MeOD) δ 8.56-8.32 (m, 1H), 8.10 (d, J = 5.3 Hz, 1H), 7.40-7.19 (m, 1H), 6.95 (d, J = 5.3 Hz, 1H), 4.77-4.62 (m, 2H), 4.33-4.20 (m, 1H), 3.97 (d, J = 9.1 Hz, 1H), 3.86 (d, J = 9.1 Hz, 1H), 3.43 (t, J = 16.6 Hz, 1H), 3.23 (m, 2H), 1.96-1.79 (m, 3H), 1.69 (d, J = 13.2 Hz, 1H), 1.31 (d, J = 6.5 Hz, 3H). |
| 84 | LC-MS: [M + H]⁺: 410.3<br>¹H NMR (400 MHz, DMSO) δ 8.32 (s, 2H), 7.91 (d, J = 5.3 Hz, 1H), 7.25 (s, 1H), 7.05 (t, J = 5.1 Hz, 1H), 4.32-4.28 (m, 2H), 4.13-4.01 (m, 2H), 3.69 (d, J = 8.4 Hz, 1H), 3.51 (d, J = 8.5 Hz, 1H), 2.97 (d, J = 5.1 Hz, 1H), 1.79-1.65 (m, 2H), 1.59-1.42 (m, 2H), 1.10 (d, J = 6.4 Hz, 3H). |
| 107 | LC-MS: [M + H]⁺: 424<br>¹H NMR (400 MHz, MeOD) δ 8.52 (s, 1H), 7.35-7.18 (m, 2H), 5.98 (d, J = 7.1 Hz, 1H), 4.60 (m, 2H), 4.34-4.19 (m, 1H), 3.92 (d, J = 9.0 Hz, 1H), 3.81 (d, J = 9.0 Hz, 1H), 3.37 (d, J = 10.2 Hz, 1H), 3.28-3.18 (m, 2H), 1.84 (m, 3H), 1.66 (d, J = 13.3 Hz, 1H), 1.27 (d, J = 6.5 Hz, 3H). |
| 109 | LC-MS: [M + H]⁺: 425<br>¹H NMR (400 MHz, MeOD) δ 7.32 (m, 1H), 7.21m7.08 (m, 3H), 4.83m4.76 (m, 1H), 4.69 (d, J = 13.4 Hz, 1H), 4.32 (m, 1H), 4.01 (d, J = 9.2 Hz, 1H), 3.88 (d, J = 9.2 Hz, 1H), 3.70-3.46 (m, 3H), 2.09 (t, J = 10.7 Hz, 2H), 2.03-1.94 (m, 1H), 1.83 (d, J = 13.2 Hz, 1H), 1.33 (d, J = 6.5 Hz, 3H). |

TABLE A-continued

| Compound ID | ¹H-NMR & MS [M + 1]⁺ |
|---|---|
| 82 | LC-MS: [M + H]⁺: 409<br>¹H NMR (400 MHz, MeOD) δ 8.49 (s, 1H), 7.25 (s, 1H), 7.14 (m, 2H), 6.99 (m, 1H), 4.64-4.46 (m, 2H), 4.34-4.20 (m, 1H), 3.93 (d, J = 9.1 Hz, 1H), 3.82 (d, J = 9.1 Hz, 1H), 3.29-3.06 (m, 3H), 1.91-1.73 (m, 3H), 1.65 (d, J = 13.2 Hz, 1H), 1.28 (d, J = 6.5 Hz, 3H). |
| 83 | LC-MS: [M + H]⁺: 426.3<br>¹H NMR (400 MHz, DMSO) δ 8.26 (s, 1H), 8.03 (s, 1H), 7.27 (s, 1H), 6.98 (s, 1H), 4.45-4.31 (m, 2H), 4.15-4.09 (m, 1H), 3.75 (d, J = 8.6 Hz, 1H), 3.58 (d, J = 8.6 Hz, 1H), 3.20-3.10 (m, 3H), 1.86-1.41 (m, 4H), 1.13 (d, J = 6.5 Hz, 3H). |
| 26 | LC-MS: [M + H]⁺: 422<br>¹H NMR (400 MHz, MeOD) δ 7.36 (t, J = 8.0 Hz, 1H), 7.23 (s, 1H), 6.77 (t, J = 7.8 Hz, 2H), 4.43-4.29 (m, 2H), 3.54 (m, 2H), 2.89 (s, 2H), 1.70-1.59 (m, 2H), 1.54 (d, J = 13.7 Hz, 2H), 1.18 (s, 3H). |
| 85 | LC-MS: [M + H]⁺: 439<br>¹H NMR (400 MHz, DMSO) δ 7.53-7.48 (m, 1H), 7.33 (t, J = 8.0 Hz, 1H), 6.85 (d, J = 7.9 Hz, 1H), 6.74 (d, J = 7.4 Hz, 1H), 6.60 (d, J = 7.5 Hz, 1H), 4.31-4.06 (m, 1H), 3.79 (d, J = 8.8 Hz, 1H), 3.70-3.47 (m, 3H), 3.28 (s, 1H), 2.73-2.58 (m, 2H), 1.79 (m, 2H), 1.62 (dm, 2H), 1.21 (t, J = 10.4 Hz, 3H). |
| 13 | LC-MS: [M + H]⁺: 437.1<br>¹H NMR (400 MHz, DMSO) δ 7.48 (d, J = 7.4 Hz, 1H), 7.32 (t, J = 8.0 Hz, 1H), 7.21 (d, J = 1.2 Hz, 1H), 6.94 (m, 1H), 4.79-4.45 (m, 2H), 3.38 (d, J = 5.4 Hz, 1H), 3.21-2.81 (m, 3H), 2.09-1.71 (m, 2H), 1.70-1.32 (m, 6H), 0.75-0.33 (m, 2H) |
| 86 | LC-MS: [M + H]⁺: 369.0<br>¹H NMR (400 MHz, MeOD) δ 7.42 (d, J = 7.8 Hz, 1H), 7.33-7.12 (m, 2H), 7.05 (s, 1H), 4.72-4.16 (m, 2H), 4.21-3.92 (m, 2H), 2.60 (s, 1H), 2.33 (s, 2H). |
| 108 | LC-MS: [M + H]⁺: 473.1<br>¹H NMR (400 MHz, DMSO) δ 12.16 (s, 1H), 8.47 (s, 3H), 7.58 (d, J = 7.3 Hz, 1H), 7.50 (dd, J = 8.0, 1.3 Hz, 1H), 7.39-7.17 (m, 5H), 6.98 (m, 1H), 4.76 (s, 2H), 4.35 (d, J = 5.1 Hz, 1H), 3.33-3.13 (m, 3H), 3.00 (d, J = 16.2 Hz, 1H), 1.88-1.74 (m, 2H), 1.52 (t, J = 15.3 Hz, 2H). |
| 87 | LC-MS: [M + H]⁺: 475.1<br>¹H NMR (400 MHz, MeOD) δ 7.54 (d, J = 7.4 Hz, 1H), 7.41 (m, 2H), 7.24 (d, J = 16.0 Hz, 2H), 7.12-7.04 (m, 2H), 7.00 (d, J = 8.2 Hz, 1H), 5.11 (d, J = 12.3 Hz, 1H), 4.83-4.76 (m, 1H), 4.68 (s, 1H), 3.70-3.41 (m, 2H), 2.28 (td, J = 12.9, 4.6 Hz, 1H), 2.10 (m, 1H), 2.03-1.87 (m, 2H). |
| 88 | LC-MS: [M + H]⁺: 428.1<br>¹H NMR (400 MHz, CD₃OD) δ 8.17 (d, J = 4.4 Hz, 1H), 7.27-7.20 (m, 2H), 4.68-4.63 (m, 1H), 4.22-4.18 (m, 1H), 4.00-3.83 (m, 3H), 3.73-3.57 (m, 4H), 2.09-2.01 (m, 2H), 1.92-1.84 (m, 2H) |
| 27 | LC-MS: [M + H]⁺: 492.2<br>¹H NMR (400 MHz, MeOD) δ 8.18 (d, J = 8.3 Hz, 1H), 7.47 (t, l = 8.2 Hz, 1H), 7.10 (s, 1H), 7.03 (d, J = 7.9 Hz, 1H), 4.78 (s, 1H), 4.68-4.45 (m, 3H), 4.30 (m, 1H), 3.99 (d, J = 9.3 Hz, 1H), 3.88 (d, J = 9.2 Hz, 1H), 3.57-3.42 (m, 3H), 2.28 (s, 3H), 2.09-1.92 (m, 3H), 1.79 (d, J = 13.8 Hz, 1H), 1.32 (d, J = 6.5 Hz, 3H). |

Example 4

Preparation of 6-(4-(aminomethyl)-4-methylpiperidin-1-yl)-3-((2,3-dichlorophenyl)amino)-1,5-dihydro-4H-pyrazolo[3,4-d]pyrimidin-4-one

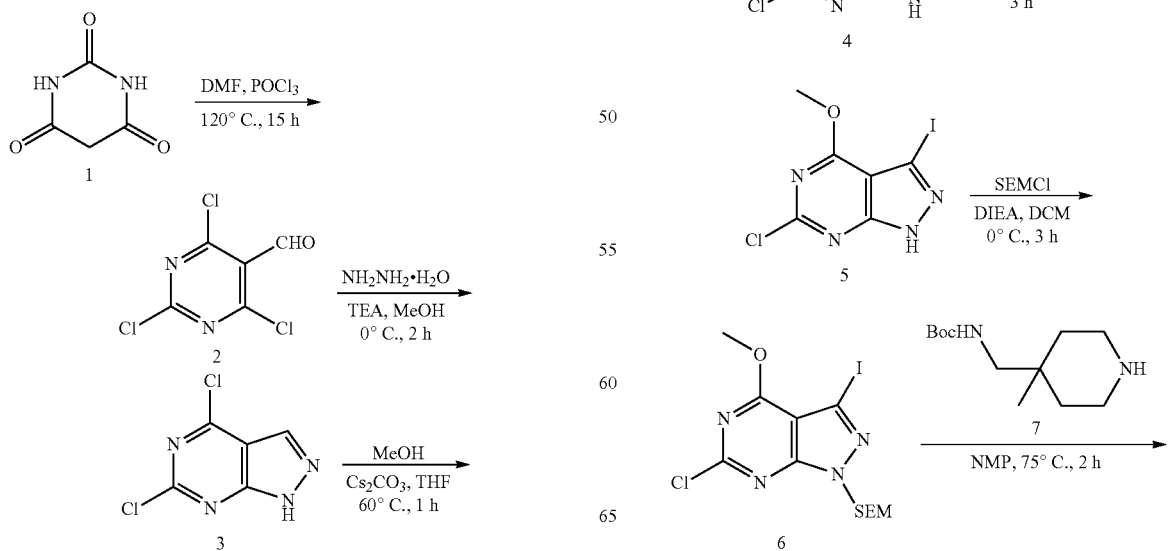

-continued

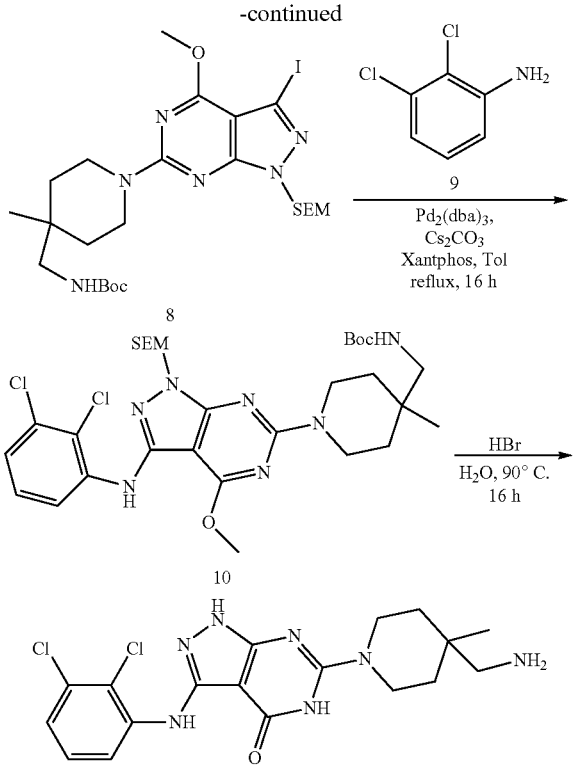

Step 1: Preparation of 2,4,6-trichloropyrimidine-5-carbaldehyde (2)

A mixture of compound 1 (25.6 g, 1.0 eq) with POCl$_3$ (100 mL) and DMF (30 mL) was heated at 120° C. for 15 h, and then DMF was evaporated. Ice water was added to the residue and the solid formed was collected and dried to give compound 2 (9.2 g, 21%).

Step 2: Preparation of 4,6-dichloro-1H-pyrazolo[3,4-d]pyrimidine (3)

To a solution of compound 2 (16.0 g, 1.0 eq) in methanol (80 mL) was added dropwise a solution of hydrazine monohydrate (4.55 g, 1.2 eq) in methanol at 0° C., and then a solution of triethylamine (15.28 g, 2.0 eq) in methanol was added dropwise at 0° C. The mixture was stirred at 0° C. for 2 h, then evaporated in vacuo. The residue was suspended in hot isopropyl alcohol and the insoluble materials were removed by filtration. The combined filtrate was concentrated in vacuo to give the title compound 3 as a yellow solid (9.0 g, 62%).

Step 3: Preparation of 6-chloro-4-methoxy-1H-pyrazolo[3,4-d]pyrimidine (4)

To a solution of compound 3 (480 mg, 2.54 mmol, 1.0 eq) in THF was added cesium carbonate (1.65 g, 2.0 eq) and methanol (3.0 mL), and the mixture was heated to 60° C. The reaction was quenched with water (10 mL) and worked up under standard procedure to afford compound 4 as a brown solid (468 mg, 99%).

Step 4: Preparation of 6-chloro-3-iodo-4-methoxy-1H-pyrazolo[3,4-d]pyrimidine (5)

To a solution of compound 4 (468 mg, 1.0 eq) in dry DMF (12 mL) was added N-iodosuccinimide (857 mg, 1.5 eq) and the reaction mixture was heated to 80° C. under stirring for 3 h. The reaction was quenched with water (10 mL) and worked up under standard process to afford compound 5 as a brown solid (522 mg, 66%).

Step 5: Preparation of 6-chloro-3-iodo-4-methoxy-1-((2-(trimethylsilyl) ethoxy)methyl)-1H-pyrazolo[3,4-d]pyrimidine (6)

To a solution of compound 5 (2.6 g, 1.0 eq) in DCM (20 mL) was added DIEA (2.37 g, 2.2 eq) at 0° C., and then SEMCl (1.67 g, 1.2 eq) was added dropwise. The reaction was quenched with water (10 mL) and worked up under standard process to afford compound 6 as a brown solid (1.55 g, 42%).

Step 6: Preparation of tert-butyl ((1-(3-iodo-4-methoxy-1-((2-(trimethylsilyl) ethoxy)methyl)-1H-pyrazolo [3,4-d]pyrimidin-6-yl)-4-methylpiperidin-4-yl)methyl) carbamate (8)

To a solution of compound 6 (520 mg, 1.0 eq) in NMP (10 mL) was added compound 7 (296 mg, 1.1 eq) at RT, and then the mixture was stirred at 75° C. for 2 h. The reaction was quenched with water (10 mL) and worked up under standard process to afford compound 8 as a white solid (450 mg, 60%).

Step 7: Preparation of tert-butyl ((1-(3-((2,3-dichlorophenyl)amino)-4-methoxy-1-((2-(trimethylsilyl) ethoxy)methyl)-1H-pyrazolo[3,4-d]pyrimidin-6-yl)-4-methylpiperidin-4-yl)methyl)carbamate (10)

To a solution of compound 8 (200 mg, 1.0 eq) in toluene was added compound 9 (61.5 mg, 1.2 eq), cesium carbonate (123.7 mg, 1.2 eq) and xantphos (183.1 mg, 1.0 eq). After that, Pd$_2$(dba)$_3$ (5.0 mg) was added under the atmosphere of Ar. The mixture was stirred at 120° C. for 16 h. The reaction was quenched with water and worked up under standard process to give compound 10 as a white solid (42 mg, 20%).

Step 8: Preparation of 6-(4-(aminomethyl)-4-methylpiperidin-1-yl)-3-((2,3-dichlorophenyl)amino)-1,5-dihydro-4H-pyrazolo[3,4-d]pyrimidin-4-one To a mixture of compound 10 (97.0 mg, 1.0 eq) in H$_2$O (4 mL) was added H Br (40%, 2 mL), and then the mixture was stirred at 90° C. for 16 h. The reaction was quenched by water followed by standard work up process. The crude product was purified by prep-HPLC to give desired compound, as HCOOH salt (white solid, 9.79 mg, 16%). LC-MS: [M+H]+=422.2. $^1$H NMR (400 MHz, CD$_3$OD): δ 8.53 (brs, 1H), 8.37 (d, J=8.8 Hz, 1H), 7.24 (t, J=8.4 Hz, 1H), 7.05 (d, J=8.0 Hz, 1H), 4.03-3.98 (m, 2H), 3.50-3.43 (m, 2H), 2.87 (s, 2H), 1.64-1.56 (m, 4H), 1.17 (s, 3H).

The compounds in Table B below were synthesized in the similar manner using appropriate reagents and conditions. The compounds listed in Table B are merely non-limiting examples. Other subject compounds could also be made using similar methods.

TABLE B

| Compound ID | ¹H-NMR & MS [M + 1]⁺ |
|---|---|
| 35 | LC-MS: [M + H]⁺: 423.1<br>¹H NMR (400 MHz, CD₃OD) δ 8.52 (br s, 3H), 7.38 (d, J = 8.0 Hz, 1H), 7.27 (t, J = 8.2 Hz, 1H), 7.14 (d, J = 8.8 Hz, 1H), 4.08-3.99 (m, 2H), 3.60-3.43 (m, 2H), 2.88 (s, 2H), 1.62-1.56 (m, 4H), 1.18 (s, 3H). |
| 68 | LC-MS: [M + H]⁺: 408<br>¹H NMR (400 MHz, DMSO) δ 12.21 (s, 1H), 8.67-8.21 (m, 3H), 7.96 (s, 1H), 7.34 (t, J = 8.2 Hz, 1H), 7.13 (d, J = 7.8 Hz, 1H), 3.55 (s, 2H), 3.44 (d, J = 10.9 Hz, 1H), 3.20 (d, J = 10.8 Hz, 1H), 2.58 (s, 2H), 1.89 (s, 1H), 1.66 (d, J = 5.5 Hz, 1H), 1.05 (s, 3H). |

Example 5

Preparation of (1-(3-((2,3-dichlorophenyl)thio)-1H-pyrazolo[3,4-d]pyrimidin-6-yl)-4-methylpiperidin-4-yl)methanamine

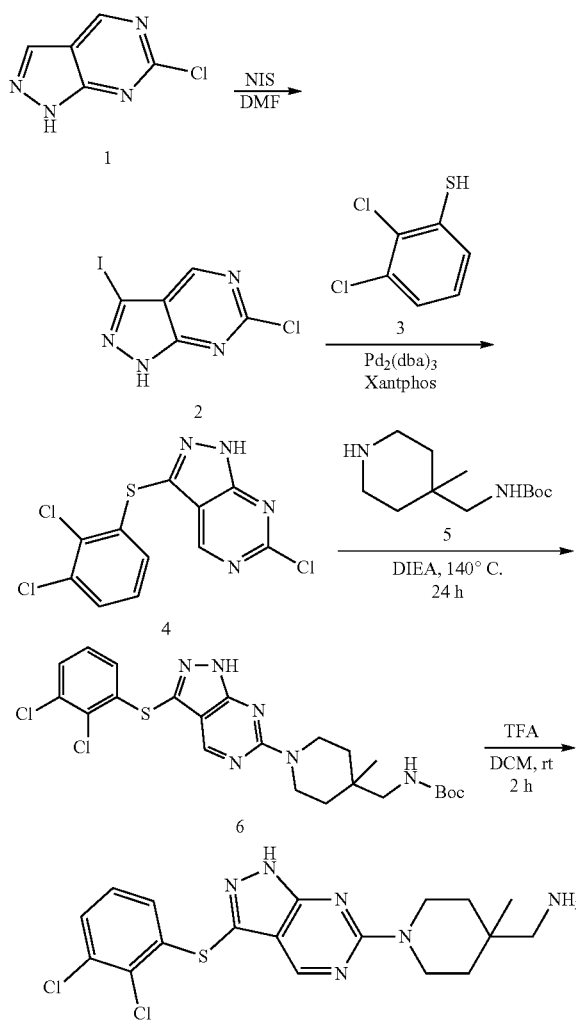

Step 1: Preparation of 6-chloro-3-iodo-1H-pyrazolo[3,4-d]pyrimidine (2)

To a solution of compound 1 (780 mg, 1.0 eq) in DMF was added NIS (1300 mg, 1.2 eq) in portion at rt. The mixture was heated to 80° C. and stirred for 4 h. The reaction was quenched by water and worked up under standard operation to afford compound 2 as yellow solid (560 mg, 68%).

Step 2: Preparation of 6-chloro-3-((2,3-dichlorophenyl)thio)-1H-pyrazolo[3,4-d]pyrimidine (4)

To a solution of compound 2 (280 mg, 1.0 eq) in dioxane were added Pd₂(dba)₃ (46 mg, 0.05 eq), XantPhos (58 mg, 0.1 eq) and DIEA (200 mg, 1.5 eq) at rt. The mixture was heated to 90° C. and stirred for 14 h. The reaction was quenched by water and worked up under standard operation to afford compound 4 as yellow solid (140 mg, 48%).

Step 3: Preparation of tert-butyl ((1-(3-((2,3-dichlorophenyl)thio)-1H-pyrazolo[3,4-d]pyrimidin-6-yl)-4-methylpiperidin-4-yl)methyl)carbamate (6)

To a solution of compound 4 (145 mg, 1.0 eq) in DIEA was added compound 5 (300 mg, 3.0 eq) at rt. The mixture was heated at 140° C. for 24 h. The reaction was quenched by water and worked up under standard operation to give compound 6 as a yellow oil (110 mg, 48%).

Step 4: Preparation of (1-(3-((2,3-dichlorophenyl)thio)-1H-pyrazolo[3,4-d]pyrimidin-6-yl)-4-methylpiperidin-4-yl)methanamine To a solution of compound 6 (110 mg, 1.0 eq) in DCM was added TFA (1 mL). The mixture was stirred at rt for 2 h. The mixture was concentrated and neutralized with ammonium hydroxide (pH=7-8), purified by prep-HPLC to give the target compound as a white solid (HCOOH salt, 6 mg, 7%). LC-MS: [M+H]⁺=423.2. ¹H NMR (400 MHz, CD₃OD) δ 8.54 (s, 1H), 7.41 (dd, J=8.0, 1.2 Hz, 1H), 7.14 (t, J=8.0 Hz, 1H), 6.92 (dd, J=8.0, 1.2 Hz, 1H), 4.62 (br, 1H), 4.42-4.36 (m, 2H), 3.61-3.54 (m, 2H), 2.89 (s, 2H), 1.60-1.50 (m, 4H), 1.20 (s, 3H).

Example 6

Preparation of 6-amino-5-((2,3-dichlorophenyl)thio)-2-(hexahydropyrrolo[3,4-c]pyrrol-2(1H)-yl)-3-methylpyrimidin-4(3H)-one

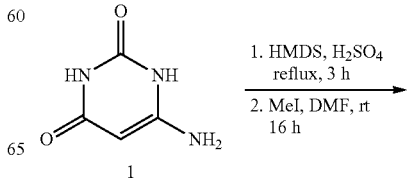

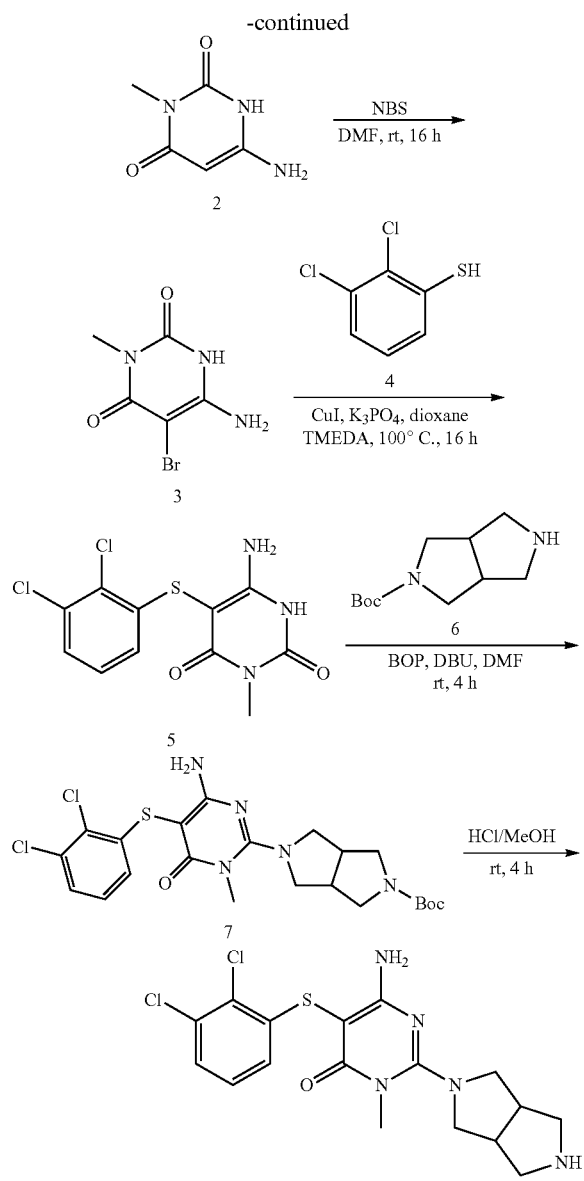

Step 1: Preparation of
6-amino-3-methylpyrimidine-2,4(1H,3H)-dione (2)

To a solution of compound 1 (31.08 g, 1.0 eq) in HMDS (150 mL) was added conc. H₂SO₄ (0.6 mL) at room temperature. The mixture was heated to reflux for 3 h. Then the mixture was concentrated in vacuo. The residue was dissolved in DMF (150 mL) and MeI (115.8 g, 3.4 eq) was added at rt. The mixture was stirred at rt for 16 h. The reaction was quenched by water and worked up under standard operation to give compound 2 as a white solid (16 g, 47%).

Step 2: Preparation of 6-amino-5-bromo-3-methyl-pyrimidine-2,4(1H,3H)-dione (3)

To a solution of compound 2 (5.0 g, 1.0 eq) in DMF (50 mL) was added NBS (7.9 g, 1.25 eq) and the mixture was stirred at rt overnight. The reaction was quenched by water and worked up under standard operation to give compound 3 as a white solid (4.7 g, 60%).

Step 3: Preparation of 6-amino-5-((2,3-dichlorophenyl)thio)-3-methylpyrimidine-2,4(1H,3H)-dione (5)

To a solution of compound 3 (500 mg, 1.0 eq) in dioxane (10 mL) was added compound 4 (813 mg, 2.0 eq), K₃PO₄ (1445 mg, 3.0 eq), TMEDA (105 mg, 0.4 eq) and CuI (86 mg, 0.2 eq). The resulting mixture was stirred at 100° C. under N₂ atmosphere for 2 h. The reaction was quenched by water and worked up under standard operation to give compound 5 as a brown solid (210 mg, 29%).

Step 4: Preparation of tert-butyl 5-(4-amino-5-((2,3-dichlorophenyl)thio)-1-methyl-6-oxo-1,6-dihydropyrimidin-2-yl)hexahydropyrrolo[3,4-c]pyrrole-2(1H)-carboxylate (7)

To a solution of compound 5 (60 mg, 1.0 eq) in DMF (2 mL) was added compound 6 (60 mg, 1.5 eq), BOP (250 mg, 3.0 eq) and DBU (143 mg, 5.0 eq). The reaction was quenched by water and worked up under standard operation to give compound 7 as a white solid (55 mg, 57%).

Step 5: Preparation of 6-amino-5-((2,3-dichlorophenyl)thio)-2-(hexahydropyrrolo[3,4-c]pyrrol-2(1H)-yl)-3-methylpyrimidin-4(3H)-one A solution of compound 7 (50 mg, 1.0 eq) in HCl/MeOH (3 M, 3 mL) was stirred at rt for 4 h. The mixture was concentrated and purified by pre-HPLC to give the desired compound as HCOOH salt (white solid, 21 mg, 53%). LC-MS: [M+H]+=412. ¹H NMR (400 MHz, CD₃OD) δ 8.52 (br s, 1H), 7.24 (dd, J=8.0, 1.2 Hz, 1H), 7.09 (t, 0.1=8.0 Hz, 1H), 6.75 (dd, J=8.0, 1.2 Hz, 1H), 3.74-3.61 (m, 4H), 3.60-3.50 (m, 2H), 3.45 (s, 3H), 3.30-3.13 (m, 4H).

The compounds in Table C below were synthesized in the similar manner using appropriate reagents and conditions. The compounds listed in Table C are merely non-limiting examples. Other subject compounds could also be made using similar methods.

TABLE C

| Compound ID | ¹H-NMR & MS [M + 1]⁺ |
|---|---|
| 52 | LC-MS: [M + H]⁺: 414.2<br>¹H NMR (400 MHz, CD₃OD) δ 7.23 (dd, J = 8.0, 1.2 Hz, 1H), 7.09 (t, J = 8.0 Hz, 1H), 6.76 (dd, J = 8.0, 1.2 Hz, 1H), 3.77-3.70 (m, 2H), 3.56 (d, J = 10.8 Hz, 1H), 3.42 (s, 3H), 3.34-3.24 (m, 1H), 2.69 (s, 2H), 1.95-1.84 (m, 1H), 1.82-1.70 (m, 1H), 1.15 (s, 3H). |
| 60 | LC-MS: [M + H]⁺: 398.1<br>¹H NMR (400 MHz, CD₃OD) δ 7.23 (dd, J = 8.0 Hz, 1.2 Hz, 1H), 7.10 (t, J = 8.0 Hz, 1H), 6.79 (d, J = 8.0 Hz, 1.2 Hz, 1H), 3.77-3.72 (m, 2H), 3.49-3.46 (m, 2H), 3.17-3.12 (m, 2H), 3.00 (br s, 2H), 2.82-2.80 (m, 2H). |
| 54 | LC-MS: [M + H]⁺: 400.1<br>¹H NMR (400 MHz, CD₃OD) δ 7.22 (d, J = 8.0 Hz, 1H), 7.10 (t, J = 8.0 Hz, 1H), 6.81 (d, J = 8.0 Hz, 1H), 3.61 (br s, 2H), 3.42-3.39 (m, 1H), 3.25-3.23 (m, 1H), 2.67 (s, 2H), 1.96-1.93 (m, 1H), 1.79-1.76 (m, 1H), 1.14 (s, 3H). |

TABLE C-continued

| Compound ID | ¹H-NMR & MS [M + 1]⁺ |
|---|---|
| 63 | LC-MS: [M + H]⁺: 426.1<br>¹H NMR (400 MHz, CD₃OD) δ 7.22 (d, J = 7.6 Hz, 1H), 7.09 (t, J = 8.0 Hz, 1H), 6.76 (d, J = 8.0 Hz, 1H), 4.25-4.19 (m, 2H), 4.16-4.10 (m, 2H), 3.39-3.31 (m, 1H), 3.30 (s, 3H), 2.32-2.27 (m, 1H), 2.10-1.92 (m, 3H), 1.71-1.66 (m, 1H), 1.49-1.45 (m, 1H). |
| 64 | LC-MS: [M + H]⁺: 398.1<br>¹H NMR (400 MHz, CD₃OD) δ 7.25 (d, J = 7.6 Hz, 1H), 7.10 (t, J = 7.6 Hz, 1H), 6.78 (d, J = 7.6 Hz, 1H), 3.94 (br s, 3H), 3.45-3.33 (m, 5H), 1.93 (br s, 2H). |
| 66 | LC-MS: [M + H]⁺: 384<br>¹H NMR (400 MHz, CD₃OD) δ 7.24 (d, J = 8.0 Hz, 1H), 7.11 (t, J = 8.0 Hz, 1H), 6.84 (d, J = 8.0 Hz, 1H), 3.76-3.72 (m, 2H), 3.66-3.63 (m, 2H), 2.52 (t, J = 7.2 Hz, 1H), 1.83-1.82 (m, 2H). |
| 67 | LC-MS: [M + H]⁺: 412.1<br>¹H NMR (400 MHz, CD₃OD) δ 7.23 (dd, J = 8.0 Hz, 2.0 Hz, 1H), 7.10 (t, J = 8.0 Hz, 1H), 6.79 (dd, J = 8.0 Hz, 2.0 Hz, 1H), 4.06-4.04 (m, 2H), 3.96-3.95 (m, 2H), 3.43-3.39 (m, 1H), 2.33-2.27 (m, 1H), 2.07-2.02 (m, 2H), 1.96-1.92 (m, 1H), 1.74-1.68 (m, 1H), 1.52-1.49 (m, 1H). |
| 58 | LC-MS: [M + H]⁺: 398.1<br>¹H NMR (400 MHz, CD₃OD) δ 7.22 (d, J = 8.0, 1H), 7.08 (t, J = 8.0 Hz, 1H), 6.76 (d, J = 8.0, 1H), 5.17-5.15 (m, 1H), 4.42 (t, J = 8.4 Hz, 1H), 4.09-4.05 (m, 1H), 3.36 (s, 3H), 3.31-3.27 (m, 1H), 3.18 (d, J = 12.0 Hz, 1H), 3.08-3.05 (m, 1H), 2.77-2.72 (m, 1H), 2.62-2.61 (m, 1H), 2.59-2.58 (m, 1H). |
| 59 | LC-MS: [M + H]⁺: 384.1<br>¹H NMR (400 MHz, CD₃OD) δ 7.22 (d, J = 8.0 Hz, 1H), 7.10 (t, J = 8.0 Hz, 1H), 6.79 (d, J = 8.0 Hz, 1H), 4.94-4.91 (m, 1H), 4.17 (t, J = 8.8 Hz, 1H), 3.71-3.68 (m, 1H), 3.45 (d, J = 12.8 Hz, 1H), 3.15-3.11 (m, 2H), 2.74-2.70 (m, 1H), 2.58-2.54 (m, 1H). |

Example 7

Preparation of N-(3-((5-(4-(aminomethyl)-4-methyl-piperidin-1-yl)-6-oxo-1,6-dihydropyrazin-2-yl)thio)-2-chlorophenyl)-4-hydroxy-1,5,5-trimethyl-2-oxo-2,5-dihydro-1H-pyrrole-3-carboxamide

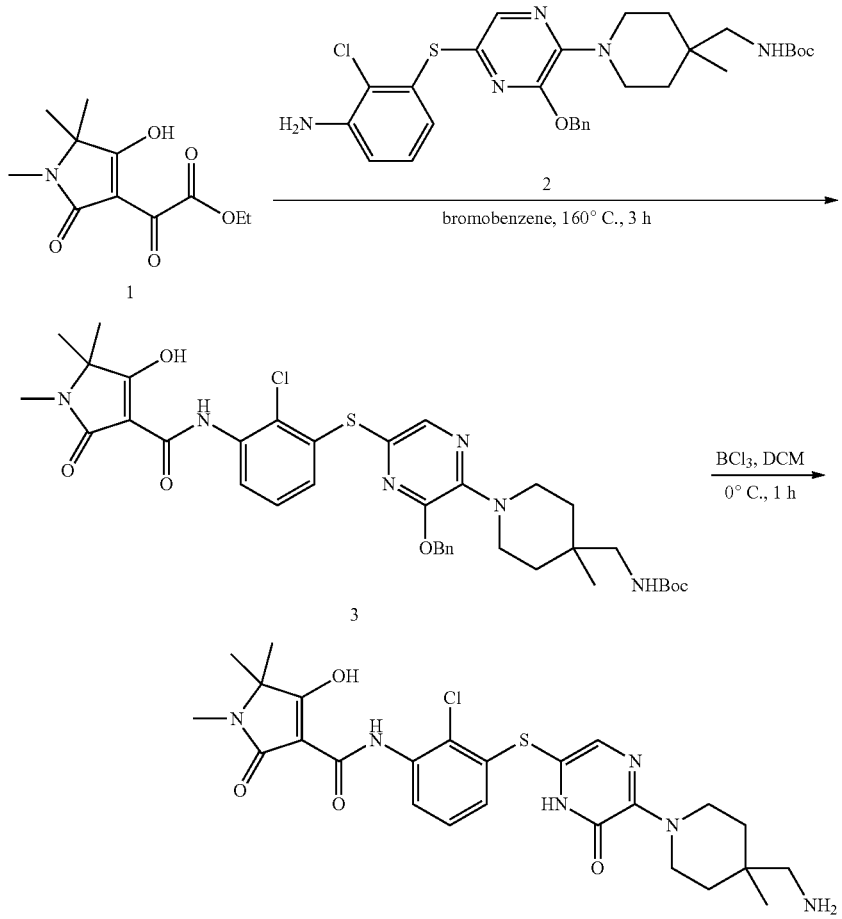 [SMILES: CCOC(=O)C(=O)C1=C(O)C(C)(C)N(C)C1=O ; CC1(CNC(=O)OC(C)(C)C)CCN(c2ncc(Sc3cccc(N)c3Cl)nc2OCc2ccccc2)CC1 ; CN1C(=O)C(C(=O)Nc2cccc(Sc3cnc(N4CCC(C)(CNC(=O)OC(C)(C)C)CC4)c(OCc4ccccc4)n3)c2Cl)=C(O)C1(C)C ; CN1C(=O)C(C(=O)Nc2cccc(Sc3cnc(N4CCC(C)(CN)CC4)c(=O)[nH]3)c2Cl)=C(O)C1(C)C]

Step 1: Preparation of tert-butyl ((1-(3-(benzyloxy)-5-((2-chloro-3-(4-hydroxy-1,5,5-trimethyl-2-oxo-2,5-dihydro-1H-pyrrole-3-carboxannido)phenyl)thio)pyrazin-2-yl)-4-methylpiperidin-4-yl)methyl)carbamate (3)

To a mixture of compound 1 (80 mg, 1.0 eq) in bromobenzene (5 mL) was added compound 2 (107 mg, 0.5 eq) at r.t. and the mixture was degassed and protected with nitrogen. The reaction was stirred at 160° C. for 3 h. Solvent was removed to give crude compound 3 as an oil (140 mg, 100%).

Step 2: Preparation of N-(3-((5-(4-(aminomethyl)-4-methylpiperidin-1-yl)-6-oxo-1,6-dihydropyrazin-2-yl)thio)-2-chlorophenyl)-4-hydroxy-1,5,5-trimethyl-2-oxo-2,5-dihydro-1H-pyrrole-3-carboxamide To a solution of compound 3 (140 mg, 1.0 eq) in DCM (3 mL) was added BCl$_3$(1.9 mL, 1.0 mol/L in DCM, 10.0 eq) at room temperature. The mixture was stirred at r.t. for 1 h. The mixture was quenched by MeOH (3 mL) followed by standard work up process. Desired compound was obtained after prep-HPLC as a slightly red solid (25 mg, 12%). LC-MS: [M+H]+=547. $^1$H NMR (400 MHz, DMSO) δ 11.37 (br s, 1H), 8.46 (d, J=8.0 Hz, 1H), 8.30 (s, 1H), 7.18 (s, 1H), 7.09 (s, 1H), 6.49 (d, J=8.4 Hz, 1H), 4.24-4.21 (m, 2H), 3.55-3.48 (m, 2H), 2.74 (s, 3H), 2.65 (s, 2H), 1.55-1.50 (m, 2H), 1.38-1.33 (m, 2H), 1.12 (s, 6H), 1.02 (s, 3H).

The compounds in Table D below were synthesized by similar manners using appropriate reagents and conditions. The compounds listed in Table D are merely non-limiting examples. Other subject compounds could also be made using similar methods.

Example 8

Preparation of intermediate tert-butyl ((1-(3-(benzyloxy)-5-bromopyrazin-2-yl)-4-methylpiperidin-4-yl)methyl)carbamate

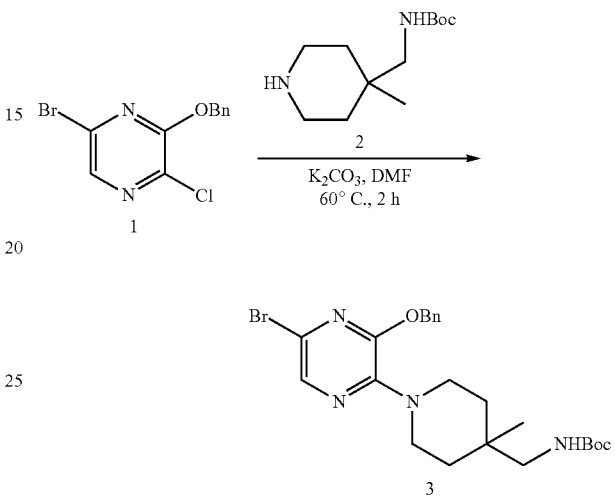

To a solution of compound 1 (320 mg, 1.0 eq) in DMF (5 mL) was added compound 2 (292 mg, 1.2 eq) and K$_2$CO$_3$ (441 mg, 3.0 eq) at rt. The reaction mixture was stirred at 60° C. under Ar atmosphere for 2 hours before it was quenched by water. The desired compound was obtained after standard work up process as a white solid (140 mg, 26%).

TABLE D

| Compound ID | $^1$H-NMR & MS [M + 1]+ |
|---|---|
| 31 | LC-MS: [M + H]+: 574<br>$^1$H NMR (400 MHz, DMSO) δ 13.28 (br s, 1 H), 8.42 (d, J = 7.6 Hz, 1H), 8.16 (s, 1H), 7.68 (d, J = 4.4 Hz, 1H), 7.21-7.17 (m, 2H), 7.01-6.98 (m, 1H), 6.54 (d, J = 8.0 Hz, 1H), 4.27-4.21 (m, 2H), 3.59-3.50 (m, 2H), 2.79 (s, 2H), 1.58-1.54 (m, 2H), 1.43-1.40 (m, 2H), 1.07 (s, 3H). |
| 29 | LC-MS: [M + H]+: 568.3<br>$^1$H NMR (400 MHz, DMSO-d6) δ2.15 (brs, 1H), 9.06 (d, J = 6.4 Hz, 1H), 8.30-8.17 (m, 1H), 7.72 (brs, 1H), 7.58 (brs, 2H), 7.46 (t, J = 6.4 Hz, 1H), 7.34 (brs, 2H), 7.22 (s, 1H), 6.76 (brs, 1H), 4.30-4.24 (m, 2H), 3.57-3.51 (m, 2H), 2.81-2.75 (m, 2H), 1.59-1.51 (m, 2H), 1.43-1.40 (m, 2H), 1.07 (s, 3H). |
| 32 | LC-MS: [M + H]+: 557<br>$^1$H NMR (400 MHz, DMSO) δ 12.74 (br s, 1 H), 8.42-8.35 (m, 1H), 8.20 (s, 1H), 7.34 (s, 1H), 7.21 (s, 2H), 6.97-6.92 (m, 1H), 6.61-6.57 (m, 1H), 4.28-4.21 (m, 2H), 3.58-3.48 (m, 2H), 2.75 (s, 2H), 1.58-1.52 (m, 2H), 1.42-1.36 (m, 2H), 1.06 (s, 3H). |
| 30 | LC-MS: [M + H]+: 568.3<br>$^1$H NMR (400 MHz, DMSO-d$_6$) δ12.15 (brs, 1H), 9.06 (d, J = 6.4 Hz, 1H), 8.30-8.17 (m, 1H), 7.72 (brs, 1H), 7.58 (brs, 2H), 7.46 (t, J = 6.4 Hz, 1H), 7.34 (brs, 2H), 7.22 (s, 1H), 6.76 (brs, 1H), 4.30-4.24 (m, 2H), 3.57-3.51 (m, 2H), 2.81-2.75 (m, 2H), 1.59-1.51 (m, 2H), 1.43-1.40 (m, 2H), 1.07 (s, 3H). |
| 33 | LC-MS: [M + H]+: 572.2<br>$^1$H NMR (400 MHz, MeOD) δ 8.31 (s, 1H), 7.25 (s, 2H), 6.81 (s, 1H), 4.39 (d, J = 13.3 Hz, 2H), 3.99 (s, 2H), 3.76-3.43 (m, 2H), 2.96-2.87 (m, 4H), 2.01-1.92 (m, 4H), 1.76-1.37 (m, 4H), 1.18 (s, 3H). |

Example 9

Preparation of 1-(3-aminocyclohexyl)-4-(2,3-dichlorophenyl)pyridin-2(1H)-one

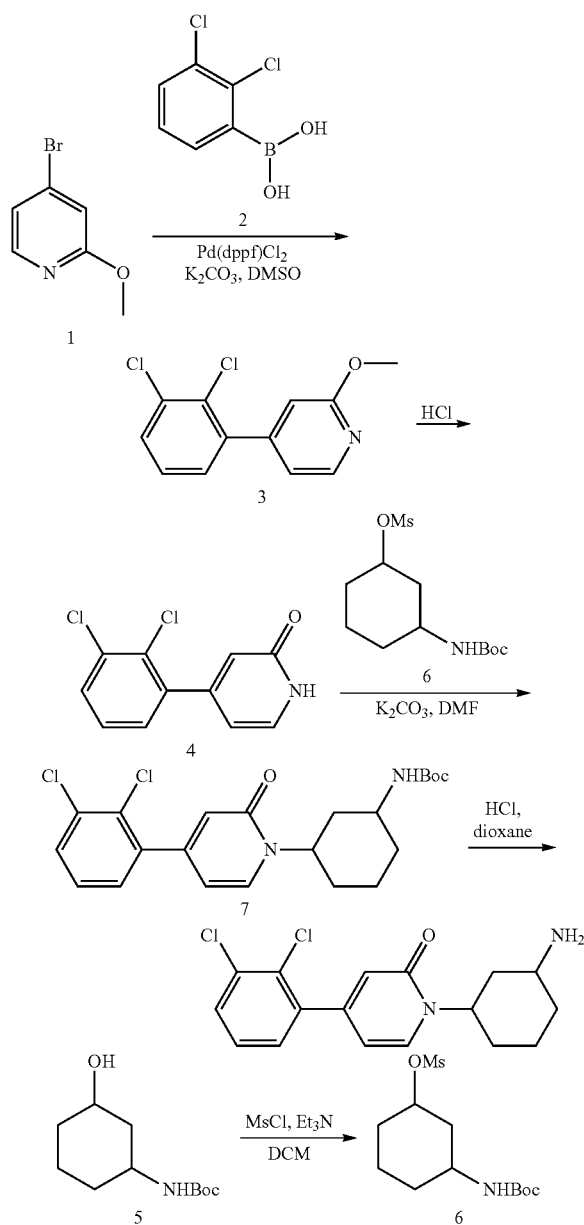

Step 1: Preparation of 4-(2,3-dichlorophenyl)-2-methoxypyridine (3)

To a solution of compound 1 (2.0 g, 1 eq) in DMSO were added compound 2 (1 g, 1 eq), PdCl$_2$(dppf) (0.77 g, 0.1 eq) and K$_2$CO$_3$ (2.9 g, 2 eq). The mixture was stirred at 95° C. overnight. The reaction was quenched by water, and worked up under standard procedure. The residue was purified by flash column chromatography to give the title compound (2.1 g, yield: 78.9%).

Step 2: Preparation of 4-(2,3-dichlorophenyl)pyridin-2(1H)-one (4)

The mixture of compound 3 (1.0 g, 1 eq) in conc. HCl (20 mL) was stirred at 150° C. overnight. Ice-water was added into the mixture and pH was adjusted to 7. After standard work up procedure, title compound (0.94 g, yield: 100%) was obtained.

Step 3: Preparation of 3-((tert-butoxycarbonyl)amino)cyclohexyl methanesulfonate (6)

To a solution of compound 5 (1.0 g, 1.0 eq), Et$_3$N (1 ml, 1.5 eq) in DCM (20 mL) was added MsCl. The mixture was quenched with water (30 mL) 2 hours later. After standard work up procedure, the residue was purified by flash column chromatography to give the title compound (1.0 g, yield: 73.5%).

Step 4: Preparation of tert-butyl (3-(4-(2,3-dichlorophenyl)-2-oxopyridin-1(2H)-yl)cyclohexyl)carbamate (7)

To a solution of compound 4 (1.0 g, 1.0 eq) in DMF (10 mL) was added K$_2$CO$_3$ (1.7 g, 3.0 eq) and compound 6 (1.7 g, 1.2 eq), and the mixture was stirred at 110° C. overnight. The reaction was quenched with water (30 mL), followed by standard work up procedure. The residue was purified by flash column chromatography to give the title compound (170 mg, yield: 9.34%).

Step 5: Synthesis of 1-(3-aminocyclohexyl)-4-(2,3-dichlorophenyl)pyridin-2(1H)-one The solution of compound 7 (170 mg, 1.0 eq) in 4M HCl/dioxane (5 mL) was stirred at room temperature for 30 min. NaOH solution was added to the mixture at 0° C., and the mixture was extracted with EA (3×30 mL). The organic layer was dried over Na$_2$SO$_4$, filtered and concentrated. The final compound was obtained after Pre-HPLC as HCOOH salt (100 mg, yield: 76.3%). LC-MS: [M+H]+=338.2. $^1$H NMR (400 MHz, CD$_3$OD) δ 8.22-8.21 (d, J=4.8 Hz 1H), 7.63-7.61 (d, J=7.6 Hz, 1H), 7.4-(m, 1H), 7.33-7.31 (m, 2H), 6.85 (s, 1H), 5.54 (s, 1H), 3.53 (m, 1H), 2.48-2.44 (d, J=13.2 Hz, 1H), 2.082-2.01 (m, 2H), 1.79 (m, 3H), 1.66 (m 3H).

Pharmacological Testing

Some of the compounds disclosed herein were assessed for their ability to selectively inhibit SHP2 activity. The inhibitory properties of the compounds described herein can be evidenced by testing in the following assays.

SHP2 Phosphatase Assays

IC$_{50}$ values were determined at room temperature in 384-well black polystyrene plate, using a final reaction volume of 15 μl and the following assay buffer conditions: 60 mM Hepes (pH=7.2), 75 mM NaCl, 75 mM KCl, and 1 mM EDTA, 0.05% P-20, 5 mM dithiothreitol (DTT). Full length SHP2 enzyme (diluted to 0.1 nM in reaction buffer) were co-incubated with 1 uM IRS-1 peptide and 0.01 nM to 10 μM compounds of the disclosure for 60 min. The surrogate substrate DiFMUP (5 μL, 100 LIM) was added, and incubated at rt for 60 min. The reaction was then quenched by the addition of 5 μL of a 40 μM solution of bpV(Phen). The fluorescence signal was monitored using a microplate reader (Envision, Perkin-Elmer) using excitation and emission wavelengths of 360 nm and 450 nm, respectively. The inhibitor dose-response curves were analyzed using normalized IC$_{50}$ regression curve fitting with control-based normalization. The inhibitory activity results of the compounds of the disclosure is shown in Table 2.

TABLE 2

| Compound ID | IC$_{50}$ |
| --- | --- |
| 2 | +++ |
| 35 | +++ |
| 52 | +++ |
| 34 | +++ |
| 77 | +++ |
| 31 | +++ |
| 29 | +++ |
| 32 | +++ |
| 28 | +++ |
| 30 | +++ |
| 14 | +++ |
| 73 | +++ |
| 74 | +++ |
| 33 | +++ |
| 79 | +++ |
| 80 | +++ |
| 81 | +++ |
| 84 | +++ |
| 107 | +++ |
| 109 | +++ |
| 82 | +++ |
| 83 | +++ |
| 13 | +++ |
| 86 | +++ |
| 108 | +++ |
| 87 | +++ |
| 88 | +++ |
| 73 | +++ |

IC$_{50}$:
+++: ≤50 nM;
++: ≤100 nM;
+: ≤1 μM;

p-ERK/total ERK Cellular Assay

Cells were seeded in 384-well cell culture plate and incubated overnight. Test compounds were added to the cell plate and the plate was incubated for 2-6 hours. To detect p-ERK, the cell plate was used AlphaLISA SureFire Ultra p-ERK kit; to detect total ERK, the cell plate was used total ERK HTRF kit. The plate was read on the Envision. The inhibitory activity results of the compounds of the disclosure is shown in Table 3.

TABLE 3

| Compound ID | IC$_{50}$ |
| --- | --- |
| 2 | ++ |
| 35 | ++ |
| 34 | ++ |
| 10 | +++ |
| 31 | +++ |
| 29 | +++ |
| 30 | +++ |
| 14 | +++ |
| 73 | +++ |
| 33 | +++ |
| 79 | +++ |
| 80 | +++ |
| 81 | +++ |
| 84 | +++ |
| 109 | +++ |
| 82 | +++ |
| 83 | +++ |

IC$_{50}$:
+++: ≤0.1 μM;
++: ≤0.5 μM;
+: ≤1 μM;

Cell Proliferation Assay

Firstly, the cells were seeded in 384-well cell culture plate and incubate overnight. The test compounds were added to the cell plate and incubated for 3-5 days. The cell plate was then detected using CellTiter Glo reagents. The inhibitory activity results of the compounds of the disclosure is shown in Table 4.

TABLE 4

| Compound ID | IC$_{50}$ |
| --- | --- |
| 2 | ++ |
| 10 | ++ |
| 31 | ++ |
| 29 | ++ |
| 14 | +++ |
| 73 | ++ |
| 81 | +++ |
| 84 | +++ |
| 109 | ++ |
| 82 | ++ |
| 83 | +++ |

IC$_{50}$:
+++: ≤1 μM;
++: ≤5 μM;
+: ≤10 μM

KYSE-520 Xenograft Model

KYSE-520 cells were expanded in culture, harvested and injected subcutaneously into 6-8 weeks old female BALB/c nude mice (5×10$^6$ cell/each mouse, supplemented with Matrigel (1:1) for tumor development, n=9 per group). Subsequent administration of a compound by oral gavage started when the mean tumor size reached approximately 150-200 mm$^3$. During the treatment (once a day for 4 weeks), the tumor volumes were measured using a caliper. Statistical analysis of difference in tumor volume among the groups were evaluated using a one-way ANOVA. Vehicle alone was the negative control.

Many of the compounds described herein is very potent and selective, with enzymatic IC$_{50}$ less than 10 nM. The compounds tested also displayed superior anti-tumor activities in the in vivo animal models. In some embodiments, the dose amount per day falls within the range of 3-100 mg/kg to achieve the tumor regression or >80% tumor growth inhibition.

Unless otherwise indicated, all numbers expressing quantities of ingredients, properties such as molecular weight, reaction conditions, and etc. used in herein are to be understood as being modified in all instances by the term "about." Each numerical parameter should at least be construed in light of the number of reported significant digits and by applying ordinary rounding techniques. Accordingly, unless indicated to the contrary, the numerical parameters may be modified according to the desired properties sought to be achieved, and should, therefore, be considered as part of the disclosure. At the very least, the examples shown herein are for illustration only, not as an attempt to limit the scope of the disclosure.

The terms "a," "an," "the" and similar referents used in the context of describing embodiments of the present disclosure (especially in the context of the following claims) are to be construed to cover both the singular and the plural, unless otherwise indicated herein or clearly contradicted by context. All methods described herein may be performed in any suitable order unless otherwise indicated herein or otherwise clearly contradicted by context. The use of any and all examples, or exemplary language (e.g., "such as") provided herein is intended merely to better illustrate embodiments of the present disclosure and does not pose a limitation on the scope of any claim. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

Certain embodiments are described herein, including the best mode known to the inventors for carrying out the embodiments. Of course, variations on these described embodiments will become apparent to those of ordinary skill in the art upon reading the foregoing description. The inventor expects skilled artisans to employ such variations as appropriate, and the inventors intend for the embodiments of the present disclosure to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A compound represented by a formula:

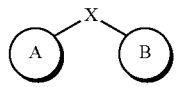

or a pharmaceutically acceptable salt thereof;
wherein X is S;
Ring A is an optionally substituted aryl having 6-10 ring carbon atoms; an optionally substituted 5-membered mono-cyclic heteroaryl comprising 0-4 ring nitrogen atoms, 0-1 ring oxygen atom, 0-1 ring sulfur atom, and at least one N, O, or S ring atom; an optionally substituted 6-membered mono-cyclic heteroaryl comprising 1-3 ring nitrogen atoms; or an optionally substituted bicyclic ring system having 5-10 ring carbon atoms, 0-4 ring nitrogen atoms, 0-1 ring oxygen atom, or 0-1 ring sulfur atom, wherein the bicyclic ring system is unsaturated or partially saturated;
Ring B is:

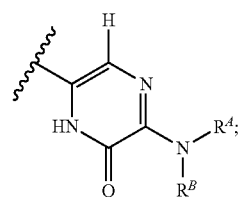

wherein $R^A$ and $R^B$ are independently H or $C_{1-12}$ hydrocarbyl, or —N($R^A$)($R^B$) is an optionally substituted heterocyclic ring system, wherein the heterocyclic ring system is a mono-cyclic ring having 2-8 ring carbon atoms, 1-2 ring nitrogen atoms, 0-1 ring oxygen atom, and 0-1 ring sulfur atom; a bicyclic ring system having 5-12 ring carbon atoms, 1-2 ring nitrogen atoms, 0-1 ring oxygen atom, and 0-1 ring sulfur atom; or a tricyclic ring system having 8-16 ring carbon atoms, 1-2 ring nitrogen atoms, 0-1 ring oxygen atom, and 0-1 ring sulfur atom; wherein the bicyclic ring system is a spiro, fused, or bridged ring system, wherein the heterocyclic ring system is saturated or partially saturated; and wherein substituted Ring A and substituted Ring B are independently having one or more substituents; wherein each substituent of Ring A or Ring B is independently alkyl, alkenyl, alkynyl, —NR$^A$R$^B$, —OR$^A$, —S—R$^A$, aryl, heteroaryl, heterocyclyl, hydroxy, alkoxy, aryloxy, —C(O)—R$^A$, R$^A$—C(O)O— alkylcarboxylate, —SH, cyano, halogen, —C(=S)—R$^A$, —OC(O)—NR$^A$R$^B$, R$^A$—OC(O)—N(R$^A$)—, —OC(=S)—NR$^A$R$^B$, R$^A$—OC(=S)—N(R$^A$)—, —C(O)NR$^A$R$^B$, R$^A$—C(O)N(R$^A$)—, (R$^A$R$^B$)N—S(O)$_2$—, —N(R$^A$)—S(O)$_2$—R$^A$, nitro, R$^A$—S(=O)—, —S(O)$_2$—R$^A$, haloalkyl, haloalkoxy, —S(O)$_2$C(X')$_3$ wherein X' is halogen, —N(R$^A$)S(O)$_2$C(X')$_3$ wherein X' is halogen, amino, —N(R$^A$)C(O)-heteroaryl, —N(R$^A$)C(O)-heterocyclyl, —C(O)N(R$^A$)-heteroaryl, —C(O)N(R$^A$)-heterocyclyl, or a combination thereof.

2. The compound of claim 1, wherein Ring A is optionally substituted phenyl.

3. The compound of claim 1, wherein Ring A is optionally substituted pyridinyl.

4. The compound of claim 1, wherein Ring A is optionally substituted pyridin-4-yl.

5. The compound of claim 1, wherein Ring A is optionally substituted 2,3-dichlorophenyl.

6. The compound of claim 1, wherein Ring A is optionally substituted 2,3-dichloro-pyridin-4-yl.

7. The compound of claim 1, wherein Ring A is optionally substituted 2-amino-3-chloropyridin-4-yl.

8. The compound of claim 1, wherein Ring A is any one of the following:

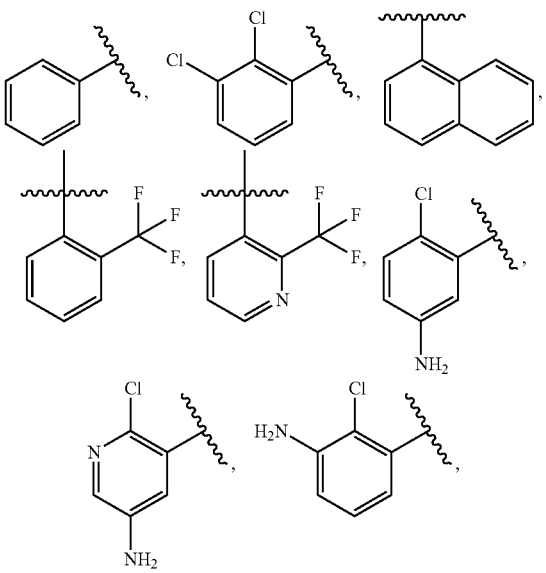

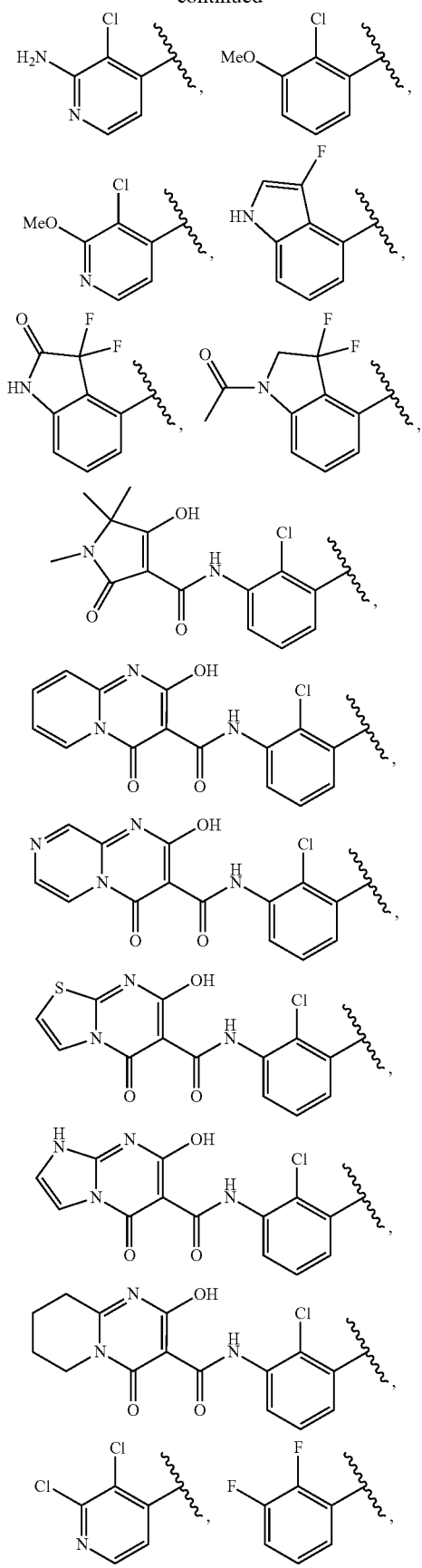
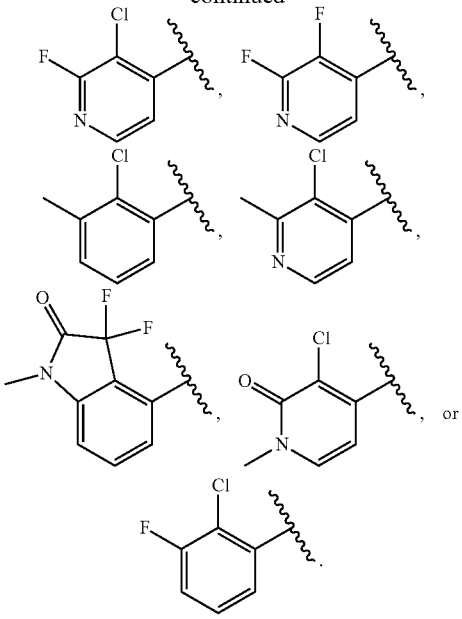
9. The compound of claim 1, wherein Ring B is 5-((3S, 4S)-4-amino-3-methyl-2-oxa-8-azaspiro[4.5]decan-8-yl)-6-oxo-1,6-dihydropyrazin-2-yl.
10. The compound of claim 1, wherein Ring B is any one of the following:
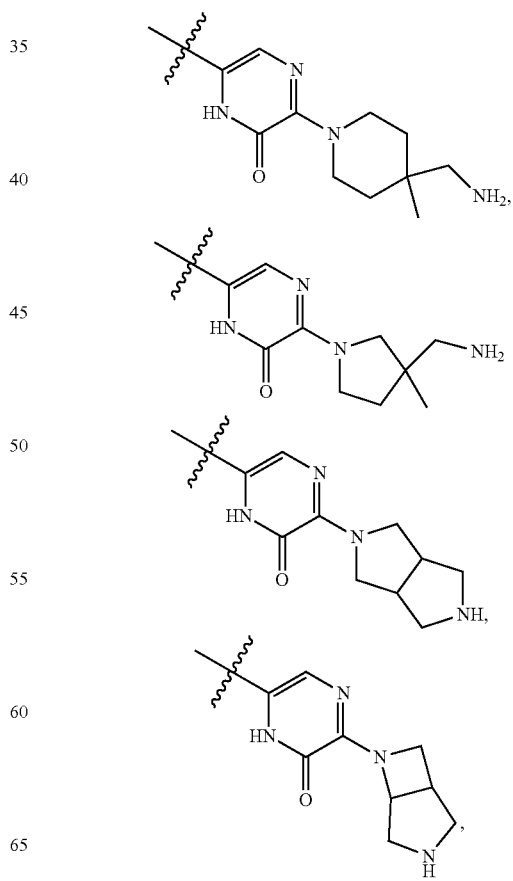

113
-continued
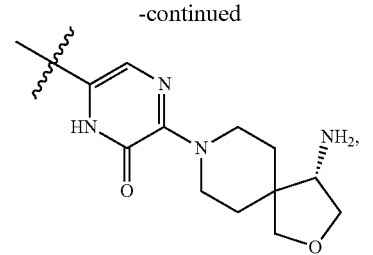
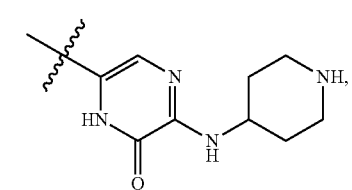
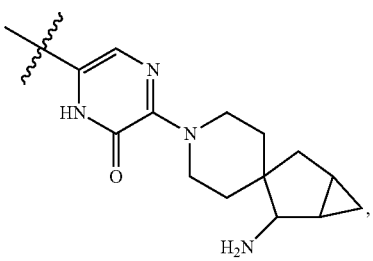
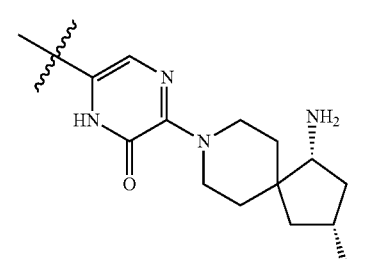
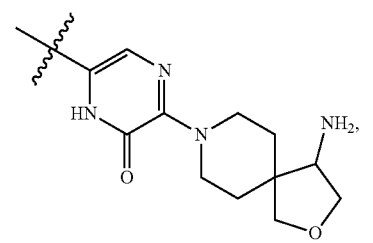
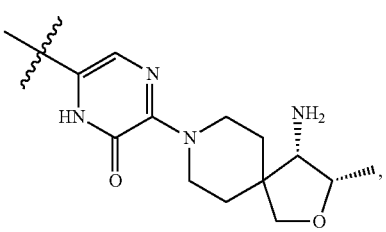
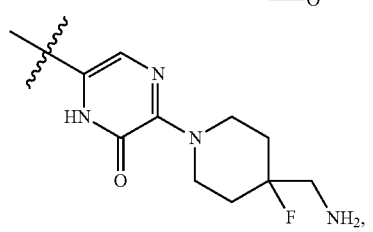
114
-continued
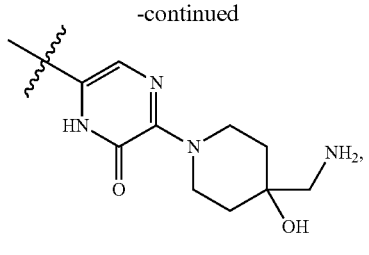
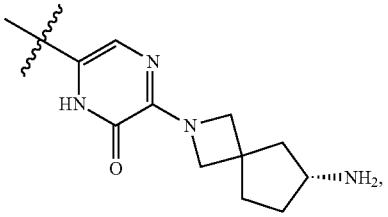
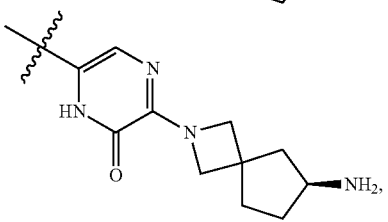
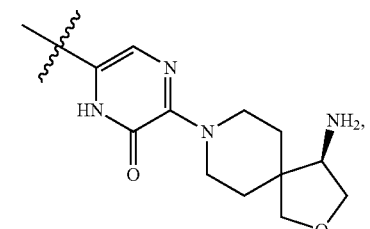
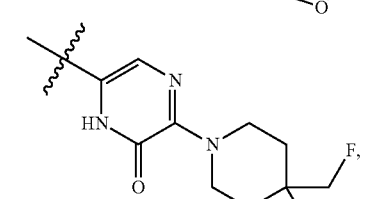
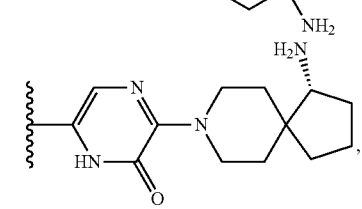
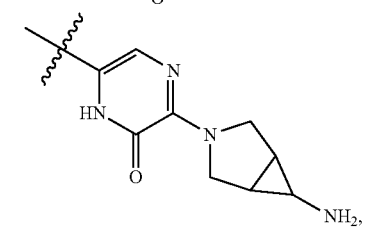
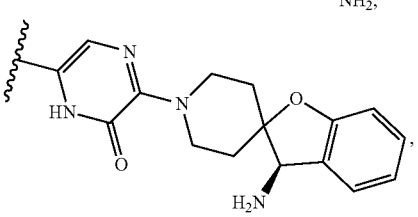

-continued
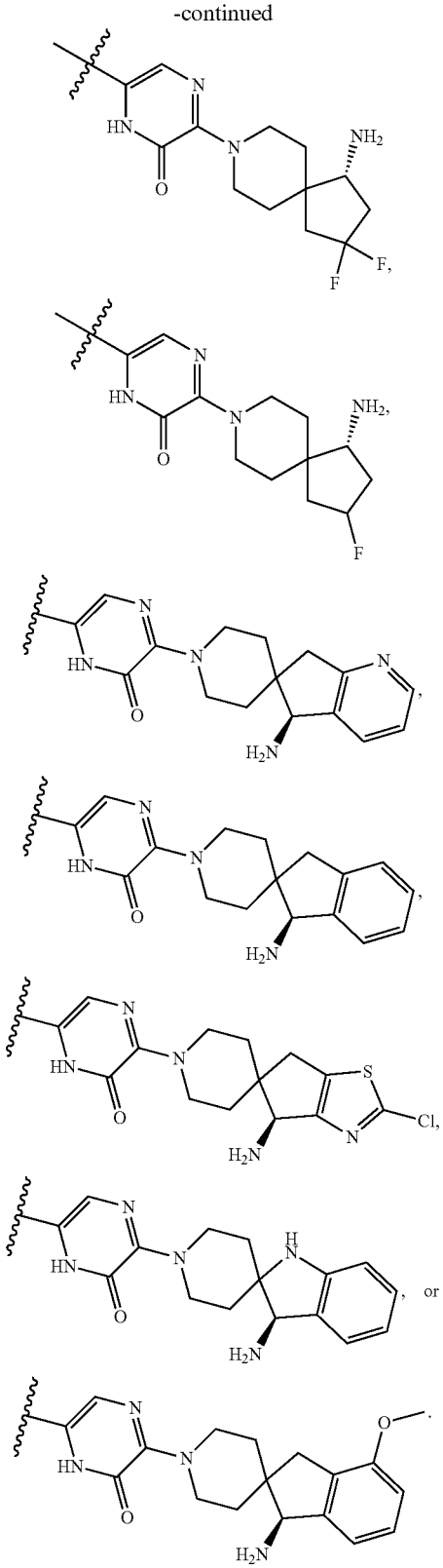
11. The compound of claim 1, wherein the compound is an R-enantiomer.
12. The compound of claim 1, wherein the compound is an S-enantiomer.
13. The compound of claim 1 or a pharmaceutically acceptable salt thereof, wherein the compound is any one of the following compounds that is:
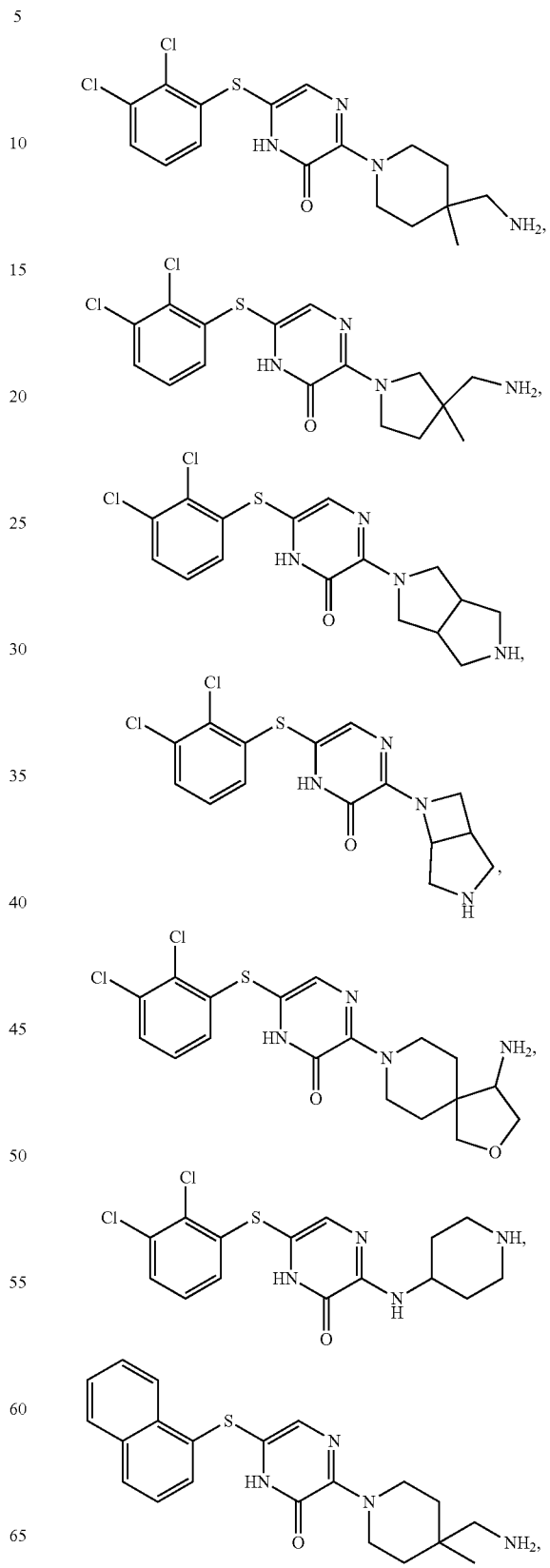

117
-continued
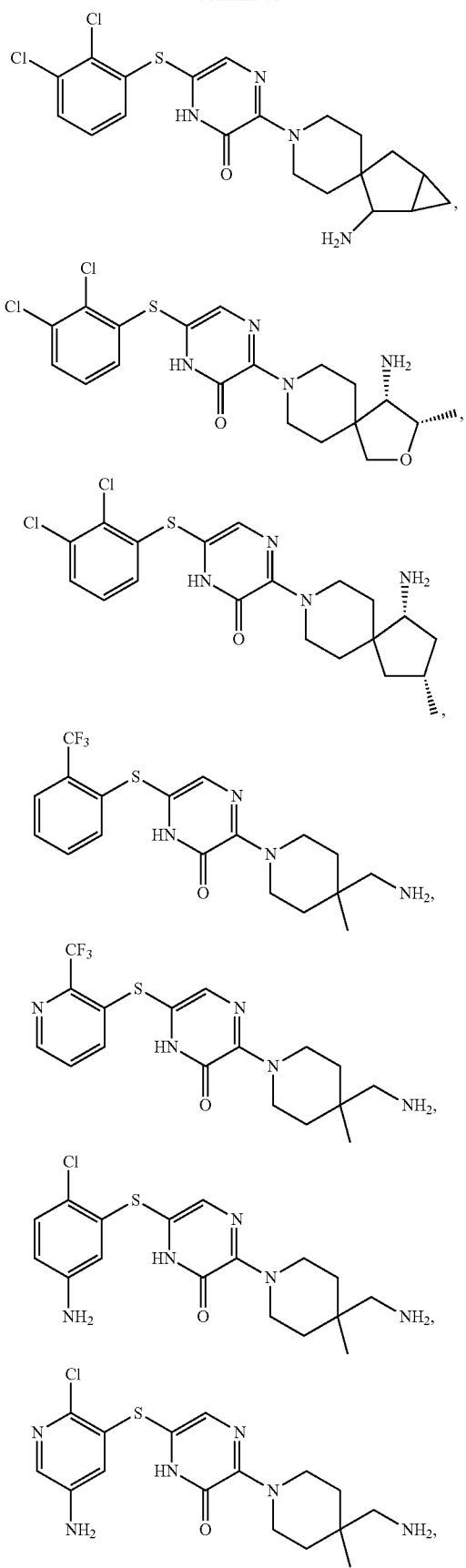
118
-continued
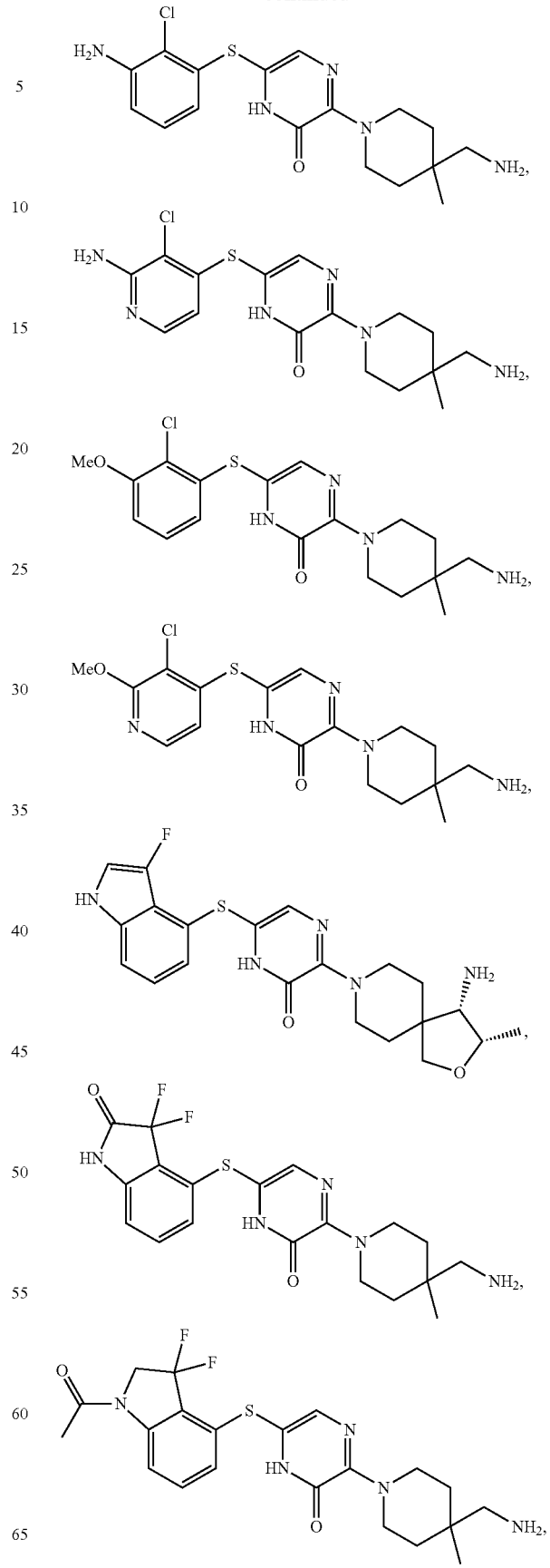

-continued
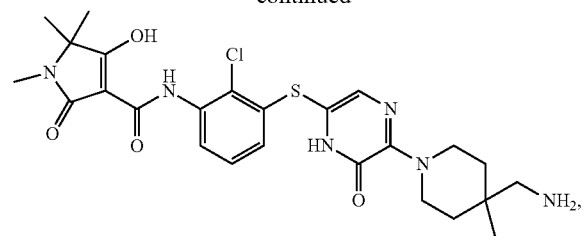
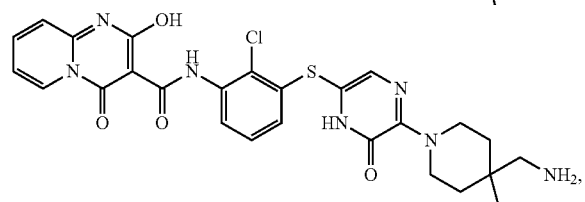
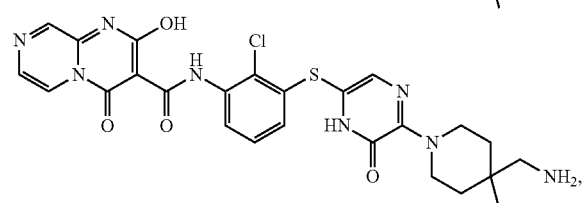
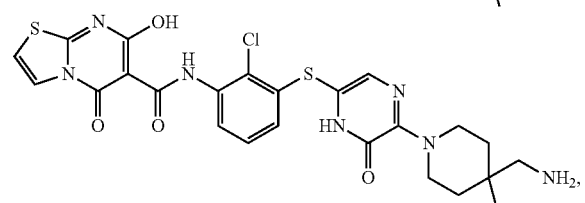
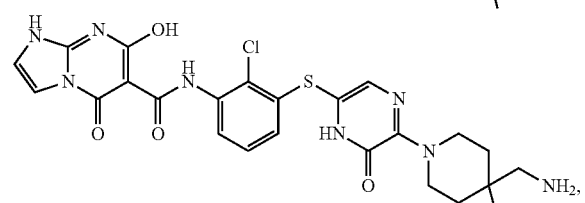
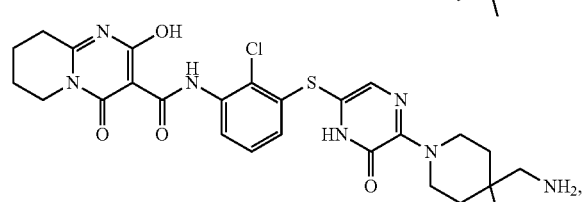
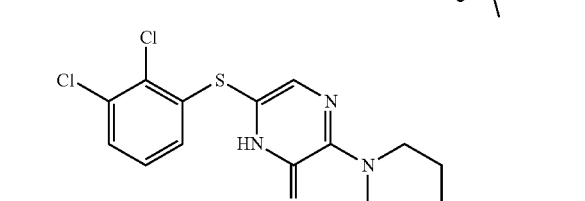
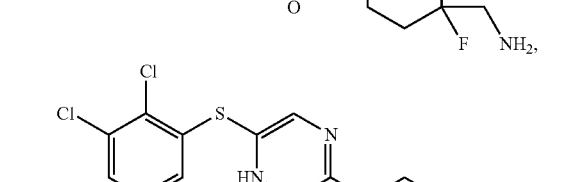
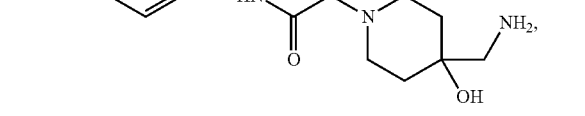
-continued
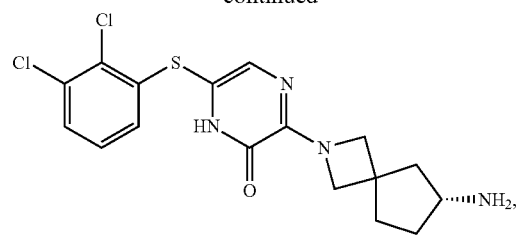
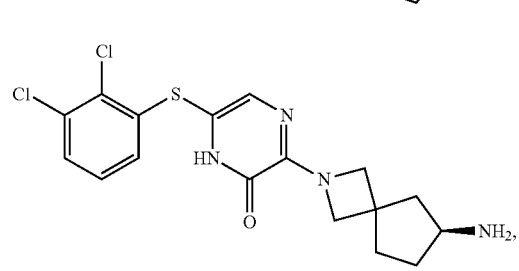
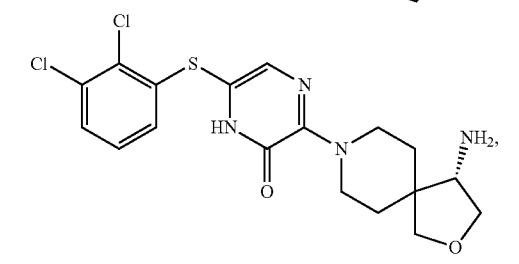
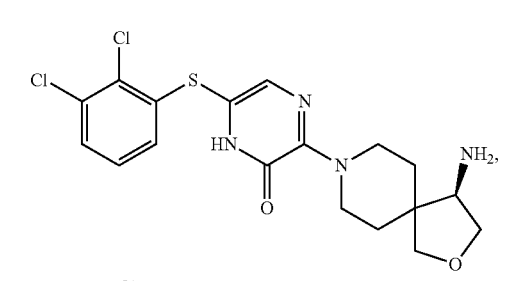
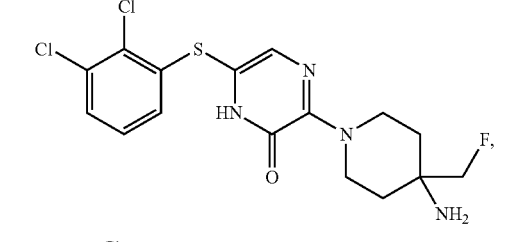
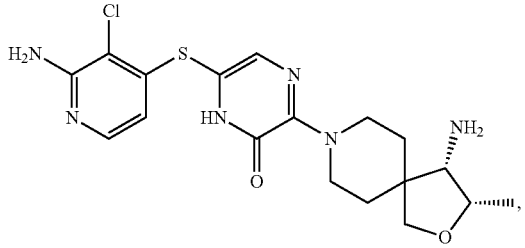
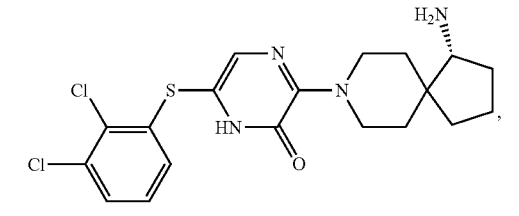

-continued
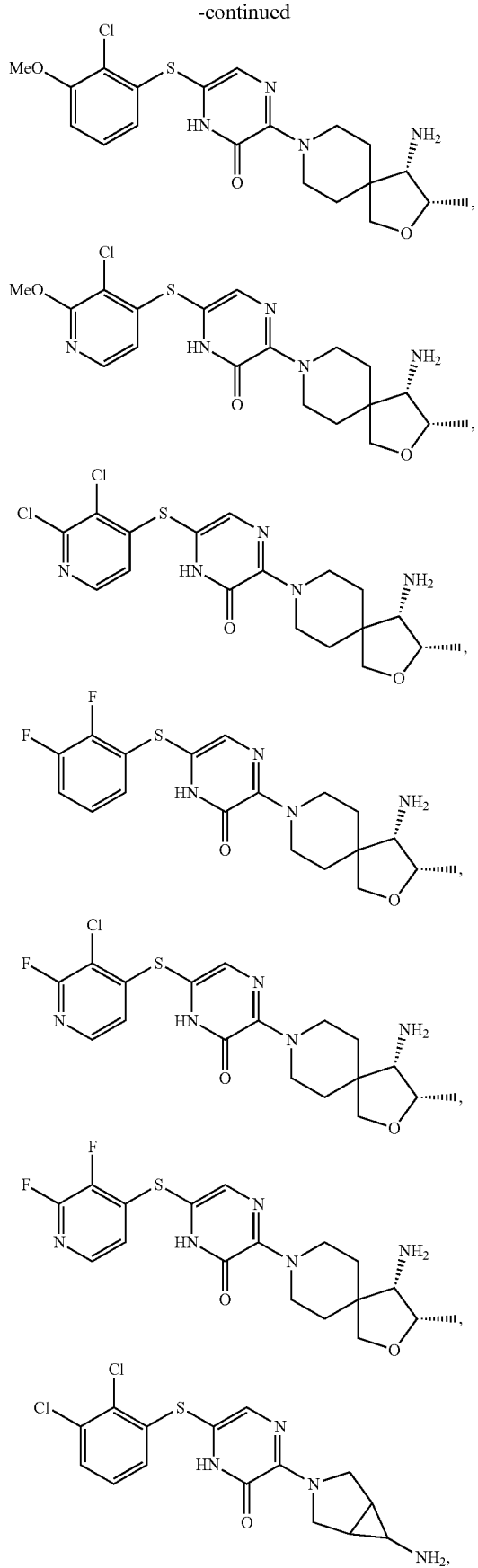
-continued
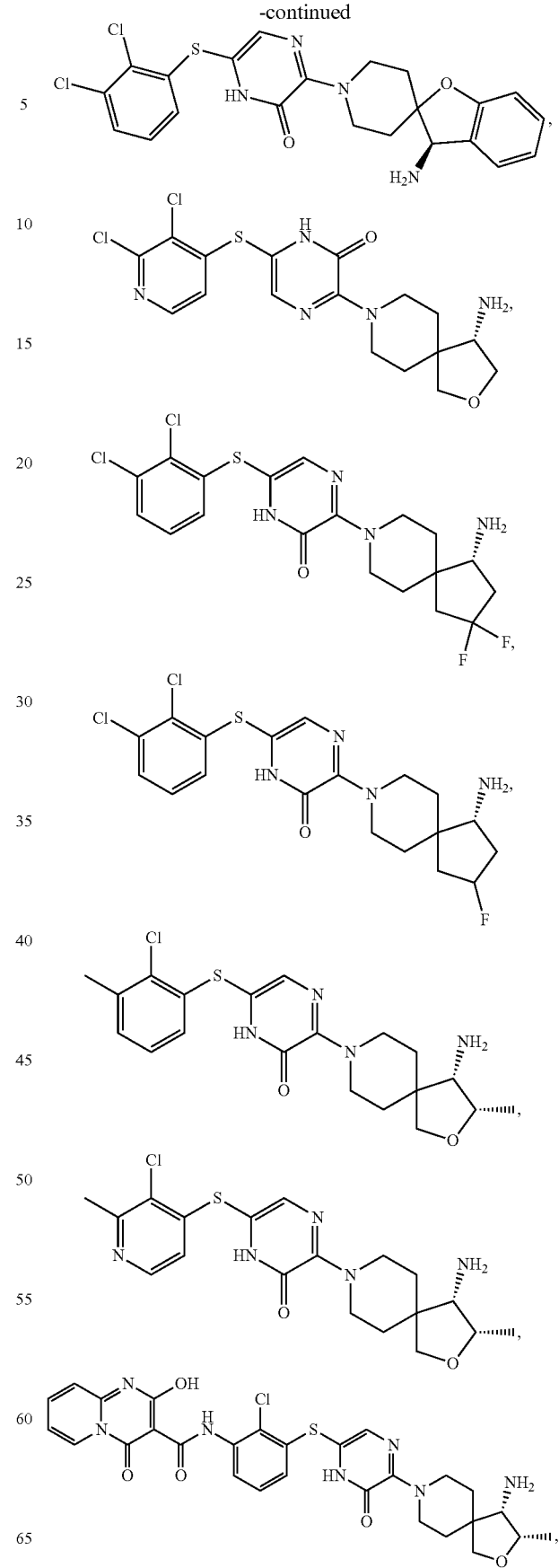

123
-continued

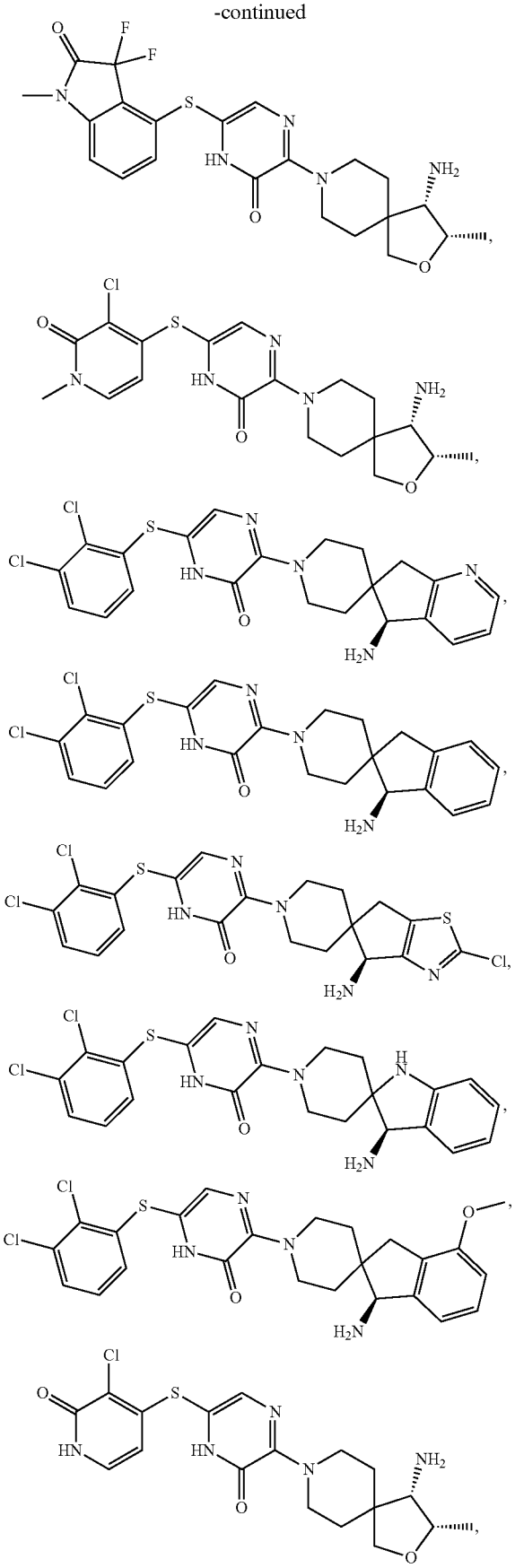

124
-continued

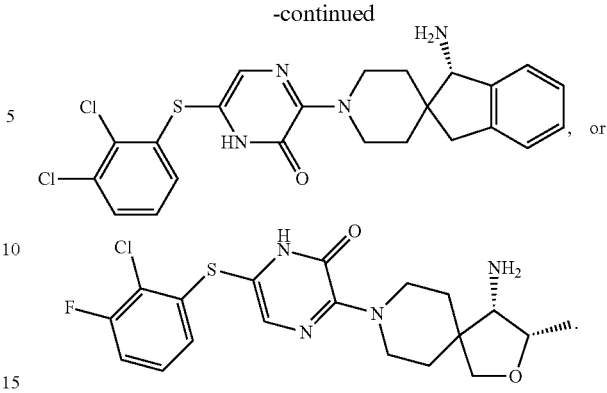

14. The compound of claim 1, wherein any substituent of the compound has a molecular weight of about 15 g/mol to about 500 g/mol.

15. A pharmaceutical composition comprising a compound of claim 1 or a pharmaceutically acceptable salt thereof, and a pharmaceutically acceptable vehicle, diluent, or carrier.

16. A compound represented by a formula:

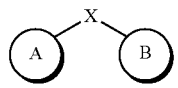

or a pharmaceutically acceptable salt thereof;
wherein X is S;
wherein Ring A is optionally substituted phenyl, optionally substituted naphthalen-1-yl, optionally substituted pyridin-3-yl, optionally substituted pyridin-4-yl, optionally substituted 2-oxo-1,2-dihydropyridin-4-yl, optionally substituted 1H-indol-4-yl, optionally substituted 2-oxoindolin-4-yl, optionally substituted indolin-4-yl, optionally substituted 3-(2-oxo-2,5-dihydro-1H-pyrrole-3-carboxamido)phenyl, optionally substituted 3-(4-oxo-4H-pyrido[1,2-a]pyrimidine-3-carboxamido)phenyl, optionally substituted 3-(4-oxo-4H-pyrazino[1,2-a]pyrimidine-3-carboxamido)phenyl, optionally substituted 3-(5-oxo-5H-thiazolo[3,2-a]pyrimidine-6-carboxamido)phenyl, optionally substituted 3-(5-oxo-1,5-dihydroimidazo[1,2-a]pyrimidine-6-carboxamido)phenyl, or optionally substituted 3-(4-oxo-6,7,8,9-tetrahydro-4H-pyrido[1,2-a]pyrimidine-3-carboxamido)phenyl;
wherein Ring B is 6-oxo-5-(piperidin-1-yl)-1,6-dihydropyrazin-2-yl, 6-oxo-5-(pyrrolidin-1-yl)-1,6-dihydropyrazin-2-yl, 5-(hexahydropyrrolo[3,4-c]pyrrol-2(1H)-yl)-6-oxo-1,6-dihydropyrazin-2-yl, 5-(3,6-diazabicyclo[3.2.0]heptan-6-yl)-6-oxo-1,6-dihydropyrazin-2-yl, 6-oxo-5-(2-oxa-8-azaspiro[4.5]decan-8-yl)-1,6-dihydropyrazin-2-yl, 6-oxo-5-(piperidin-4-ylamino)-1,6-dihydropyrazin-2-yl, optionally substituted 6-oxo-5-(spiro[bicyclo[3.1.0]hexane-3,4'-piperidin]-1'-yl)-1,6-dihydropyrazin-2-yl, 6-oxo-5-(8-azaspiro[4.5]decan-8-yl)-1,6-dihydropyrazin-2-yl, 6-oxo-5-(2-azaspiro[3.4]octan-2-yl)-1,6-dihydropyrazin-2-yl, 5-(3-azabicyclo[3.1.0]hexan-3-yl)-6-oxo-1,6-dihydropyrazin-2-yl, 6-oxo-5-(3H-spiro[benzofuran-2,4'-piperidin]-1'-yl)-1,6-dihydropyrazin-2-yl, 5-(5,7-dihydrospiro[cyclopenta[b]pyridine-6,4'-piperidin]-1'-yl)-6-oxo-1,6-dihydropyrazin-2-yl, 5-(1,3-dihydrospiro[indene-2,4'- piperidin]-1'-yl)-6-oxo-1,6-dihydropyrazin-2-yl, 5-(4,6-dihydrospiro[cyclopenta[d]thiazole-5,4'-piperidin]-1'-yl)-6-oxo-1,6-dihydropyrazin-2-yl, or 6-oxo-5-(spiro[indoline-2,4'-piperidin]-1'-yl)-1,6-dihydropyrazin-2-yl; and wherein substituted Ring A and substituted Ring B are independently having one or more substituents; wherein each substituent of Ring A or Ring B is independently alkyl, alkenyl, alkynyl, —NR$^A$R$^B$, —OR$^A$, —S—R$^A$, aryl, heteroaryl, heterocyclyl, hydroxy, alkoxy, aryloxy, —C(O)—R$^A$, R$^A$—C(O)O—alkylcarboxylate, —SH, cyano, halogen, —C(=S)—R$^A$, —OC(O)—NR$^A$R$^B$, R$^A$—OC(O)—N(R$^A$)—, —OC(=S)—NR$^A$R$^B$, R$^A$—OC(=S)—N(R$^A$)—, —C(O)NR$^A$R$^B$, R$^A$—C(O)N(R$^A$)—, (R$^A$R$^B$)N—S(O)$_2$—, —N(R$^A$)—S(O)$_2$—R$^A$, nitro, R$^A$—S(=O)—, —S(O)$_2$—R$^A$, haloalkyl, haloalkoxyl, —S(O)$_2$C(X')$_3$ wherein X' is halogen, —N(R$^A$)S(O)$_2$C(X')$_3$ wherein X' is halogen, amino, —N(R$^A$)C(O)-heteroaryl, —N(R$^A$)C(O)-heterocyclyl, —C(O)N(R$^A$)-heteroaryl, —C(O)N(R$^A$)-heterocyclyl, or a combination thereof.

* * * * *